US007790150B2

(12) United States Patent
Papisov et al.

(10) Patent No.: US 7,790,150 B2
(45) Date of Patent: Sep. 7, 2010

(54) DUAL PHASE DRUG RELEASE SYSTEM

(75) Inventors: Mikhail I. Papisov, Winchester, MA (US); Alexander Yurkovetskiy, Littleton, MA (US)

(73) Assignee: The General Hospital Corporation, Boston, MA (US)

( * ) Notice: Subject to any disclaimer, the term of this patent is extended or adjusted under 35 U.S.C. 154(b) by 243 days.

(21) Appl. No.: 10/570,466

(22) PCT Filed: Sep. 4, 2004

(86) PCT No.: PCT/US2004/029130

§ 371 (c)(1),
(2), (4) Date: Feb. 20, 2007

(87) PCT Pub. No.: WO2005/023294

PCT Pub. Date: Mar. 17, 2005

(65) Prior Publication Data

US 2007/0190018 A1     Aug. 16, 2007

Related U.S. Application Data

(60) Provisional application No. 60/500,571, filed on Sep. 5, 2003.

(51) Int. Cl.
*A61K 31/00*      (2006.01)
(52) U.S. Cl. ..................... 424/78.3; 525/417
(58) Field of Classification Search ............... 424/78.3; 525/417
See application file for complete search history.

(56) References Cited

U.S. PATENT DOCUMENTS 5,075,222 A     12/1991   Hannum et al.

(Continued)

FOREIGN PATENT DOCUMENTS

EP     0280474 A2    8/1988

(Continued)

OTHER PUBLICATIONS

Endo et al. Cancer Research. (1988), 48, p. 3330-3335.*

(Continued)

*Primary Examiner*—Kamal A Saeed
*Assistant Examiner*—Valerie Rodriguez-Garcia
(74) *Attorney, Agent, or Firm*—Choate, Hall & Stewart LLP; Brenda Herschbach Jarrell; John P. Rearick

(57) ABSTRACT

The present invention relates to conjugate comprising a carrier substituted with one or more occurrences of a moiety having the structure (I): wherein each occurrence of M is independently a modifier having a molecular weight ≦10 kDa; denotes direct of indirect attachment of M to linker $L^M$; and each occurrence of $L^M$ is independently an optionally substituted succinamide-containing linker, whereby the modifier M is directly or indirectly attached to the succinamide linker through an amide bond, and the carrier is linked directly or indirectly to each occurrence of the succinamide linker through an ester bond. In another aspect, the invention provides compositions comprising the conjugates, methods for their preparation, and methods of use thereof in the treatment of various disorder, including, but not limited to cancer.

(I)

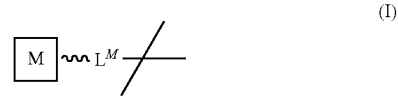

30 Claims, 8 Drawing Sheets

U.S. PATENT DOCUMENTS

| | | | |
|---|---|---|---|
| 5,582,172 | A | 12/1996 | Papisov et al. |
| 5,612,037 | A | 3/1997 | Huebner et al. |
| 5,624,803 | A | 4/1997 | Noonberg et al. |
| 5,811,510 | A | 9/1998 | Papisov |
| 5,817,343 | A | 10/1998 | Burke |
| 5,863,990 | A | 1/1999 | Papisov |
| 5,958,398 | A | 9/1999 | Papisov |
| 6,048,837 | A | 4/2000 | Friedman et al. |
| 6,057,431 | A | 5/2000 | Ishihara et al. |
| 6,294,170 | B1 | 9/2001 | Boone et al. |
| 6,822,086 | B1 | 11/2004 | Papisov |
| 7,160,924 | B2 | 1/2007 | Kinstler et al. |
| 7,270,808 | B2 * | 9/2007 | Cheng et al. ............. 424/78.08 |
| 2002/0082362 | A1 | 6/2002 | Brocchini et al. |
| 2005/0169968 | A1 | 8/2005 | Elmaleh et al. |
| 2006/0019911 | A1 | 1/2006 | Papisov |
| 2006/0058513 | A1 | 3/2006 | Papisov et al. |
| 2006/0069230 | A1 | 3/2006 | Papisov |
| 2008/0019940 | A1 | 1/2008 | Papisov |
| 2009/0148396 | A1 | 6/2009 | Akullian et al. |

FOREIGN PATENT DOCUMENTS

| | | |
|---|---|---|
| EP | 0325270 A2 | 7/1989 |
| EP | 0820473 B1 | 6/2001 |
| EP | 1055685 B1 | 9/2004 |
| EP | 1468036 B1 | 8/2008 |
| WO | WO-9605309 A2 | 2/1996 |
| WO | WO-9640912 A1 | 12/1996 |
| WO | WO-9930561 A1 | 6/1999 |
| WO | WO 01/10468 * | 2/2000 |
| WO | WO-0078355 A2 | 12/2000 |
| WO | WO-0107486 A1 | 2/2001 |
| WO | WO-0110468 | 2/2001 |
| WO | WO 03/059988 * | 7/2003 |
| WO | WO-03059988 | 7/2003 |
| WO | WO-2004009082 A1 | 1/2004 |
| WO | WO-2004009774 A2 | 1/2004 |
| WO | WO-2004089311 A2 | 10/2004 |

OTHER PUBLICATIONS

Jordan, V. C. Nature Reviews: Drug Discovery, 2, 2003, p. 205.*

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Tomlinson et al. (Bioconjugate Chem., 2003, 14(6), 1096-1106).*

Zalipsky et al. (Eur. Polym. J. (1983), vol. 19, No. 12, pp. 1177).*

Feng et al. (Bioorg. Med. Chem. Lett. (2002) 12, pp. 3301).*

Akullian et al. Anti-Angiogenic Fumagillin-Related Polymeric Pro-Drugs exhibit Anti-Tumor Activity in B16 Murine Melanoma and Human Tumor Xenograft Models, Proc. Am. Assoc. Cancer Res. 2007 (Apr. 2007); abstr 2327.

Bendele, A. et al. (1998) Short communication: renal tubular vacuolation in animals treated with polyethylene-glycol-conjugated proteins. Toxicological Sciences. 42, 152-7.

Bethune et al. Pharmacokinetics of a novel camptothecin conjugate (XMT-1001) in the rat and dog, Proc. Am. Assoc. Cancer Res. (2007) abstr 4723.

Bethune, C. et al. Predictive Pharmacokinetics of a Novel Macromolecular Camptothecin Conjugate (XMT-1001) Using Allometric Scaling from Two Species. The AAPS Journal. 2008; 10(S2). (Annual Meeting).

Burke, TG et al. Camptothecin design and delivery approaches for elevating anti-topoisomerase I activities in vivo. Annals of the New York Academy of Sciences 2000, 922:36-45.

Cabodi, S. et al. Targeted drug delivery to breast cancer cells. Proceedings, Dept of Defense Breast Cancer Research Program Meeting, Atlanta, GA, 2000; v.1 p. 307.

Cao, Z. et al. Alkyl esters of camptothecin and 9-nitrocamptothecin: synthesis, in vitro pharmacokinetics, toxicity, and antitumor activity. Journal of Medicinal Chemistry 1998, 41:31-37.

Christensen, M. et al. (1978) Storage of polyvinylpirrollidone (PVP) in tissue following long-term treatment with a PVP-containing Vasopressin preparation. Acta Med. Scand., 204, 295-298.

Conover, CD et al. Camptothecin delivery systems: enhanced efficacy and tumor accumulation of camptothecin following its conjugation to polyethylene glycol via a glycine linker. Cancer Chemother Pharmacol. 1998, 42: 407-414.

Dorwald, F. Zaragoza. Side Reactions in Organic Synthesis: A Guide to Successful Synthesis Design, Weinheim: Wiley-VCH Verlag GmbH & Co. KGaA, 2005, Preface.

Duncan, R et al. Polymer-drug conjugates, PDEPT and PELT: basic principles for design and transfer from the laboratory to clinic. J Control Release. 2001, 74:135-46.

Endo et al. Nature of Linkage and Mode of Action of Methotrexate Conjugated with Antitumor Antibodies: Implications for Future Preparation of Conjugates. Cancer Research. (1988), 48, p. 3330-3335.

Fassberg, J. et al. A kinetic and mechanistic study of the hydrolysis of camptothecin and some analogues. J Pharm Sci 1992, 81:676-684.

Feng et al. Bioorg. Med. Chem. Lett. (2002) 12, pp. 3301-3303.

Greenwald, RB et al. Camptothecin-20-PEG ester transport forms: the effect of spacer groups on antineoplastic activity. Bioorg Med Chem 1998, 6:551-562.

Greenwald, RB. PEG drugs: an overview. Journal of Controlled Release 2001, 74:159-71.

International Search Report for PCT/US2004/029130, mailed Dec. 4, 2005.

Jordan, V. C. Nature Reviews: Drug Discovery, 2, 2003, p. 205-213.

Kaneda, N. et al. Metabolism and pharmacokinetics of the camptothecin analogue CPT-11 in the mouse. Cancer Research 1990, 50:1715-1720.

Li, C et al. Antitumor activity of poly(L-glutamic acid)-paclitaxel on syngeneic and xenografted tumors. Clin Cancer Res. 1999, 5:891-7.

Maeda, H et al. Conjugates of anticancer agents and polymers: advantages of macromolecular therapeutics in vivo. Bioconj. Chem. 1992, 3:351-362.

Matsumura, Y, Maeda H. A new concept for macromolecular therapeutics in cancer chemotherapy: mechanism of tumoritropic accumulation of proteins and the antitumor agent smancs. Cancer Res. 1986, 46:6387-92.

Minko, T. et al. Enhancing the anticancer efficacy of camptothecin using biotinylated poly(ethyleneglycol) conjugates in sensitive and multidrug-resistant human ovarian carcinoma cells. Cancer Chemother Pharmacol 2002, 50:143-150.

Miyasaki, K. (1975) Experimental Polymer Storage Disease in Rabbits. Virchows Arch. A. Path. Anat. And Histol., 365, 351-365.

Papisov et al. Novel EPR-independent camptothecin conjugate with dual-phase drug release: a blood pool effect? 34th Int. Symp. on Controlled Release of Bioactive Materials, Long Beach, CA, 2007, Controlled Release Society, Deerfield, IL.

Papisov et al. Pharmacokinetics of a novel camptothecin conjugate (PHF-CPT) with dual-phase drug release. Annual meeting of SNM, Washington, DC, 2007.

Papisov, M et al. Fully biodegradable hydrophilic polyals (polyacetals and polyketals). 29th Int. Symp. on Controlled Release of Bioactive Materials, 2002, Seoul, Korea. Controlled Release Society, Deerfield, IL, 2002; paper # 465.

Papisov, M. (1998) Theoretical considerations of RES-avoiding liposomes. Adv. Drug Delivery Rev., 32, 119-138.

Papisov, M. (2001) Acyclic polyacetals from polysaccharides. (Biopolymers from polysaccharides and agroproteins), ACS Symposium Series 786, pp. 301-314.

Papisov, M. et al (1996) A long-circulating polymer with hydrolizable main chain. 23-rd International Symposium on Controlled Release of Bioactive Materials, Kyoto, Japan, 1996; Controlled Release Society, Deerfield, IL,; 107-108.

Papisov, M. et al. Fully biodegradable hydrophilic polyacetals for macromolecular radiopharmaceuticals. 49-th Annual Meeting of The Society of Nuclear Medicine, Los Angeles, CA, 2002. J. Nuc. Med. Meeting Abstracts, 2002, 43:5 (Supplement) 377P.

Papisov, M. et al. Hydrophilic Polyals: Biomimetic Biodegradable Stealth Materials for Pharmacology and Bioengineering. Proceedings of 226th Natl. Meeting of American Chemical Society, New York, NY, 2003.

Papisov, MI et al. (1998) Model cooperative (multivalent) vectors for drug targeting. 25th Int. Symp. on Controlled Release of Bioactive Materials, 1998, Las Vegas, Nevada, USA; Controlled Release Society, Deerfield, IL,170-171.

Papisov, MI. Modeling in vivo transfer of long-circulating polymers (two classes of long circulating polymers and factors affecting their transfer in vivo). Adv. Drug Delivery Rev., Special issue on long circulating drugs and drug carriers, 1995, 16:127-139.

Papisov, MI. Theoretical considerations of RES-avoiding liposomes: molecular mechanics and chemistry of liposome interactions. Adv. Drug Delivery Rev. 1998, 32:119-138.

Rihova, B et al. Antibody-directed affinity therapy applied to the immune system: in vivo effectiveness and limited toxicity of daunomycin conjugated to HPMA copolymers and targeting antibody. Clin Immunol Immunopathol. 1988, 46:100-14.

Sausville et al. A Phase 1 study of the safety and tolerability of intravenous XMT-1001 in patients with advanced solid tumors, Proceedings of AACR-NCI-EORTC International Conference Molecular Targets and Cancer Therapeutics, 2007 (Apr. 2007) abstr 146.

Sausville et al. A Phase I study of the safety and pharmacokinetics (PK) of XMT-1001 given as an intravenous (IV) infusion once every three weeks to patients with advanced solid tumors, J Clin Oncol 27: 15s, 2009 (suppl; abstr 2574).

Sausville et al. Phase 1 Study of XMT-1001, a novel water soluable camptothecin conjugate, given as an intravenous infusion once every three weeks to patients with advanced solid tumors, Proceedings of AACR-NCI-EORTC International Conference Molecular Targets and Cancer Therapeutics, (Apr. 2007); abstr 09-A-169.

Schoemaker, NE. et al. A phase I and pharmacokinetic study of MAG-CPT, a water-soluble polymer conjugate of camptothecin. British Journal of Cancer 2002, 87:608-614.

Tadayoni, BM et al. Synthesis, in vitro kinetics, and in vivo studies on protein conjugates of AZT: evaluation as a transport system to increase brain delivery. Bioconjugate Chemistry 1993, 4:139-145.

Tomlinson et al. Polyacetal-doxorubicin conjugates designed for pH dependent degradation. Bioconjugate Chem., 2003, 14(6), 1096-1106.

Ulbrich, K et al. HPMA copolymers with pH-controlled release of doxorubicin. In vitro cytotoxicity and in vivo antitumor activity. J Control Release. 2003, 87:33-47.

Wall, ME et al. Plant antitumor agents. I. The isolation and structure of Camptothecin, a novel alkaloidal leukemia and tumor inhibitor from *Camptothecia acuminata*. J. Am. Chem. Soc.1966, 88, 3888-3890.

Webb II, R.R. et al. Synthesis of 1-(aminooxy)-4-[(3-nitro-2-pyridyl)dithio]butane hydrochloride and of 1-(aminooxy)-4-[(3-nitro-2-pyridyl)dithio]but-2-ene. Novel heterofunctional cross-linking reagents, Bioconjugate Chem. 1990, 1: 96-99.

Yurkovetskiy et al. XMT-1001, a novel polymeric camptothecin prodrug in clinical development for patients with advanced cancer, Adv. Drug Deliv. Rev. (2009) in press.

Yurkovetskiy et al. XMT-1001, a novel polymeric prodrug of camptothecin, is a potent inhibitor of LS174 and A2780 human tumor xenografts on a mouse model, Proc. Am. Assoc. Cancer Res. 2007 (Apr. 2007) abstr 781.

Yurkovetskiy, A. et al. Biodegradable polyal carriers for protein modification. 29th Int. Symp. on Controlled Release of Bioactive Materials, 2002, Seoul, Korea. Controlled Release Society, Deerfield, IL, 2002; paper # 357.

Yurkovetskiy, A. et al. Biodegradable polyals for protein modification. Controlled Release Society's Winter Symposium, Salt Lake City, Utah, 2003.

Yurkovetskiy, A. et al. Synthesis of a macromolecular camptothecin conjugate with dual phase drug release. Molecular Pharmaceutics, 2004, 1:375-382.

Yurkovetsky, A. et al., Fully Degradable Hydrophilic Polyals for Protein Modification. Biomacromolecules 2005, 6, 2648-2658.

Zalipsky et al. Eur. Polym. J. (1983), vol. 19, No. 12, p. 1177-1183.

Zhao, H. et al. 20-O-acylcamptothecin derivatives: evidence for lactone stabilization. Journal of Organic Chemistry 2000, 65:4601-4606.

Yurkovetskiy et al. Camptothecin conjugate with dual phase drug release mechanism. 31st Annual Meeting and Exposition of the Controlled Release Society Transaction CD-Rom—Jun. 12-16 2004 Honolulu, Hawaii, U.S.A. abstr 144.

Bruneel D. et al. "Chemical modification of pullulan: 3. Succinoylation" Polymer, Elsevier Science Publishers B.V, GB, vol. 35, No. 12, Jun. 1, 1994, pp. 2656-2658, XP024117544 ISSN: 0032-3861.

Cervigni S. et al. "Synthesis of Glcopeptides and Lipopeptides by Chemoselective Ligation" Angew. Chem. Int. Ed. Egl. 1996, 35, No. 11, pp. 1230-1232.

Conover, C. et al. Physiological Effect of Polyethylene Glycol Conjugation on Stroma-Free Bovine Hemoglobin in the Conscious Dog After Partial Exchange Transfusion, Artificial Organs, vol. 21, No. 5, 1997, pp. 369-378.

Gao Q. et al. "Drug-induced DNA repair: X-ray structure of a DNA-ditercalinium complex" Proc. Natl. Acad. Sci. USA vol. 88, pp. 2422-2426, March 1991 Biochemistry.

Hermanson G. Bioconjugate Techniques pp. 548-569, (1996).

Matysiak S. "Acetal Oligonucleotide Conjugates in Antisense Strategy" Nucleosides & Nucleotides, 16(5&6), pp. 855-861 (1997).

Papisov M.I. et al. "Semisynthetic Hyrophilic Polyals" Biomacromolecules 2005, vol. 6, pp. 2659-2670.

Bissett, D. et al. Phase I and pharmacokinetic (PK) study of MAG-CPT (PNU 166148): a polymeric derivative of camptothecin (CPT). British Journal of Cancer (2004) 91, pp. 50-55.

Daud, A. et al. Phase I trial of CT-2106 (polyglutamated camptothecin) administered weekly in patients (pts) with advanced solid tumors. Journal of Clinical Oncology, 2006 ASCO Annual Meeting Proceedings Part I. vol. 24, No. 18S (Jun. 20 Supplement), 2006: Abstract No. 2015.

Deshmukh, M. A Series of α-Amino Acid Ester Prodrugs of Camptothecin: In Vitro Hydrolysis and A549 Human Lung Carcinoma Cell Cytotoxity. J. Med. Chem. 2010, 53, pp. 1038-1047.

Rowinsky et al. A Phase I and Pharmacokinetic Study of Pegylated Camptothecin as a 1-Hour Infusion Every 3 Weeks in Patients With Advanced Solid Malignancies. Journal of Clinical Oncology, vol. 21, No. 1, 2003 pp. 148-157.

Sausville et al. A Phase 1 study of XMT-1001, a novel water soluble camptothecin conjugate, given as an intraveneous infusion once every three weeks to patients with advanced solid tumors, Proceedings of AACR-NCI-EORTC International Conference Molecular Targets and Cancer Therapeutics, (Nov. 2009) abstr B52.

Song, L. et al. Kinetics and Mechanisms of Activation of α-Amino Acid Ester Prodrugs of Camptothecins. J. Med. Chem. 2006, 49, pp. 4344-4355.

Veltkamp, S. et al. Clinical and Pharmacologic Study of the Novel Prodrug Delimotecan (MEN 4901/T-0128) in Patients with Solid Tumors. Clin Cancer Res 2008; 14(22) Nov. 15, 2008 pp. 7535-7544.

Duncan, R. Polymer-Drug Conjugates. In: Handbook of Anticancer Drug Development, D. Budman, H. Calvert, and E. Rowinsky (Eds.), Lippincott, Williams & Wilkins Philadelphia (2003) pp. 239-260.

Hreczuk-Hirst et al. Dextrins as Carriers for Drug Targeting: Reproducible Succinoylation as a Means to Introduce Pendant Groups. Journal of Bioactive and Compatible Polymers. vol. 16 (2001) 353-365.

Hreczuk-Hirst et al. Dextrins as potential carriers for drug targeting: tailored rates of dextrin degradation by introduction of pendant groups. International Journal of Pharmaceutics. 230 (2001) 57-66.

* cited by examiner

DUAL PHASE DRUG RELEASE SYSTEM

PRIORITY INFORMATION

The present Application claims the benefit under 35 U.S.C. §371 of International Application No.: PCT/US2004/029130 (published PCT application No. WO 05/023294), filed Sep. 4, 2004, which claims priority to U.S. patent application Ser. No. 60/500,571 filed Sep. 5, 2003, the entire contents of the above applications are incorporated herein by reference.

GOVERNMENT FUNDING

The present invention was made with U.S. government support under grants R21-RR14221 and T32 GM07035) awarded by the National Center for Research Resources of the National Institutes of Health. Accordingly, the United States Government has certain rights in this invention.

BACKGROUND OF THE INVENTION

Traditionally, pharmaceuticals have primarily consisted of small molecules that are dispensed orally (as solid pills and liquids) or as injectables. Over the past three decades, formulations (i.e., compositions that control the route and/or rate of drug delivery and allow delivery of the therapeutic agent at the site where it is needed) have become increasingly common and complex. Nevertheless, many questions and challenges regarding the development of new treatments as well as the mechanisms with which to administer them remain to be addressed.

Although considerable research efforts in this area have led to significant advances, drug delivery methods/systems that have been developed over the years and are currently used, still exhibit specific problems that require improvement. For example, many drugs exhibit limited or otherwise reduced potencies and therapeutic effects because they are either generally subject to partial degradation before they reach a desired target in the body, or accumulate in tissues other than the target, or both.

One objective in the field of drug delivery systems, therefore, is to deliver medications intact to specifically targeted areas of the body through a system that can stabilize the drug and control the in vivo transfer of the therapeutic agent utilizing either physiological or chemical mechanisms, or both. Over the past decade, materials such as polymeric microspheres, polymer micelles, soluble polymers and hydrogel-type materials have been shown to be effective in enhancing drug stability in vitro and in vivo, release dynamics, targeting specificity, lowering systemic drug toxicity, and thus have shown great potential for use in biomedical applications, particularly as components of various formulations and drug delivery devices.

Therefore a need exists in the biomedical field for low-toxicity, biodegradable, biocompatible, hydrophilic polymer conjugates comprising pharmaceutically useful modifiers, which overcome or minimize the above-referenced problems. Such polymer conjugates would find use in several applications, including therapeutic and diagnostic pharmaceutical formulations, gene vectors, medical devices, implants, and other therapeutic, diagnostic and prophylatic agents.

The design and engineering of biomedical polymers (e.g., polymers for use under physiological conditions) are generally subject to specific and stringent requirements. In particular, such polymeric materials must be compatible with the biological milieu in which they will be used, which often means that they show certain characteristics of hydrophilicity. In several applications, they also have to demonstrate adequate biodegradability (i.e., they degrade to low molecular weight species. The polymer fragments are in turn metabolized in the body or excreted,).

Biodegradability is typically accomplished by synthesizing or using polymers that have hydrolytically unstable linkages in the backbone. The most common chemical backbone components with this characteristic are esters and amides. Most recently, novel polymers have been developed with anhydride, orthoester, polyacetal, polyketal and other biodegradable backbone components. Hydrolysis of the backbone structure is the prevailing mechanism for the degradation of such polymers. Other polymer types, such as polyethers, may degrade through intra- or extracellular oxidation. Biodegradable polymers can be either natural or synthetic. Synthetic polymers commonly used in medical applications and biomedical research include polyethyleneglycol (pharmacokinetics and immune response modifier), polyvinyl alcohol (drug carrier), and poly(hydroxypropylmethacrylamide) (drug carrier). In addition, natural polymers are also used in biomedical applications. For instance, dextran, hydroxyethylstarch, albumin, polyaminoacids and partially hydrolyzed proteins find use in applications ranging from plasma expanders, to radiopharmaceuticals to parenteral nutrition. In general, synthetic polymers may offer greater advantages than natural materials in that they can be tailored to give a wider range of properties and more predictable lot-to-lot uniformity than can materials from most natural sources. Methods of preparing various polymeric materials are well known in the art. In many biomedical applications, polymer molecules should be chemically associated with the drug substance, or other modifiers, or with each other (e.g., forming a gel). Several properties of the final product depend on the character of association, for example, drug release profile, immunotoxicity, immunogenicity and pharmacokinetics. Therefore a need exists for methods of polymer association with drug substances and other pharmaceutically useful modifiers that would be compatible with the biomedical use of the associates (conjugates, gels). Such methods should further allow, where necessary, drug release in under physiological conditions with an optimal rate and in a chemical form or forms optimally suited for the intended application.

SUMMARY OF THE INVENTION

The present invention discloses a polymer conjugate that is biodegradable, biocompatible and exhibits little toxicity and/or bioadhesivity in vivo, and contains one or more modifiers covalently attached to the polymer via optionally substituted succinamide-containing linkages.

In one aspect, the invention encompasses a conjugate comprising a carrier substituted with one or more occurrences of a moiety having the structure:

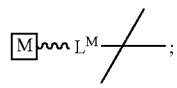

wherein each occurrence of M is independently a modifier having a molecular weight $\leq 10$ kDa;
∿∿∿denotes direct of indirect attachment of M to linker $L^M$; and
each occurrence of $L^M$ is independently an optionally substituted succinamide-containing linker, whereby the modifier M is directly or indirectly attached to the succinamide linker through an amide bond, and the carrier is linked directly or indirectly to each occurrence of the succinamide linker through an ester bond.

In another aspect, the invention provides compositions comprising the conjugates, methods for their preparation, and methods of use thereof in the treatment of various disorders, including, but not limited to cancer.

Definitions

Certain compounds of the present invention, and definitions of specific functional groups are also described in more detail herein. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

"Protecting group": as used herein, the term protecting group means that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. Nitrogen protecting groups, as well as protection and deprotection methods are known in the art. Guidance may be found in "Protective Groups in Organic Synthesis" Third Ed. Greene, T. W. and Wuts, P. G., Eds., John Wiley & Sons, New York: 1999, the entire contents of which are hereby incorporated by reference. In certain exemplary embodiments, $R^{N1}$ and $R^{N2}$ are each hydrogen. Nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

"Biocompatible": The term "biocompatible", as used herein is intended to describe compounds that exert minimal destructive or host response effects while in contact with body fluids or living cells or tissues. Thus a biocompatible group, as used herein, refers to an aliphatic, alicyclic, heteroaliphatic, heteroalicyclic, aryl or heteroaryl moiety, which falls within the definition of the term biocompatible, as defined above and herein. The term "Biocompatibility" as used herein, is also taken to mean minimal interactions with recognition proteins, e.g., naturally occurring antibodies, cell proteins, cells and other components of biological systems, unless such interactions are specifically desirable. Thus, substances and functional groups specifically intended to cause the above effects, e.g., drugs and prodrugs, are considered to be biocompatible. Preferably (with exception of compounds intended to be cyclotoxic, such as e.g. antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity or other such adverse effects. In the above sentence, the term "normal cells" refers to cells that are not intended to be destroyed or otherwise significantly affected by the compound being tested.

"Biodegradable": As used herein, "biodegradable" polymers are polymers that are susceptible to biological processing in vivo. As used herein, "biodegradable" compounds are those that, when taken up by cells, can be broken down by the lysosomal or other chemical machinery or by hydrolysis into components that the cells can either reuse or dispose of without significant toxic effect on the cells. The degradation fragments preferably induce no or little organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the polymer backbones of various conjugates, for example, include exposure of the biodegradable conjugates to water at a temperature and a pH of lysosomal intracellular compartment. Biodegradation of some conjugate backbones, e.g. polyal conjugates of the present invention, can also be enhanced extracellularly, e.g. in low pH regions of the animal body, e.g. an inflamed area, in the close vicinity of activated macrophages or other cells releasing degradation facilitating factors. In certain preferred embodiments, the effective size of the polymer molecule at pH~7.5 does not detectably change over 1 to 7 days, and remains within 50% of the original polymer size for at least several weeks. At pH~5, on the other hand, the polymer preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Hydrophilic": The term "hydrophilic" as it relates to substituents on the polymer monomeric units does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, alicyclic, heteroaliphatic, heteroalicyclic, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In preferred embodiments of the present invention, at least one of the polymer monomeric units include a carboxyl group (COOH), an aldehyde group (CHO), a methylol ($CH_2OH$) or a glycol (for example, $CHOH—CH_2OH$ or $CH—(CH_2OH)_2$).

"Hydrophilic": The term "hydrophilic" as it relates to the polymers of the invention generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) which belong to classes of chemical compounds, whether naturally-occurring or artificially created (e.g., by synthetic or recombinant methods), that are commonly found in cells and tissues. Exemplary types of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Carrier": The term carrier, as used herein, refers to any small or large molecule, biomolecule, particle, gel or other object or material which is or can be covalently attached to one or more drug molecules with a succinamide linker.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxyaldehydes or polyhydroxyketones, or change to such substances on simple chemical transformations, such as hydrolysis, oxydation or reduction. Typically, carbohydrates are present in the form of cyclic acetals or ketals (such as, glucose or fructose). These cyclic units (monosaccharides) may be connected to each other to form molecules with few (oligosaccharides) or several (polysaccharides) monosaccharide units. Often, carbohydrates with well defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or derivatives of naturally occurring sugars (e.g., 2'-fluororibose, 2'-deoxyribose, and hexose).

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. Typically, small molecules have a molecular weight of less than about 1500 Da (1500 g/mol). In certain preferred embodiments, the small molecule is a drug and the small molecule is referred to as "drug molecule" or "drug". In certain embodiment, the drug molecule has MW smaller or equal to about 10 kDa. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered suitable for use with the present hydrophilic polymers.

Classes of drug molecules that can be used in the practice of the present invention include, but are not limited to, anti-cancer substances, radionuclides, vitamins, anti-AIDS substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs.

A more complete, although not exhaustive, listing of classes and specific drugs suitable for use in the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference.

"Pharmaceutically useful group or entity": As used herein, the term Pharmaceutically useful group or entity refers to a compound or fragment thereof, or a chemical moiety which, when associated with the conjugates of the present invention, can exert some biological or diagnostic function or activity when administered to a subject, or enhance the therapeutic, diagnostic or preventive properties of the conjugates in biomedical applications, or improve safety, alter biodegradation or excretion, or is detectable. Examples of suitable pharmaceutically useful groups or entities include hydrophilicity/hydrophobicity modifiers, pharmacokinetic modifiers, biologically active modifiers, detectable modifiers.

"Modifier": As used herein, the term modifier refers to an organic, inorganic or bioorganic moiety that is covalently incorporated into a carrier. Modifiers can be small molecules or macromolecules, and can belong to any chemical or pharmaceutical class, e.g., nucleotides, chemotherapeutic agents, antibacterial agents, antiviral agents, immunomodulators, hormones or analogs thereof, enzymes, inhibitors, alkaloids and therapeutic radionuclides a therapeutic radionuclide (e.g., alpha, beta or positron emitter). In certain embodiments, chemotherapeutic agents include, but are not limited to, topoisomerase I and II inhibitors, alkylating agents, anthracyclines, doxorubicin, cisplastin, carboplatin, vincristine, mitromycine, taxol, camptothecin, antisense oligonucleotides, ribozymes, and dactinomycines. In certain embodiments, modifiers according to the invention include, but are not limited to, biomolecules, small molecules, therapeutic agents, pharmaceutically useful groups or entities, macromolecules, diagnostic labels, chelating agents, hydrophilic moieties, dispersants, charge modifying agents, viscosity modifying agents, surfactants, coagulation agents and flocculants, to name a few. A modifier can have one or more pharmaceutical functions, e.g., biological activity and pharmacokinetics modification. Pharmacokinetics modifiers can include, for example, antibodies, antigens, receptor ligands, hydrophilic, hydrophobic or charged groups. Biologically active modifiers include, for example, therapeutic drugs and prodrugs, antigens, immunomodulators. Detectable modifiers include diagnostic labels, such as radioactive, fluorescent, paramagnetic, superparamagnetic, ferromagnetic, X-ray modulating, X-ray-opaque, ultrasound-reflective, and other substances detectable by one of available clinical or laboratory methods, e.g., scintigraphy, NMR spectroscopy, MRI, X-ray tomography, sonotomography, photoimaging, radioimmunoassay. Viral and non-viral gene vectors are considered to be modifiers.

"Macromolecule": As used herein, the term macromolecule refers to molecules, whether naturally-occurring or artificially created (e.g., via chemical synthesis) that have a relatively high molecular weight, generally above 1500 g/mole Preferred macromolecules are biologically active in that they exert a biological function in animals, preferably mammals, more preferably humans. Examples of macromolecules include proteins, enzymes, growth factors, cytokines, peptides, polypeptides, polylysine, proteins, lipids, polyelectrolytes, immunoglobulins, DNA, RNA, ribozymes, plasmids, and lectins. For the purpose of this invention, supramolecular constructs such as viruses, nucleic acid helices and protein associates (e.g., dimers) are considered to be macromolecules. When associated with the conjugates of the invention, a macromolecule may be chemically modified prior to being associated with said biodegradable biocompatible conjugate.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a conjugate of the present invention, such diagnostic labels permit the monitoring of the conjugate in vivo. Alternatively or additionally, constructs and compositions that include diagnostic labels can be used to monitor biological functions or structures. Examples of diagnostic labels include, without limitation, labels that can be used in medical diagnostic procedures, such as, radioactive isotopes (radionuclides) for gamma scintigraphy and Positron Emission Tomography (PET), contrast agents for Magnetic Resonance Imaging (MRI) (for example paramagnetic atoms and superparamagnetic nanocrystals), contrast agents for computed tomography and other X-ray-based imaging methods, agents for ultrasound-based diagnostic methods (sonography), agents for neutron activation (e.g., boron, gadolinium), fluorophores for various optical procedures, and, in general moieties which can emit, reflect, absorb, scatter or otherwise affect electromagnetic fields or waves (e.g. gamma-rays, X-rays, radiowaves, microwaves, light), particles (e.g. alpha particles, electrons, positrons, neutrons, protons) or other forms of radiation, e.g. ultrasound.

"Efficient amount of a glycol-specific oxidizing agent": as it relates to the oxidative cleavage of the polysaccharides referred to in the present invention, the phrase efficient amount of a glycol-specific oxidizing agent means an amount of the glycol-specific oxidizing agent that provides oxidative opening of essentially all carbohydrate rings of a polysaccharide.

"Protected hydrophilic group" and "Protected organic moiety" as these terms are used herein, mean a chemical group which will not interfere with a chemical reaction that the carrier or carrier conjugate is subjected to. Examples of protected hydrophilic groups include carboxylic esters, alkoxy groups, thioesters, thioethers, vinyl groups, haloalkyl groups, Fmoc-alcohols, etc.

"Aliphatic": In general, the term aliphatic, as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

"Alkenyl": the term alkenyl denotes a monovalent group derived from a hydrocarbon moiety having at least one carbon-carbon double bond by the removal of a single hydrogen atom, which alkenyl groups are optionally substituted with one or more functional groups. Substituents include, but are not limited to, any of the substituents mentioned below, i.e., the substituents recited below resulting in the formation of a stable compound. Alkenyl groups include, for example, ethenyl, propenyl, butenyl, 1-methyl-2-buten-1-yl, and the like.

"Alkynyl": the term alynyl as used herein refers to a monovalent group derived form a hydrocarbon having at least one carbon-carbon triple bond by the removal of a single hydrogen atom, which alkenyl groups are optionally substituted. Substituents include, but are not limited to, any of the substituents mentioned below, i.e., the substituents recited below resulting in the formation of a stable compound. Representative alkynyl groups include ethynyl, 2-propynyl (propargyl), 1-propynyl, and the like.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substitutents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

"Alicyclic": as used herein, the term alicyclic refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substitutents.

"Cycloalkyl": as used herein, the term cycloalkyl refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

"Heteroaliphatic": as used herein, the term heteroaliphatic refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;—or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$), —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substitutents are illustrated by the specific embodiments shown in the Examples that are described herein.

"Heteroalicyclic", "heterocycloalkyl" or "heterocyclic": The term heteroalicyclic, heterocycloalkyl or heterocyclic, as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6-, 7- or 8-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. In certain embodiments, "heteroalicyclic", "heterocycloalkyl" or "heterocyclic" refers to a partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;—or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples or generally applicable substitutents are illustrated by the specific embodiments shown in the Examples, which are described herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

"Aromatic moiety": as used herein, the term aromatic moiety refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

"Heteroaromatic moiety": as used herein, the term heteroaromatic moiety refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -alkyl)aromatic, -(heteroalkyl)aromatic, (heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

"Aryl": as used herein, the term aryl refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

"Heteroaryl": as used herein, the term heteroaryl refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

"Alkoxy" (or "alkyloxy"): as used herein, the term alkoxy (or alkyloxy) refers to an alkyl group, as previously defined, attached to the parent molecular moiety through an oxygen atom ("alkoxy"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy.

"Amine": the term amine refers to a group having the structure —$N(R)_2$ wherein each occurrence of R is independently hydrogen, or an aliphatic, heteroaliphatic, aromatic or heteroaromatic moiety, or the R groups, taken together, may form a heterocyclic moiety. In certain instances, an amine group can be charged (protonized) or quarternized, e.g., —$HN^+(R)_2$ or —$N^+(R)_3$.

"Alkylamino": as used herein, the term alkylamino refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

"Carboxylic acid": The term carboxylic acid as used herein refers to a compound comprising a group of formula —$CO_2H$.

"Halo, halide and halogen": The terms halo, halide and halogen as used herein refer to an atom selected from fluorine, chlorine, bromine, and iodine.

"Methylol": The term methylol as used herein refers to an alcohol group of the structure —$CH_2OH$.

"Hydroxyalkyl": As used herein, the term hydroxyalkyl refers to an alkyl group, as defined above, bearing at least one OH group.

"Mercaptoalkyl": The term mercaptoalkyl as used therein refers to an alkyl group, as defined above, bearing at least one SH group "Acyl": The term acyl, as used herein, refers to a group comprising a carbonyl group of the formula C=O. Examples of acyl groups include acyl halides, anhydrides, thioesters, amides and carboxylic esters.

"Hydrocarbon": The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

"Substituted": The terms substituted, whether preceded by the term "optionally" or not, and substitutent, as used herein, refers to the replacement of hydrogen radicals in a given structure with the radical of a specified substitutent. When more than one position in any given structure may be substituted with more than one substitutent selected from a specified group, the substitutent may be either the same or different at every position. As used herein, the term "substituted" is contemplated to include all permissible substitutents of organic compounds. In a broad aspect, the permissible substitutents include acyclic and cyclic, branched and unbranched, carbocyclic and heterocyclic, aromatic and nonaromatic substitutents of organic compounds. Heteroatoms such as nitrogen may have hydrogen substitutents and/or any permissible substitutents of organic compounds described herein which satisfy the valencies of the heteroatoms. Examples of substitutents include, but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC (=O)NR$^{G2}$, —NR$^{G2}$C(=O)O—, —NR$^{G2}$C(=O)NR$^{G2}$, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substitutents are illustrated by the specific embodiments shown in the Examples that are described herein.

"Succinamide linker" or "Succinamide": unless otherwise specified, as used herein, the term succinamide linker or succinamide designates a linker having the structure:

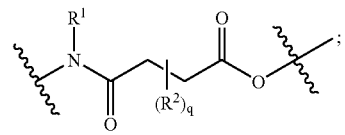

wherein q is an integer from 0-4; R$^1$ is hydrogen or a nitrogen protecting group; and each occurrence of R$^2$ is independently hydrogen, halogen, —CN, NO$_2$, an aliphatic, alicyclic, heteroaliphatic, heterocyclic, aryl, heteroaryl, aromatic, heteroaromatic moiety, or —GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ is independently hydrogen, halogen, or an optionally substituted aliphatic, heteroaliphatic, alicyclic, heteroalicyclic, aromatic, heteroaromatic, aryl or heteroaryl moiety. In certain embodiments,

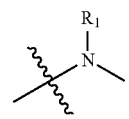

designates the site of attachment of a modifier M, which is directly or indirectly attached to the succinamide moiety through an amide bond. In certain embodiments,

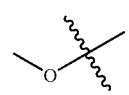

designates the site of attachment of a carrier, which is linked directly or indirectly to the succinamide moiety through an ester bond.

"Succinimide": unless otherwise specified, as used herein, the term succinimide designates a moiety having the structure:

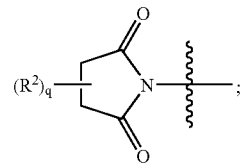

wherein q is an integer from 0-4; and each occurrence of R$^2$ is independently hydrogen, halogen, —CN, NO$_2$, an aliphatic, alicyclic, heteroaliphatic, heterocyclic, aryl, heteroaryl, aromatic, heteroaromatic moiety, or -GR$^{G1}$ wherein G is —O—, —S—, —NR$^{G2}$—, —C(=O)—, —S(=O)—, —SO₂—, —C(=O)O—, —C(=O)NR^G2—, —OC(=O)—, —NR^G2C(=O)—, —OC(=O)O—, —OC(=O)NR^G2—, —NR^G2C(=O)O—, —NR^G2C(=O)NR^G2—, —C(=S)—, —C(=S)S—, —SC(=S)—, —SC(=S)S—, —C(=NR^G2)—, —C(=NR^G2)O—, —C(NR^G2)NR^G3—, —OC(=NR^G2)—, —NR^G2C(=NR^G3)—, —NR^G2SO₂—, —NR^G2SO₂NR^G3—, or —SO₂NR^G2—, wherein each occurrence of R^G1, R^G2 and R^G3 is independently hydrogen, halogen, or an optionally substituted aliphatic, heteroaliphatic, alicyclic, heteroalicyclic, aromatic, heteroaromatic, aryl or heteroaryl moiety.

The following are more general terms used throughout the present application:

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone. The term "subject" encompasses animals.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, or combinations thereof, etc.

"Efficient amount": In general, as it refers to an active agent or drug delivery device, the term "efficient amount" refers to the amount necessary to elicit the desired biological response. As will be appreciated by those of ordinary skill in this art, the efficient amount of an agent or device may vary depending on such factors as the desired biological endpoint, the agent to be delivered, the composition of the encapsulating matrix, the target tissue, etc. For example, the efficient amount of microparticles containing an antigen to be delivered to immunize an individual is the amount that results in an immune response sufficient to prevent infection with an organism having the administered antigen.

"Directly attached": as used herein, the term directly attached, as it refers to covalent attachment of one entity to another (e.g., a modifier attached to a succinamide linker) means that the two entities are connected via a covalent bond. For example, the present document describes modifiers attached to succinamide linkers, whereby the point of attachment to the succinamide linker is an amide bond. A suitable modifier might be any modifier comprising an amine functionality (or protected form thereof), which forms an amide bond upon reaction with the carboxylic acid group of a suitable succinic acid linker.

"Indirectly attached": as used herein, the term indirectly attached, as it refers to covalent attachment of one entity to another (e.g., a modifier attached to a succinamide linker) means that the two entities are connected via a linking moiety (as opposed to a direct covalent bond). For example, the present document describes modifiers attached to succinamide linkers, whereby the point of attachment to the succinamide linker is an amide bond. A suitable modifier might be any modifier comprising a functionality, which may be "capped" with a chemical moiety comprising an amine group; or protected form thereof, such that the amine-capped modifier may now form an amide bond upon reaction with the carboxylic acid group of a suitable succinic acid linker.

"Natural amino acyl residue": The term natural amino acyl residue as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

"Unnatural amino acyl residue": The term unnatural amino acyl residue as used herein refers to any amino acid which is not a natural amino acid. This includes, for example, α-, β-, ω-, D-, L-amino acyl residues, and compounds of the general formula

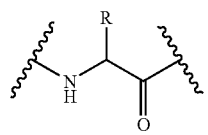

wherein the side chain R is other than the amino acid side chains occurring in nature.

"Amino acyl": More generally, the term amino acyl, as used herein, encompasses natural amino acid and unnatural amino acids.

"PHF" refers to poly(1-hydroxymethylethylene hydroxymethyl-formal).

"CPT" refers to camptothecin.

DETAILED DESCRIPTION OF CERTAIN PREFERRED EMBODIMENTS OF THE INVENTION

Figure 1:
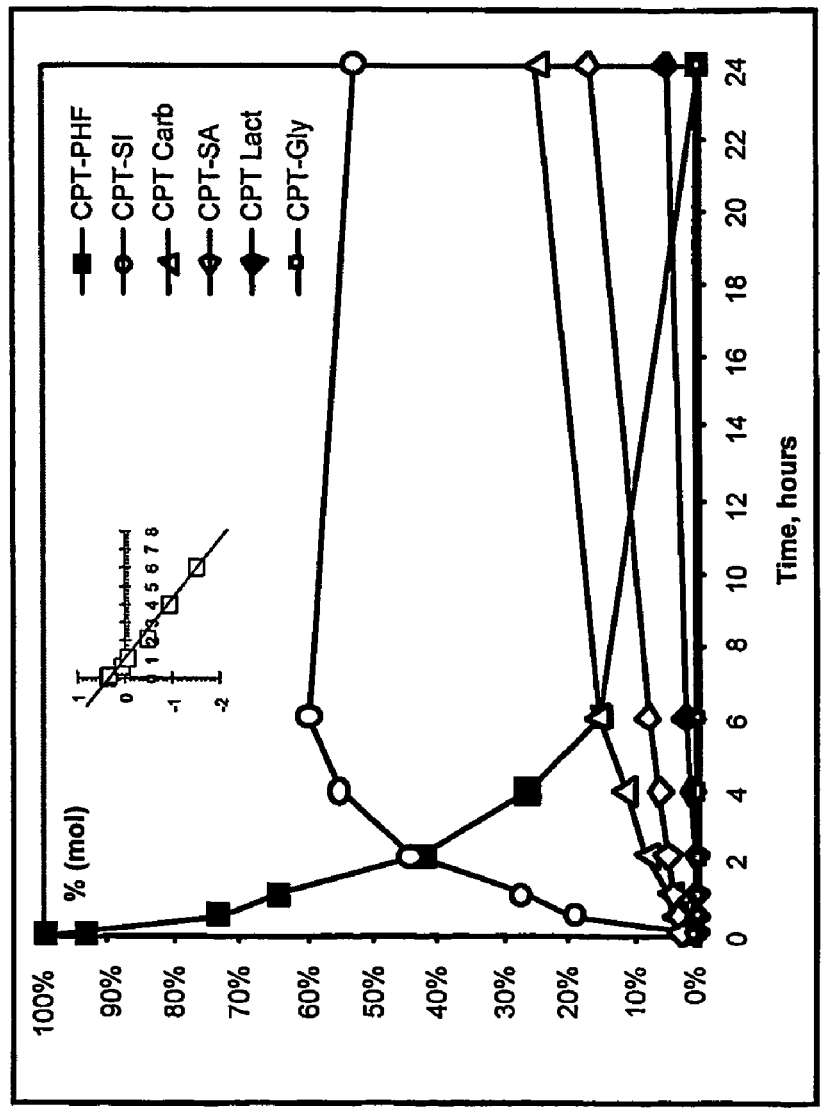
FIG. 1 depicts an exemplary prodrug release experiment from PHF-CPT in rat plasma at 37° C. Insert: log linearization of PHF-CPT kinetics. Mean values from two independent experiments, for all points SD<10% of the mean, p<0.05.
Figure 2:
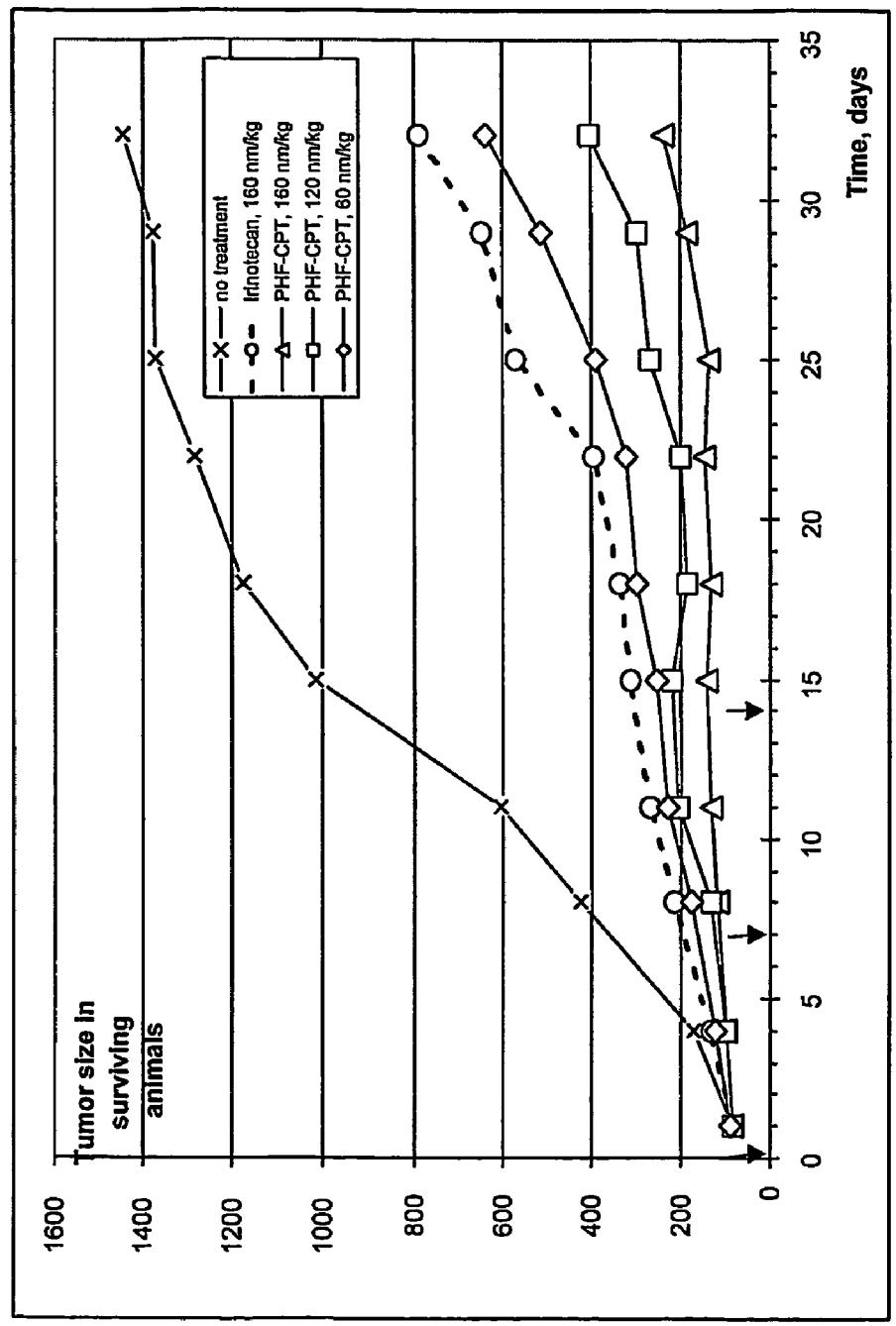
FIG. 2 depicts an exemplary tumor size dynamics study in nude mice with LS174t xenografts. Arrows: drug injections (qwx3). Note that even the smallest conjugate dose is more active than Irinotecan control. Statistics: n=710 per group, standard deviations within 25% of mean; not shown for Figure clarity.

Certain preferred embodiments of the invention will now be more particularly described and pointed out in the claims. It will be understood that the particular embodiments of the invention are shown by way of illustration and not as limitations of the invention. Principle features of the invention may be employed in various embodiments without departing from the spirit and scope of the invention.

Addressing the need for non-bioadhesive, fully biodegradable soluble polymer conjugates for use in biomedical applications, in one aspect, the present invention provides novel carrier conjugates, whereby the carrier is chemically modified by covalent attachment of small/large (bio)molecules or other (in)organic moieties (i.e., modifiers) via optionally substituted monosuccinamide-containing linkages.

Thus, in certain embodiments, the invention provides a conjugate comprising a carrier substituted with one or more occurrences of a moiety having the structure:

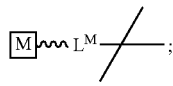

wherein each occurrence of M is independently a modifier;
∼∼∼denotes direct of indirect attachment of M to linker $L^M$; and
each occurrence of $L^M$ is independently an optionally substituted succinamide-containing linker, whereby the modifier M is directly or indirectly attached to the succinamide linker through an amide bond, and the carrier is linked directly or indirectly to each occurrence of the succinamide linker through an ester bond.

In certain embodiments, each occurrence of $L^M$ independently comprises a moiety having the structure:

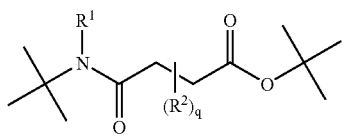

wherein

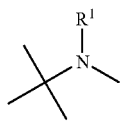

denotes the site of attachment to the modifier M;

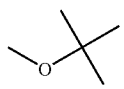

denotes the site of attachment to the carrier; q is an integer from 0-4; $R^1$ is hydrogen, —C(=O)$R^{1A}$, —C(=O)O$R^{1A}$, —S$R^{1A}$, SO$_2R^{1A}$ or an aliphatic, alicyclic, heteroaliphatic, heterocyclic, aryl, heteroaryl, aromatic, heteroaromatic moiety, wherein each occurrence of $R^{1A}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aromatic, heteroaromatic, aryl or heteroaryl; and each occurrence of $R^2$ is independently hydrogen, halogen, —CN, NO$_2$, an aliphatic, alicyclic, heteroaliphatic, heterocyclic, aryl, heteroaryl, aromatic, heteroaromatic moiety, or —G$R^{G1}$ wherein G is —O—, —S—, —N$R^{G2}$—, —C(=O)—, —S(=O)—, —SO$_2$—, —C(=O)O—, —C(=O)N$R^{G2}$—, —OC(=O)—, —N$R^{G2}$C(=O)—, —OC(=O)O—, —OC(=O)N$R^{G2}$—, —N$R^{G2}$C(=O)O—, —N$R^{G2}$C(=O)N$R^{G2}$—, —C(=S)—, —C(=S)S—, —SC(=S)—, —SC(=S)S—, —C(=N$R^{G2}$)—, —C(=N$R^{G2}$)O—, —C(=N$R^{G2}$)N$R^{G3}$—, —OC(=N$R^{G2}$)—, —N$R^{G2}$C(=N$R^{G3}$)—, —N$R^{G2}$SO$_2$—, —N$R^{G2}$SO$_2$N$R^{G3}$—, or —SO$_2$N$R^{G2}$—, wherein each occurrence of $R^{G1}$, $R^{G2}$ and $R^{G3}$ is independently hydrogen, halogen, or an optionally substituted aliphatic, heteroaliphatic, alicyclic, heteroalicyclic, aromatic, heteroaromatic, aryl or heteroaryl moiety.

In certain embodiments, $R^1$ is hydrogen or alkyl, alkenyl, —C(=O)$R^{1A}$, —C(=O)O$R^{1A}$, —S$R^{1A}$, SO$_2R^{1A}$; wherein each occurrence of $R^{1A}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aromatic, heteroaromatic, aryl, heteroaryl —C(=O)$R^{1B}$ or —G$R^{1G}$, wherein G is —O—, —S—, —N$R^{1G}$, wherein each occurrence of $R^{1B}$ and $R^{1G}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, $R^1$ is hydrogen.

In certain embodiments, each occurrence of $R^2$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aromatic, heteroaromatic, aryl, heteroaryl, —C(=O)$R^{2A}$ or —Z$R^{2A}$, wherein Z is —O—, —S—, —N$R^{2B}$, wherein each occurrence of $R^{2A}$ and $R^{2B}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, each occurrence of $R^2$ is hydrogen. In certain embodiments, one or more occurrences of $R^2$ is $C_{1-10}$alkyl. In certain embodiments, one or more occurrences of $R^2$ is lower alkyl. In certain embodiment, one or more occurrences of $R^2$ is a hydrophobic group. In certain embodiment, one or more occurrences of $R^2$ is a hydrophilic group. In certain embodiment, one or more occurrences of $R^2$ is an anionic group. In certain embodiment, one or more occurrences of $R^2$ is a cationic group. In certain embodiment, one or more occurrences of $R^2$ is a receptor ligand.

In certain embodiments, conjugates of the present invention have the general structure:

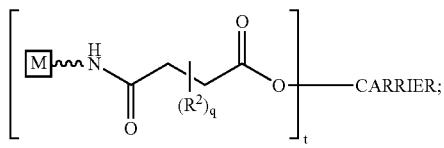

wherein $R^2$ and q are as defined above, ⁓⁓denotes direct of indirect attachment of M to the succinamide linker; and t is an integer designating the number of modifier moieties conjugated to the carrier.

Such conjugates feature dual phase release of the modifier moieties (M), as depicted in Scheme 1 below:

Scheme 1

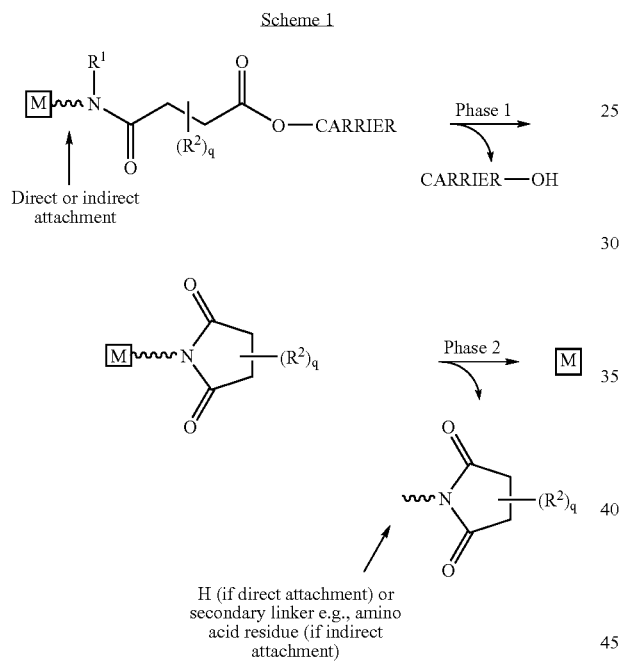

The dual phase release proceeds with ester bond cleavage (with release of Carrier-OH) and simultaneous M-succinimide formation at the amide side, followed by further hydrolysis of the M-succinimide moiety (with release of M). The release process may proceed with formation of by-products at Phase 1 and/or Phase 2. For example, a by-product that may be formed in Phase 1 includes:

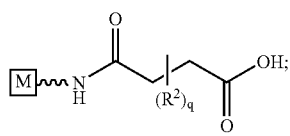

where ⁓⁓denotes direct of indirect attachment of M. Similarly, a by-product that may be formed in Phase 1 includes:

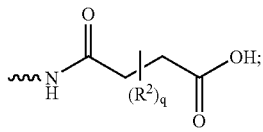

where ⁓⁓denotes Hydrogen (if direct attachment) or a secondary linker (if indirect attachment).

In one aspect, the invention encompasses drug-carrier conjugates whereby one or more drug moiety (e.g., MW smaller than or equal to about 10 kDa) is covalently attached to the carrier via an optionally substituted succinamide linker, either directly or indirectly.

As discussed above, such systems feature dual phase release of the drug moieties, as depicted in Scheme 2 below:

Scheme 2

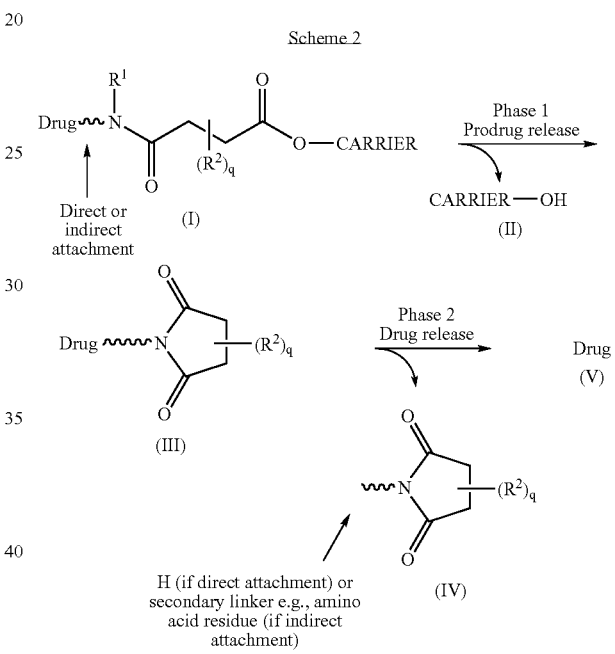

As discussed above, by-products may be formed in the process.

Attempts have been made to employ succinamidoester linkers with the amide group at the carrier side,[9] which did not result in dual phase drug release. In the inventive system, the succinamidoester is oriented such that the ester is formed at the carrier side, while the opposite carboxyl forms an amide bond with an amine-containing modifier (e.g., drug or drug derivative).

In certain embodiments, the inventive dual phase drug release system, as applied to drug molecules (i.e., as modifiers) allows the engineering of soluble, potentially targetable macromolecular preparations with novel pharmacokinetics and reduced toxicity. In certain embodiments, the inventive system involves assembling of a hydrophilic drug-carrier conjugate that releases a lipophilic prodrug (e.g., CPT prodrug which has a stabilized lactone ring), which, in turn, releases the active drug substance locally (intra- and extracellularly), without the need for prior metabolization by the hepatic microsomal P450 complex.

Potential advantages of the inventive dual phase release system, as applied to drugs, include: (1) the ability to prepare water soluble drug-carrier conjugates, which, for example, can be administered intravenously. (2) activation of the intermediate prodrug (III) "on site" rather than in the liver, so that local administration and targeting are possible [Applicant has exemplified this embodiment with CPT as the drug. Unlike other CPT prodrugs, e.g. Irinotecan, the intermediate CPT prodrug is indeed activated "on site"]. (3) the inventive method may allow release of certain drugs in stabilized form (in the form of drug-succinimide intermediate) (as is the case for CPT, which is release in a lactone-stabilized form), which ensures prodrug deposition in tissues and low rates of redistribution and transfer to urine.

This invention differs from existing drug release systems in at least the following ways:

(1) In drug release systems known in the art, the drug is generally intended to be released in one step. In contrast, the present invention involves (i) release of a succinimidated or drug molecule (prodrug), or a combination of succinimidated and succinamidated forms; and (ii) drug release from the succinimidated or succinamidated drug molecule.

(2) In small molecule release systems containing a succinamidate linker group between the drug molecule and the carrier known in the art, the drug is connected with said linker through an ester group. The drug is therefore released in one step, while the linker remains connected to the carrier.

It should be further understood that consideration should be given to the size (molecular weight) of Modifiers that may be used in practicing the present invention. For example, as described in more detail in Example 11, the reaction of cyclization-elimination which results in the succinimidated prodrug release involves folding of the succinamidoester into a cyclic intermediate structure (See, for example, Schemes 1 and 2), with subsequent intramolecular nucleophilic attack on the ester carbon. Without wishing to be bound by any particular theory, steric hindrance from a bulky Modifier (e.g., protein) may prevent such folding and, therefore, significantly interfere with drug release, making such modifiers not suitable for dual phase drug release. In certain embodiments, the present invention describes a class of modifiers that are suitable for dual phase drug release as modifiers with MW of less than 10 kDa, most preferably less than 1.5 kDa. The invention can utilize unsubstituted or substituted succinic acid derivatives, and can be used in combination with a variety of drug substances, including, but not limited to, antineoplastic, anti-infective, and anesthetic agents.

Carriers

In certain embodiments, the carrier is any small or large molecule, biomolecule, particle, gel or other object or material which can be covalently attached to one or more modifier (e.g., drug molecule) with a monosuccinamide linker. In certain embodiments, a carrier suitable for practicing the invention is any small or large molecule, biomolecule, particle, gel or other object or material which comprises one or more functionality amenable to succinylation. For example, a suitable carrier might comprise one or more functionality which can react, under suitable conditions, with an optionally substituted succinic anhydride having the structure:

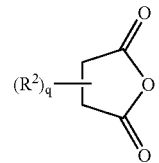

to form a succinylated carrier having the structure:

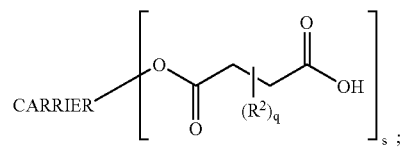

or salt thereof;

wherein s is an integer designating the number of succinylation sites on the carrier; q is an integer from 0-4; and each occurrence of $R^2$ is independently hydrogen, halogen, —CN, $NO_2$, an aliphatic, alicyclic, heteroaliphatic, heterocyclic, aryl, heteroaryl, aromatic, heteroaromatic moiety, or $-GR^{G1}$ wherein G is —O—, —S—, $-NR^{G2}$—, —C(=O)—, —S(=O)—, —$SO_2$—, —C(=O)O—, —C(=O)$NR^{G2}$—, —OC(=O)—, —$NR^{12}$C(=O)—, —OC(=O)O—, —OC(O)$NR^{G2}$—, —$NR^{G2}$C(=O)O—, —$NR^{G2}$C(O)$NR^{G2}$—, —C(=S)—, —C(=S)S—, —SC(=S)—, —SC(=S)S—, —C(=$NR^{G2}$)—, —C(—$NR^{G2}$)O—, —C(=O—$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ is independently hydrogen, halogen, or an optionally substituted aliphatic, heteroaliphatic, alicyclic, heteroalicyclic, aromatic, heteroaromatic, aryl or heteroaryl moiety.

In certain other embodiments, a suitable carrier might comprise one or more functionality which can react, under suitable conditions, with an optionally substituted succinic anhydride (as above), succinic acid

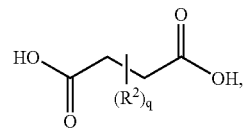

succinyl dihaloanhydride

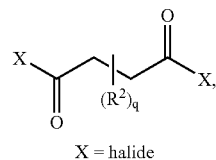

X = halide succinic ester

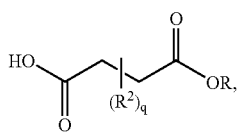

or any other reagent suitable for succinylation.

In certain other embodiments, a suitable carrier might comprise one or more functionality which can react, under suitable conditions, with an optionally substituted succinic acid having the structure:

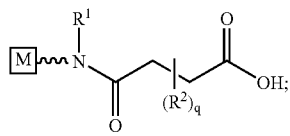

wherein q and $R^2$ are as defined above;
M is a modifier;
⁓⁓⁓denotes direct of indirect attachment of M to the succinyl moiety; and
$R^1$ is hydrogen, —C(=O)$R^{1.4}$, —C(=O)O$R^{1.4}$, —S$R^{1.4}$, SO$_2R^{1.4}$ or an aliphatic, alicyclic, heteroaliphatic, heterocyclic, aryl, heteroaryl, aromatic, heteroaromatic moiety, wherein each occurrence of $R^{1.4}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aromatic, heteroaromatic, aryl or heteroaryl;
to form a conjugate having the structure:

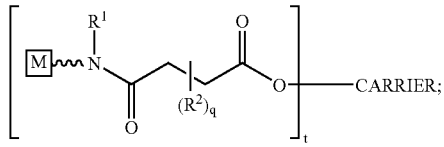

wherein t is an integer designating the number of modifier moieties conjugated to the carrier.

In certain embodiments, when the carrier is a polymer, about 2 to about 25% monomers comprise a modifier M, more preferably about 5 to about 20%, more preferably about 5 to about 18%, more preferably about 5 to about 15%, more preferably about 6 to about 15%, more preferably about 6 to about 14%, more preferably about 7 to about 13%, more preferably about 7 to about 12%, more preferably about 8 to about 12%, more preferably about 9 to about 12%, more preferably about 10 to about 12%, more preferably about 9 to about 11%, most preferably about 10 to about 11%.

In certain exemplary embodiments, the conjugates of the invention find use in biomedical applications, such as gene and drug delivery and tissue engineering, and the carrier is biocompatible and biodegradable. In certain embodiments, the carrier is a macromolecule, a molecular matrix (e.g., a gel or a solid) or an interface. In certain embodiments, the carrier is a macromolecule, soluble polymer, nanoparticle, gel, liposome, micelle, suture, implant, etc. In certain embodiment, the term "soluble polymer" encompasses biodegradable biocompatible polymer such as a polyal (e.g., hydrophilic polyacetal or polyketal). In certain other embodiments, the carrier is a fully synthetic, semi-synthetic or naturally-occurring polymer. In certain other embodiments, the carrier is hydrophilic.

In certain exemplary embodiments, the carriers used in the present invention are biodegradable biocompatible polyals comprising at least one hydrolyzable bond in each monomer unit positioned within the main chain. This ensures that the degradation process (via hydrolysis/cleavage of the monomer units) will result in fragmentation of the polymer conjugate to the monomeric components (i.e., degradation), and confers to the polymer conjugates of the invention their biodegradable properties. The properties (e.g., solubility, bioadhesivity and hydrophilicity) of biodegradable biocompatible polymer conjugates can be modified by subsequent substitution of additional hydrophilic or hydrophobic groups. Examples of biodegradable biocompatible polymers suitable for practicing the invention can be found inter alia in U.S. Pat. Nos. 5,811,510; 5,863,990 and 5,958,398; U.S. Provisional Patent Application 60/348,333; U.S. Utility patent application Ser. No. 10/501,565; European Patent Nos.: 0820473 and 03707375.6; and International Patent Applications PCT/US03/01017 and PCT/US03/22584, each of the above listed patent documents is incorporated herein by reference in its entirety. Guidance on the significance, preparation, and applications of this type of polymers may be found in the above-cited documents. In certain embodiments, it is anticipated that the present invention will be particularly useful in combination with the above-referenced patent documents, as well as U.S. Pat. No. 5,582,172; U.S. patent application Nos.: 60/147,919 and 09/634,320, each of the above listed patent documents is incorporated herein by reference in its entirety.

As described in the Examples, we have successfully made biodegradable biocompatible conjugates which are hydrophilic, hydrolyzable and comprise drug molecules (e.g., camptothecin (i.e., CPT)) covalently attached to the polymer carrier via monosuccinamide-containing linkages. Thus, in certain exemplary embodiments, carriers suitable for practicing the present invention are polyals having at least one acetal/ketal oxygen atom in each monomer unit positioned within the main chain. As discussed above, this ensures that the degradation process (via hydrolysis/cleavage of the polymer acetal/ketal groups) will result in fragmentation of the polyal conjugate to low molecular weight components (i.e., degradation). Thus, a novel aspect of the present invention relates in part to the structure and properties of conjugates comprising one or more modifiers covalently attached via succinamide-containing linkages to a hydrophilic carrier having acetal/ketal groups in the main chain.

In certain embodiments, biodegradable biocompatible polymer carriers, used for preparation of polymer conjugates of the invention, are naturally occurring polysaccharides, glycopolysaccharides, and synthetic polymers of polyglycoside, polyacetal, polyamide, polyether, and polyester origin and products of their oxidation, fictionalization, modification, cross-linking, and conjugation.

In certain other embodiments, the carrier is a hydrophilic biodegradable polymer selected from the group consisting of carbohydrates, glycopolysaccharides, glycolipids, glycoconjugates, polyacetals, polyketals, and derivatives thereof.

In certain exemplary embodiments, the carrier is a naturally occurring linear and branched biodegradable biocompatible homopolysaccharide selected from the group consisting of cellulose, amylose, dextran, levan, fucoidan, carraginan, inulin, pectin, amylopectin, glycogen and lixenan.

In certain other exemplary embodiments, the carrier is a naturally occurring linear and branched biodegradable biocompatible heteropolysaccharide selected from the group consisting of agarose, hyluronan, chondroitinsulfate, dermatansulfate, keratansulfate, alginic acid and heparin.

In yet other exemplary embodiments, the carrier is a hydrophilic polymer selected from the group consisting of polyacrylates, polyvinyl polymers, polyesters, polyorthoesters, polyamides, polypeptides, and derivatives thereof.

In certain embodiments, the carrier comprises polysaccharides activated by selective oxidation of cyclic vicinal diols of 1,2-, 1,4-, 1,6-, and 2,6-pyranosides, and 1,2-, 1,5-, 1,6-furanosides, or by oxidation of lateral 6-hydroxy and 5,6-diol containing polysaccharides prior to conjugation with one or more modifiers.

In one embodiment, the carriers of the invention comprise activated hydrophilic biodegradable biocompatible polymer carriers comprising from 0.1% to 100% polyacetal moieties represented by the following chemical structure:

wherein $R_1$ and $R_2$ are independently hydrogen, hydroxyl, carbonyl, carbonyl-containing substitutent, a biocompatible organic moiety comprising one or more heteroatoms or a protected hydrophilic functional group; and n is an integer from 1-5000.

In still other exemplary embodiments, the carrier comprises a biodegradable biocompatible polyacetal wherein at least a subset of the polyacetal repeat structural units have the following chemical structure:

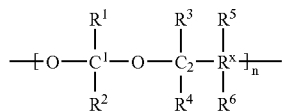

wherein for each occurrence of the n bracketed structure, one of $R^1$ and $R^2$ is hydrogen, and the other is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a functional group suitable for coupling with a succinamide through an ester bond. In certain embodiments, the functional group is a hydroxyl moiety.

In further exemplary embodiments, the carrier comprises a biodegradable biocompatible polyketal wherein at least a subset of the polyketal repeat structural units have the following chemical structure:

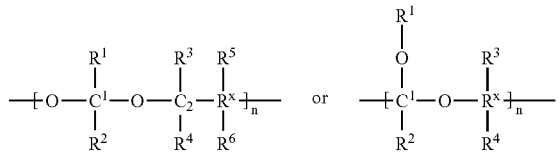

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a functional group suitable for coupling with a succinamide through an ester bond. In certain embodiments, the functional group is a hydroxyl moiety.

Examples of suitable organic moieties are aliphatic groups having a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters, polythioesters, pharmaceutically useful groups, a biologically active substance or a diagnostic label.

In certain embodiments, in the polyacetals and polyketals described directly above, for each occurrence of the bracketed structure n, at least one of $R^1$, $R^2$, $R^3$, $R^4$, $R^5$ and $R^6$ comprises a functional group that increases the polymer hydrophilicity or is adapted for covalent binding to the succinamide linker.

In certain embodiments, in the polyacetals and polyketals described directly above, for each occurrence of the bracketed structure n, at least one of $R^1$, $R^2$, $R^3$, $R^4$, $R^5$ and $R^6$ comprises a carbonyl group adapted for covalent binding to linker $L^M$. In certain exemplary embodiments, the polyacetals and polyketals described directly above, wherein at least one of $R^1$, $R^2$, $R^3$, $R^4$, $R^5$ and $R^6$ comprise a hydroxyl group, are conjugated with one or more moieties having the structure:

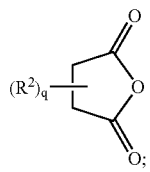

wherein q, and $R^2$ are as defined generally above and in classes and subclasses herein.

In yet another embodiment, at least one of $R^1$, $R^2$, $R^3$, $R^4$, $R^5$ and $R^6$ contains a chiral moiety.

In certain embodiments, the biodegradable biocompatible carriers of the invention can be crosslinked. Guidance for crosslinkers and crosslinking methodology in connection with polyals in general may be found, for example, in U.S. Provisional Application No. 60/348,333; U.S. Utility application Ser. No. 10/501,565 and International Application No.: PCT/US03/01017.

In certain exemplary embodiments, the carrier is a biodegradable biocompatible polyal that is crosslinked with epibromohydrin, or epichlorohydrin. In certain embodiments, the epibromohydrin or epichlorohydrin is present in an amount in the range of between about one and about twenty five percent by weight of the crosslinked biodegradable biocompatible polyals.

In one embodiment, biodegradable biocompatible polyals suitable for practicing the present invention have a molecular weight of between about 0.5 and about 1500 kDa. In a preferred embodiment of the present invention, the biodegradable biocompatible polyals have a molecular weight of between about 1 and about 1000 kDa.

In certain embodiments, the polymer carriers are modified (i.e., conjugated with one or more modifiers) at one or both termini. For example, when the carrier is a polyketal, the carrier may have the structure:

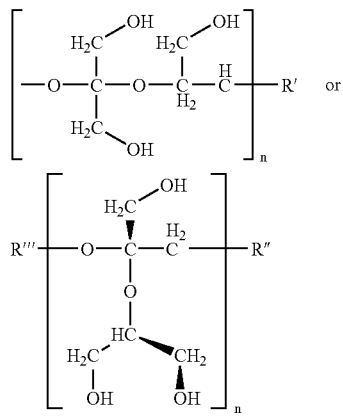

wherein n is an integer and R', R" and R'" may be a modifier. For example, R' can comprise an N-hydroxysuccinimide ester or a maleimide moiety for conjugation with proteins or other biomolecules; R" and R'" can comprise a phospholipid and a target specific moiety, such as antibody, respectively, for liposome modification.

In certain other embodiments, carriers can be substituted at one terminal and one or more non-terminal positions, or at both terminal and one or more non-terminal positions.

In certain embodiments, the carrier is a linear macromolecule, a branched macromolecule, a globular macromolecule, a graft copolymer, a comb copolymer, a nanoparticle or a lipid-based carrier. In certain exemplary embodiments, the lipid-based carrier is a liposome.

In certain embodiments, the carrier is PHF, a structure of which is shown below:

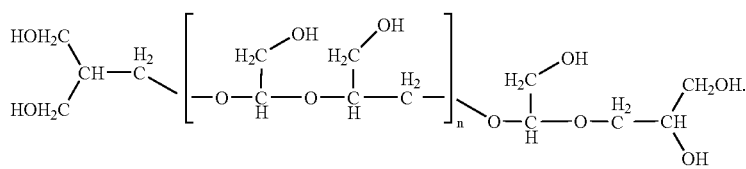

Modifiers

In certain embodiments, modifiers according to the invention include, but are not limited to, biomolecules, small molecules, organic or inorganic molecules, therapeutic agents, microparticles, pharmaceutically useful groups or entities, macromolecules, diagnostic labels, chelating agents, intercalator, hydrophilic moieties, dispersants, charge modifying agents, viscosity modifying agents, surfactants, coagulation agents and flocculants, to name a few. In certain embodiment, the modifier is a chemotherapeutic moiety. In certain embodiments, the modifier is camptothecin (CPT), which is optionally covalently bound to a secondary linker. In certain embodiments, the modifier is Taxol, which is optionally covalently bound to a secondary linker. In certain embodiments, the modifier is Illudin, which has the structure:

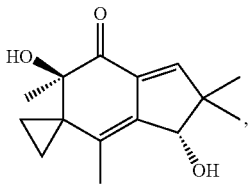

which is optionally covalently bound to a secondary linker.

Examples of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Examples of small molecules include, but are not limited to, drugs such as vitamins, anti-AIDS substances, ant-cancer substances, radionuclides, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics and imaging agents.

In certain embodiments, the modifier is a small molecule having a molecular weight preferably ≦about 10 kDa, more preferably ≦about 9 kDa, more preferably ≦about 8 kDa, more preferably ≦about 7 kDa, more preferably ≦about 6 kDa, more preferably ≦about 5 kDa, more preferably ≦about 4 kDa, more preferably ≦about 3 kDa, most preferably ≦about 1.5 kDa.

Examples of suitable pharmaceutically useful groups or entities include, but are not limited to, hydrophilicity/hydrophobicity modifiers, pharmacokinetic modifiers, biologically active modifiers and detectable modifiers.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g. paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. Fluorescent labels can be used for photoimaging. In certain embodiments a modifier comprises a paramagnetic ion or group.

In certain embodiments, the modifier may be chemically modified so that it comprises a functional group (i.e., amine group) suitable for covalent binding with an optionally substituted succinic acid through formation of an amide bond; said succinic acid being conjugated to the carrier through formation of an ester bond.

Conjugates

Conjugates of the invention comprise one or more occurrences of M, where M is a modifier, wherein the one or more occurrences of M may be the same or different. In certain embodiments, one or more occurrences of M is a biocompatible moiety. In certain embodiments, one or more occurrences of M is a hydrophilic moiety. In certain embodiments, one or more occurrences of M is a drug molecule. In certain embodiments, one or more occurrences of M is a chemotherapeutic moiety. In certain embodiments, one or more occurrences of M is a camptothecin moiety.

In certain other embodiment, one or more occurrences of M is attached to the succinamide linker either directly or through a secondary linker. In certain embodiments, the secondary linker is an amino acyl residue, and the conjugate has the following general structure:

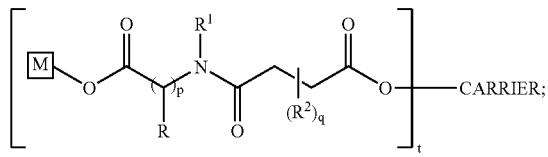

wherein p is an integer from 1-12; t is an integer designating the number of modifier moieties conjugated to the carrier; and each occurrence of R is independently hydrogen, halogen, —CN, NO$_2$, an aliphatic, alicyclic, heteroaliphatic, heterocyclic, aryl, heteroaryl, aromatic, heteroaromatic moiety, or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ is independently hydrogen, halogen, or an optionally substituted aliphatic, heteroaliphatic, alicyclic, heteroalicyclic, aromatic, heteroaromatic, aryl or heteroaryl moiety.

In certain embodiments, the secondary linker is an α-amino acyl residue, and the conjugate has the following general structure:

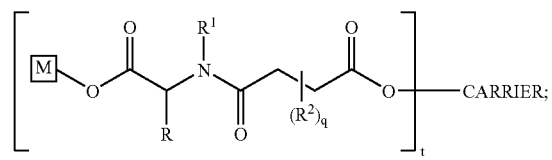

wherein t is an integer designating the number of modifier moieties conjugated to the carrier; and R designates a natural or unnatural amino acid side chain.

As discussed more generally above, in certain embodiments, when the carrier is a polymer, about 2 to about 25% monomers comprise a modifier M, more preferably about 5 to about 20%, more preferably about 5 to about 18%, more preferably about 5 to about 15%, more preferably about 6 to about 15%, more preferably about 6 to about 14%, more preferably about 7 to about 13%, more preferably about 7 to about 12%, more preferably about 8 to about 12%, more preferably about 9 to about 12%, more preferably about 10 to about 12%, more preferably about 9 to about 11%, most preferably about 10 to about 11%.

In certain embodiments, M is CPT. In certain embodiments, M is CPT and the secondary linker is an amino acyl residue. In certain embodiments, M is CPT and the secondary linker is a glycine residue.

In other embodiments, in the conjugates of the invention, one or more occurrences of M comprises a biologically active modifier. In certain exemplary embodiments, one or more occurrence of M is selected from the group consisting of proteins, antibodies, antibody fragments, peptides, steroids, intercalators, drugs, hormones, cytokines, enzymes, enzyme substrates, receptor ligands, lipids, nucleotides, nucleosides, metal complexes, cations, anions, amines, heterocycles, heterocyclic amines, aromatic groups, aliphatic groups, intercalators, antibiotics, antigens, immunomodulators, and antiviral compounds. In certain embodiments, the drugs include, but are not limited to, antineoplastic, antibacterial, antiviral, antifungal, antiparasital, anesthetic drugs.

In certain embodiment, the modifier is a chemotherapeutic moiety. In certain embodiments, the modifier is camptothecin (CPT). Thus, in one aspect, the present invention provides a CPT-carrier conjugate, wherein CPT and the carrier are covalently attached through a succinamide-containing linker, whereby CPT is directly or indirectly attached to the succinamide moiety through an amide bond, and the carrier is linked directly or indirectly to the succinamide moiety through an ester bond. In certain embodiments, CPT is indirectly attached to the succinamide moiety via an amino acyl moiety. In certain embodiments, CPT is indirectly attached to the succinamide moiety via a glycine moiety. In certain embodiments, the carrier is a polyal, such as those described herein.

In certain embodiments, there is provided a PHF-CPT conjugate having the structure (I) shown in Scheme 3 below:

Scheme 3
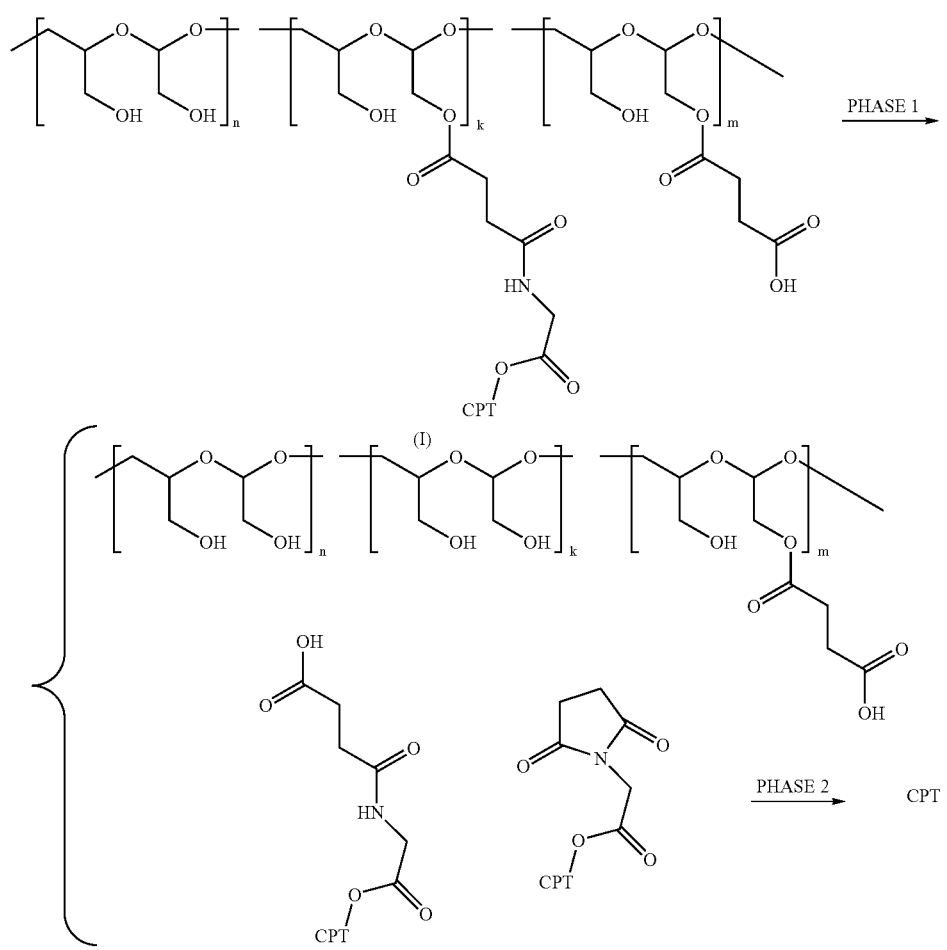
wherein n, k and m are integers between 10-300, 1-20, and 0-300 respectively.
As depicted above, conjugate (I) can subsequently release CPT in a two-phase process.
In certain embodiment, there is provided a PHF-CPT conjugate having the structure:
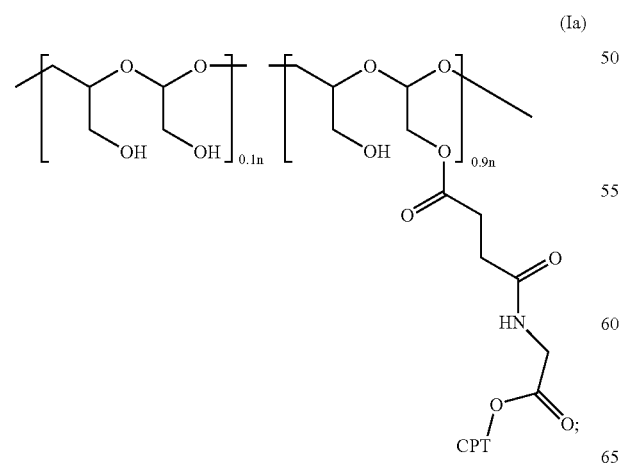
wherein n is an integer between 10-3000.

In certain embodiments, there is provided a PHF-Taxol conjugate having the structure (II) shown in Scheme 4 below:

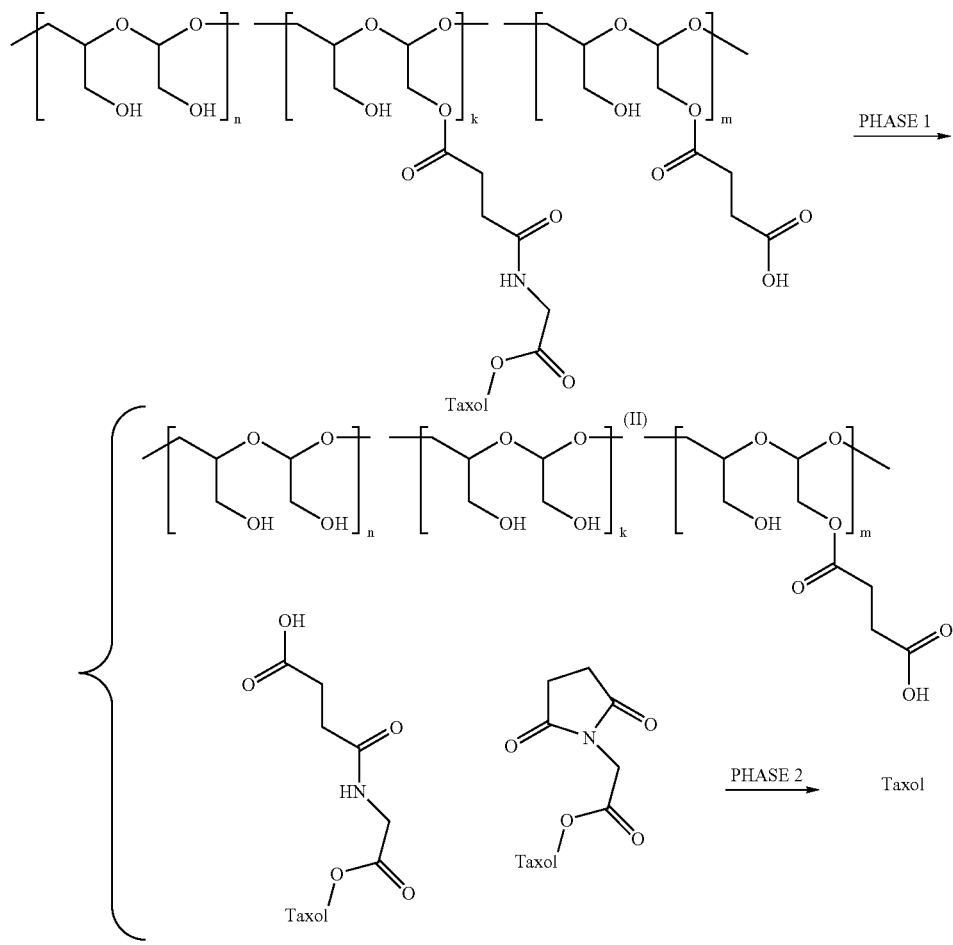

wherein n, k and m are integers between 10-300, 1-20, and 0-300 respectively.

As depicted above, conjugate (II) can subsequently release Taxol in a two-phase process.

In certain embodiment, there is provided a PHF-Taxol conjugate having the structure:

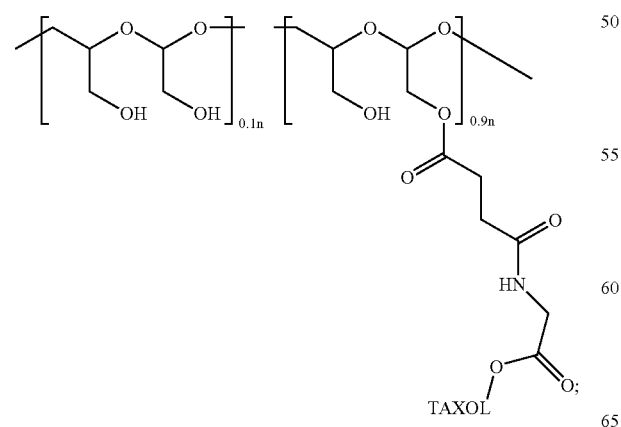

wherein n is an integer between 10-3000.

In certain embodiments, there is provided a PHF-Illudin conjugate having the structure (III) shown in Scheme 5 below:
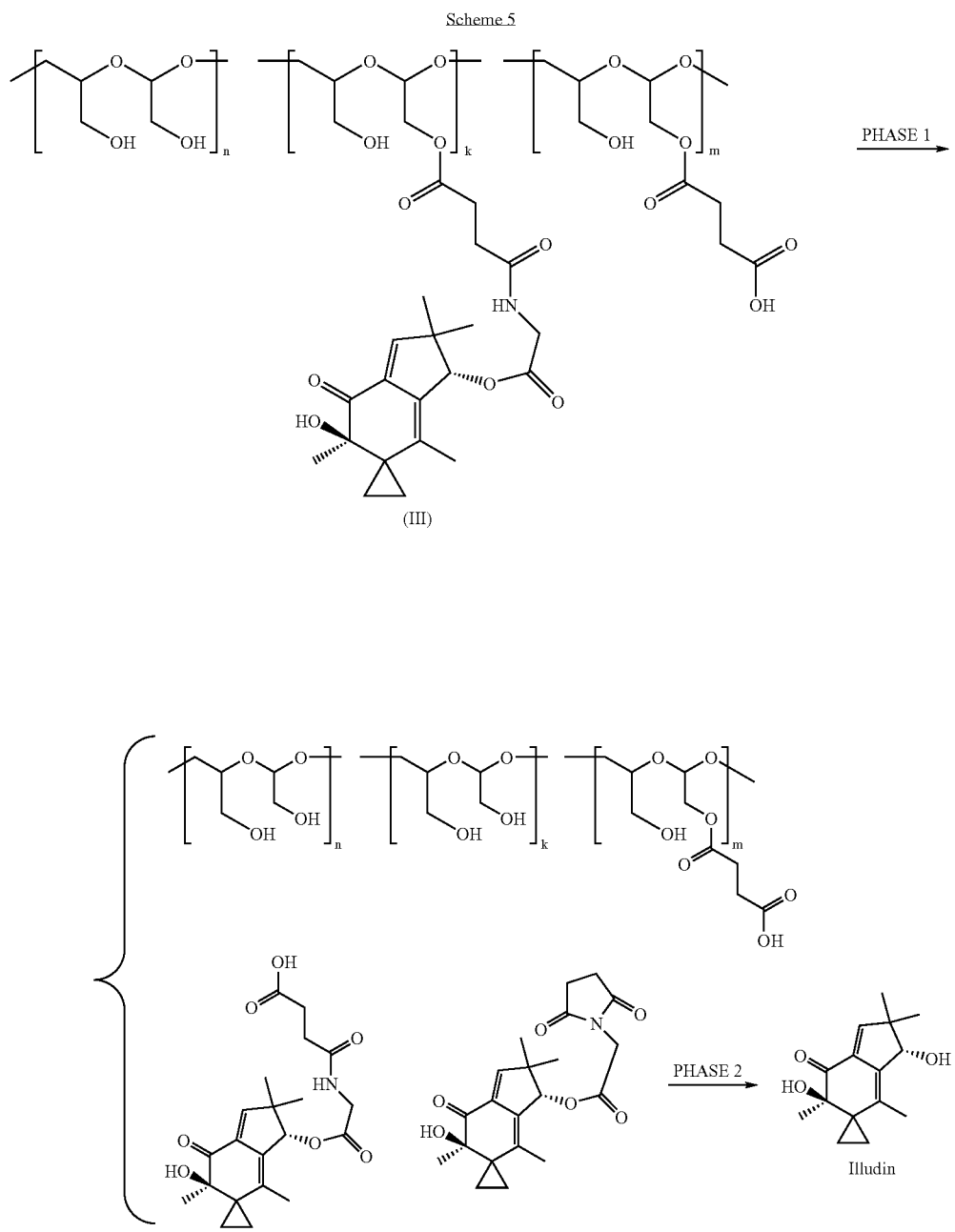
wherein n, k and m are integers between 10-300, 1-20, and 0-300 respectively.
As depicted above, conjugate (III) can subsequently release Illudin in a two-phase process.
In certain embodiments, there is provided a PHF-Illudin conjugate having the structure:

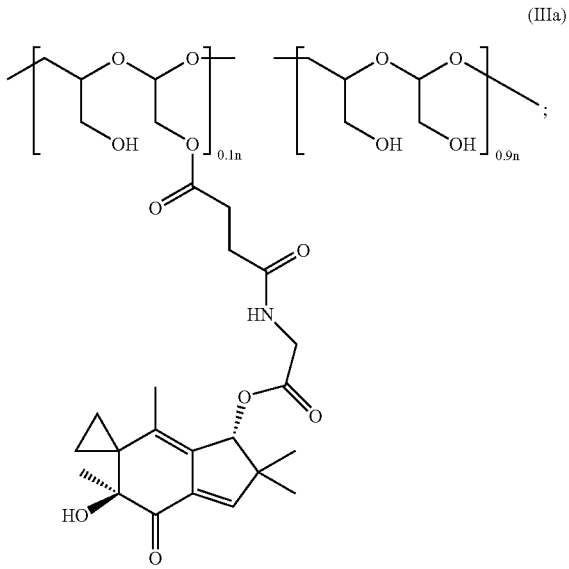

(IIIa)

wherein n is an integer between 10-3000.

In certain other embodiments, one or more occurrence of M comprises a detectable label. In certain exemplary embodiments, one or more occurrence of M comprises atoms or groups of atoms comprising radioactive, paramagnetic, superparamagnetic, fluorescent, or light absorbing structural domains.

In certain other embodiments, one or more occurrences of M comprise a diagnostic label.

In certain exemplary embodiments, the inventive conjugate comprises a biologically active modifier and a detectable label.

In certain other embodiments, the inventive conjugate comprises a detectable label linked directly to the polymer chain.

The biodegradable biocompatible conjugates of the invention can be prepared to meet desired requirements of biodegradability and hydrophilicity. For example, under physiological conditions, a balance between biodegradability and stability can be reached. For instance, it is known that macromolecules with molecular weights beyond a certain threshold (generally, above 50-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. One skilled on the art can select other suitable methods for studying various fragments of the degraded conjugates of this invention.

In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells. Accordingly, in certain embodiments, the conjugates of the present invention are expected to be biodegradable, in particular upon uptake by cells, and relatively "inert" in relation to biological systems. The products of carrier degradation are preferably uncharged and do not significantly shift the pH of the environment. It is proposed that the abundance of alcohol groups may provide low rate of polymer recognition by cell receptors, particularly of phagocytes. The polymer backbones of the present invention generally contain few, if any, antigenic determinants (characteristic, for example, for some polysaccharides and polypeptides) and generally do not comprise rigid structures capable of engaging in "key-and-lock" type interactions in, vivo unless the latter are desirable. Thus, the soluble, crosslinked and solid conjugates of this invention are predicted to have low toxicity and bioadhesivity, which makes them suitable for several biomedical applications.

In certain embodiments of the present invention, the biodegradable biocompatible conjugates can form linear or branched structures. For example, the biodegradable biocompatible polyal conjugates of the present invention can be chiral (optically active). Optionally, the biodegradable biocompatible polyal conjugates of the present invention can be racemic.

In yet another embodiment, the conjugates of the present invention are associated with a macromolecule or a nanoparticle. Examples of suitable macromolecules include, but are not limited to, enzymes, polypeptides, polylysine, proteins, lipids, polyelectrolytes, antibodies, ribonucleic and deoxyribonucleic acids and lectins. The macromolecule may be chemically modified prior to being associated with said biodegradable biocompatible conjugate. Circular and linear DNA and RNA (e.g., plasmids) and supramolecular associates thereof, such as viral particles, for the purpose of this invention are considered to be macromolecules. In certain embodiments, conjugates of the invention are non-covalently associated with macromolecules.

In certain embodiments, the conjugates of the invention are water-soluble. In certain embodiments, the conjugates of the invention are water-insoluble. In certain embodiments, the inventive conjugate is in a solid form. In certain embodiments, the conjugates of the invention are colloids. In certain embodiments, the conjugates of the invention are in particle form. In certain embodiments, the conjugates of the invention are in gel form. In certain embodiments, the conjugates of the invention are in a fiber form. In certain embodiments, the conjugates of the invention are in a film form.

Applications

In one aspect, an area of application of the present invention is cancer treatment/chemotherapy. However, the scope of application of the invention is not limited to this area. Other applications will be readily apparent to the reader.

Despite the significant recent improvements in cancer statistics in the US, cancer remains one of the major causes of death. The efficacy of chemotherapy, which is the major therapeutic modality, is still limited by the toxicity of the available drugs that hinders dose elevation to the levels resulting in reliable remission. One aspect of the present invention relates to the possibility of developing new, considerably more efficient and less toxic chemotherapeutic preparations. The inventive system can also be useful in inflammation, pain management, and, generally, in all other areas where various sustained release or targeting of drugs is beneficial.

Macromolecular drug delivery systems, which have been extensively studied over the past two decades, significantly improved the pharmacological properties of several drug substances, and provided new tools for controlling drug delivery to cancer cells.[18,19] A vast majority of the antineoplastic drug conjugates reported so far (a) are inactive until the drug substance is released from the macromolecular carrier, and (b) the drug substance is released, or at least intended to be released, in one stage.[20,21] In some cases, the conjugate (e.g., of a protein) may be active without drug release from the carrier.

Benefits of drug association with carrier macromolecules relate, in part, to the following factors: (1) solubilization of the drug substance; (2) restricted drug substance access to normal interstitium due to the large hydrodynamic size of the conjugate, (3) conjugate delivery to the tumor tissues via the Enhanced Permeability and Retention (EPR) effect,[22] and (4) maintenance of sustained drug levels over periods exceeding cancer cell cycle. In some (more recently developed) conjugates, the specificity of drug delivery to cancer cells is further addressed via incorporation of various targeting moieties (e.g., antibodies), and via enzyme-assisted hydrolysis of the link connecting the drug molecule to the carrier.[23,24]

In several preclinical studies, antineoplastic drug conjugates were shown to be less toxic than respective free drugs.[25] Antineoplastic activity of the conjugates (per unit of the administered drug substance) was usually lower than of unmodified drugs, although in some cases similar or higher.[26] However, conjugates are frequently more effective at equitoxic doses, so the partial loss of antineoplastic activity is outweighed by the lower toxicity and larger maximal tolerated doses.

In one aspect, the dual phase drug release system of the invention adds two additional major benefits: (1) an added feature of controlled properties of the released prodrug (e.g., hydrophobicity, affinity to cell components, transmembrane transport, drug activity preservation, redistribution from the release site); and (2) an added possibility to regulate both phases of drug release, (thus, for example, optimizing active drug levels and release duration vs. cancer cell cycle).

As mentioned above, carriers such as non-bioadhesive, fully biodegradable soluble polymer conjugates would be highly desirable to practice the present invention.

Synthetic Methods

According to the present invention, any available techniques can be used to make the inventive conjugates or compositions including them, and intermediates and components (e.g., carriers and modifiers) useful for making them. For example, semi-synthetic and fully synthetic methods such as those discussed in detail below may be used.

Carriers

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863,990 and 5,958,398; U.S. Provisional Patent Application 60/348,333; U.S. Utility patent application Ser. No. 10/501,565; European Patent Nos.: 0820473 and 03707375.6; and International Patent Applications PCT/US03/01017 and PCT/US03/22584. The skilled practitioner will know how to adapt these methods to make polymer carriers for use in the practice of the invention.

For example, semi-synthetic polyals may be prepared from polyaldoses and polyketoses via complete lateral cleavage of carbohydrate rings with periodate in aqueous solutions, with subsequent conversion into hydrophilic moieties (e.g. via borohydride reduction) for conjugation of hydroxyl groups with one or more modifiers, via a succinamide linker. In an exemplary embodiment, the carbohydrate rings of a suitable polysaccharide can be oxidized by glycol-specific reagents, resulting in the cleavage of carbon-carbon bonds between carbon atoms that are each connected to a hydroxyl group. An example of application of this methodology to dextran B-512 is illustrated below:

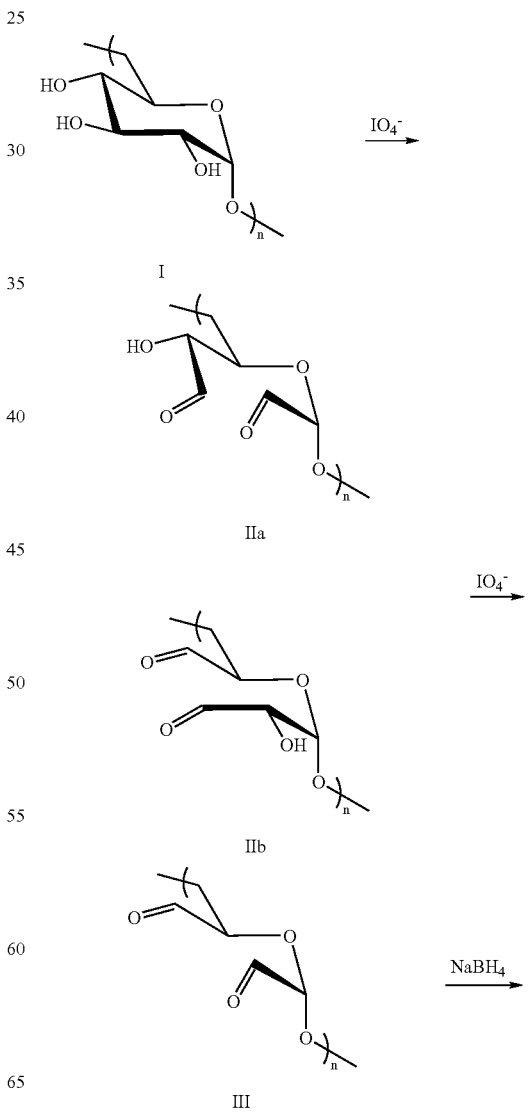

-continued

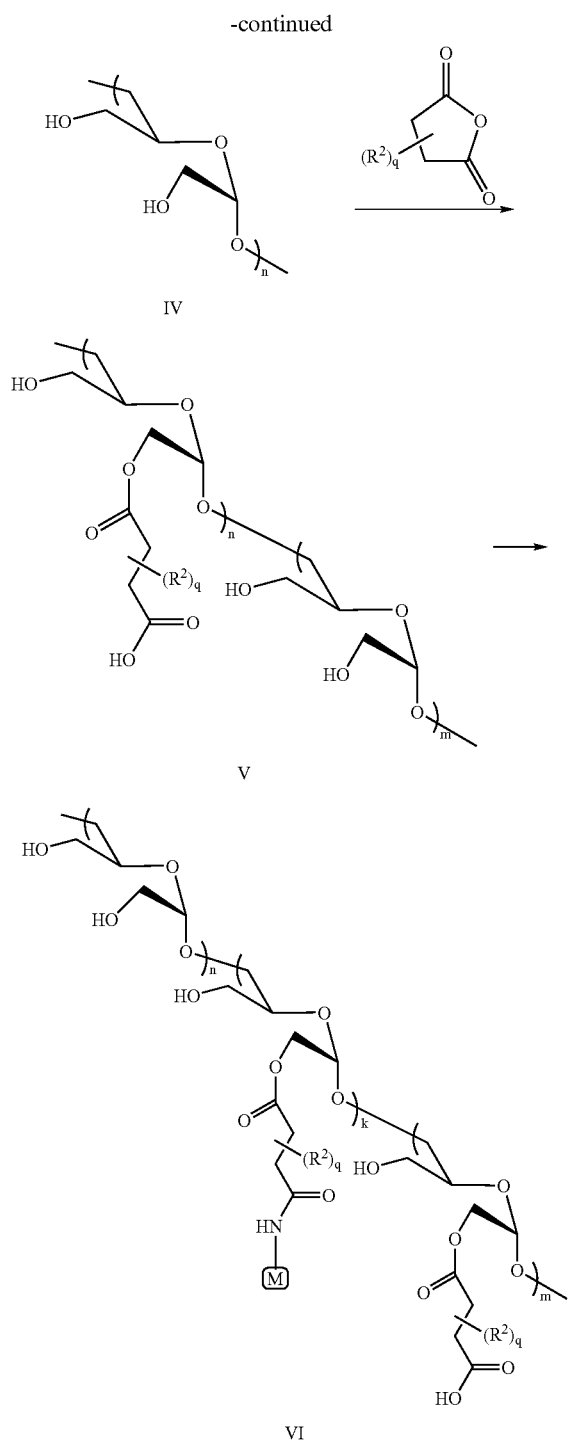

IV

V

VI

A similar approach may be used with Levan:

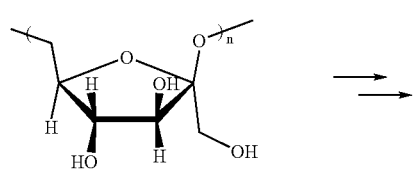

-continued

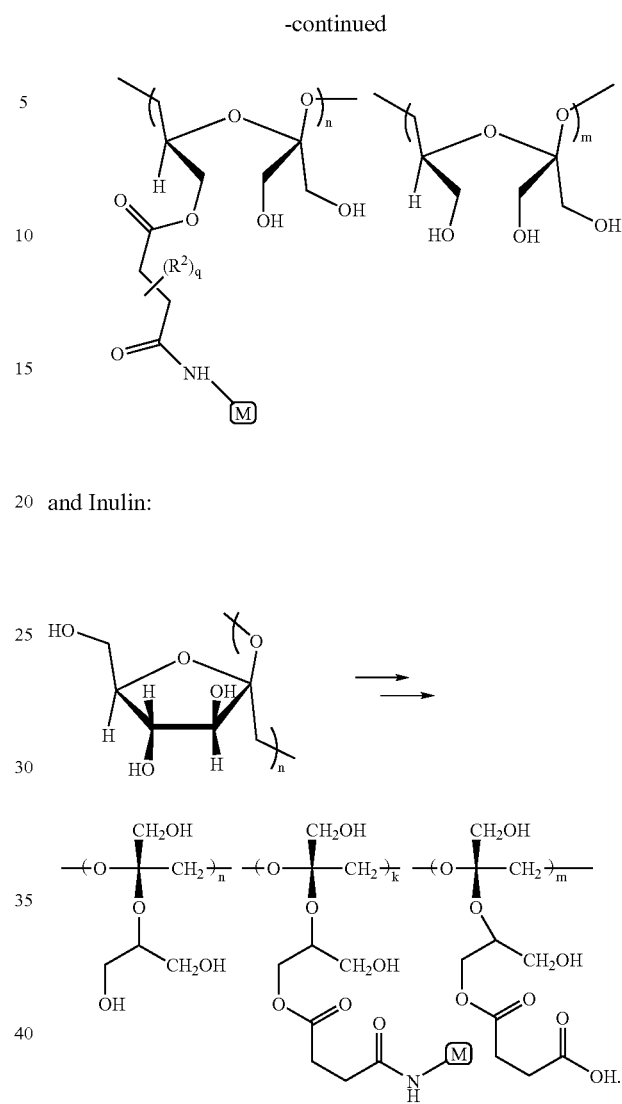

and Inulin:

In one embodiment, a method for forming the biodegradable biocompatible polyal conjugates of the present invention comprises a process by which a suitable polysaccharide is combined with an efficient amount of a glycol-specific oxidizing agent to form an aldehyde intermediate. The aldehyde intermediate, which is a polyal itself, may then be reduced to the corresponding polyol, succinulated, and coupled with one or more suitable modifiers to form a biodegradable biocompatible polyal conjugate comprising succinamide-containing linkages.

In another preferred embodiment, fully synthetic biodegradable biocompatible polyals for used in the present invention can be prepared by reacting a suitable initiator with a suitable precursor compound.

For example, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

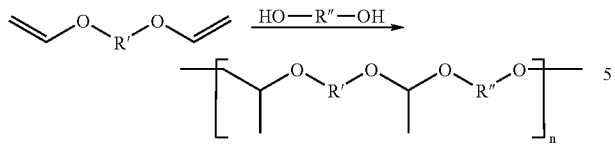

One of ordinary skill in the art will appreciate that solvent systems, catalysts and other factors may be optimized to obtain high molecular weight products.

In certain embodiments, the carrier is PHF having the structure:

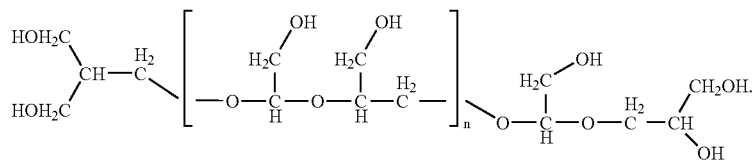

Modifiers

In certain embodiments, modifiers according to the invention include, but are not limited to, biomolecules, small molecules, organic or inorganic molecules, therapeutic agents, microparticles, pharmaceutically useful groups or entities, macromolecules, diagnostic labels, chelating agents, intercalator, hydrophilic moieties, dispersants, charge modifying agents, viscosity modifying agents, surfactants, coagulation agents and flocculants, to name a few.

As discussed above, modifiers useful in the practice of the invention may be chemically modified so that they independently comprise a functional group suitable for covalent binding with an optionally substituted succinic acid through formation of an amide bond; said succinic acid being conjugated to the carrier through formation of an ester bond.

Conjugates

In another aspect, the invention provides a method for preparing a conjugate comprising a carrier substituted with one or more occurrences of a moiety having the structure:

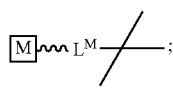

wherein each occurrence of M is independently a modifier;
∼∼∼denotes direct of indirect attachment of M to linker $L^M$; and
each occurrence of $L^M$ is independently an optionally substituted succinamide-containing linker, whereby the modifier M is directly or indirectly attached to the succinamide linker through an amide bond, and the carrier is linked directly or indirectly to each occurrence of the succinamide linker through an ester bond;
said method comprising steps of:
providing a carrier;
providing one or more modifiers;
reacting the carrier with an optionally substituted succinic anhydride having the structure:

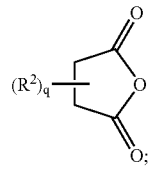

wherein q is an integer from 0-4; and each occurrence of $R^2$ is independently hydrogen, halogen, —CN, $NO_2$, an aliphatic, alicyclic, heteroaliphatic, heterocyclic, aryl, heteroaryl, aromatic, heteroaromatic moiety, or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ is independently hydrogen, halogen, or an optionally substituted aliphatic, heteroaliphatic, alicyclic, heteroalicyclic, aromatic, heteroaromatic, aryl or heteroaryl moiety;
under suitable conditions to form a succinylated carrier having the structure:

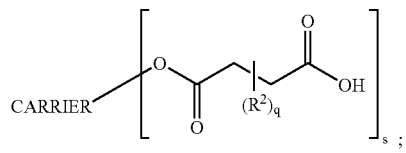

or salt thereof;
wherein s denotes the number of succinyl moieties on the carrier; and
reacting the succinylated carrier with one or more modifier moieties (M, whereby at least one modifier moiety forms an amide bond, either directly or indirectly through a secondary linker, with a succinyl moiety present on the carrier; thereby generating the conjugate having the structure:

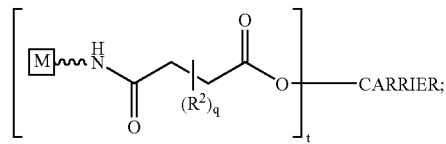

wherein $R^2$ and q are as defined above; ∿∿denotes direct of indirect attachment of M to the succinamide linker; and t is an integer designating the number of modifier moieties conjugated to the carrier such that t≦s.

In certain embodiments, each occurrence of $R^2$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aromatic, heteroaromatic, aryl, heteroaryl, —C(=O)$R^{2A}$ or —Z$R^{2A}$, wherein Z is —O—, —S—, —N$R^{2B}$, wherein each occurrence of $R^{2A}$ and $R^{2B}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, each occurrence of $R^2$ is hydrogen. In certain embodiment, one or more occurrences of $R^2$ is a $C_{1-10}$ alkyl moiety. In certain embodiment, one or more occurrences of $R^2$ is lower alkyl. In certain embodiment, one or more occurrences of $R^2$ is a hydrophobic group. In certain embodiment, one or more occurrences of $R^2$ is a hydrophilic group. In certain embodiment, one or more occurrences of $R^2$ is an anionic group. In certain embodiment, one or more occurrences of $R^2$ is a cationic group. In certain embodiment, one or more occurrences of $R^2$ is a receptor ligand.

In certain exemplary embodiments, in the step of coupling the succinylated carrier, a subset of the succinamic acid sites on the carrier remains unreacted.

In certain embodiments, the degree of succinylation on the carrier is modulated by varying the ratio of succinic anhydride amount vs. carrier amount in the step of reacting the carrier with the optionally substituted succinic anhydride. Thus, succinylation may be controlled by selecting the appropriate succinic anhydride/carrier ratio.

In certain embodiments, the degree of modifier incorporation in the conjugate is modulated by varying the ratio of modifier amount vs. succinylated carrier amount in the step of reacting the succinylated carrier with one or more modifier moieties. Thus, modifier contents in the conjugate may be controlled by selecting the appropriate modifier/succinylated carrier ratio. In certain embodiments, the degree of modifier incorporation in the conjugate is determined by the degree of carrier succinylation.

In certain exemplary embodiments, in practicing the method of the invention, the carrier is a biodegradable biocompatible polyal such as those disclosed in U.S. Pat. Nos. 5,811,510; 5,863,990 and 5,958,398; U.S. Provisional Patent Application 60/348,333; U.S. Utility patent application Ser. No. 10/501,565; European Patent Nos.: 0820473 and 03707375.6; and International Patent Applications PCT/US03/01017 and PCT/US03/22584.

In certain embodiments, a variety of modifiers can be mixed together with the succinylated carrier and the reaction mixture incubated in suitable conditions until the desirable conversion degree is achieved. This method can be used, via mixing the modifiers and the carrier at different ratios, to produce, in one step, libraries of conjugates with varying modifier composition and content.

In certain embodiment, the modifier is a chemotherapeutic moiety. In certain embodiments, the modifier is camptothecin (CPT), Taxol or Illudin. Thus, in one aspect, the present invention provides a method for preparing a CPT-, Taxol- or Illudin-carrier conjugate, wherein CPT, Taxol or Illudin and the carrier are covalently attached through a succinamide-containing linker, whereby CPT, Taxol or Illudin is directly or indirectly attached to the succinamide moiety through an amide bond, and the carrier is linked directly or indirectly to the succinamide moiety through an ester bond. In certain embodiments, CPT, Taxol or Illudin is indirectly attached to the succinamide moiety via an amino acyl moiety. In certain embodiments, CPT, Taxol or Illudin is indirectly attached to the succinamide moiety via a glycine moiety. In certain embodiments, the carrier is a polyal, such as those described herein. In certain exemplary embodiments, the polyal is PHF. In certain embodiments, a PHF-CPT conjugate according to the present invention can be prepared as follows:

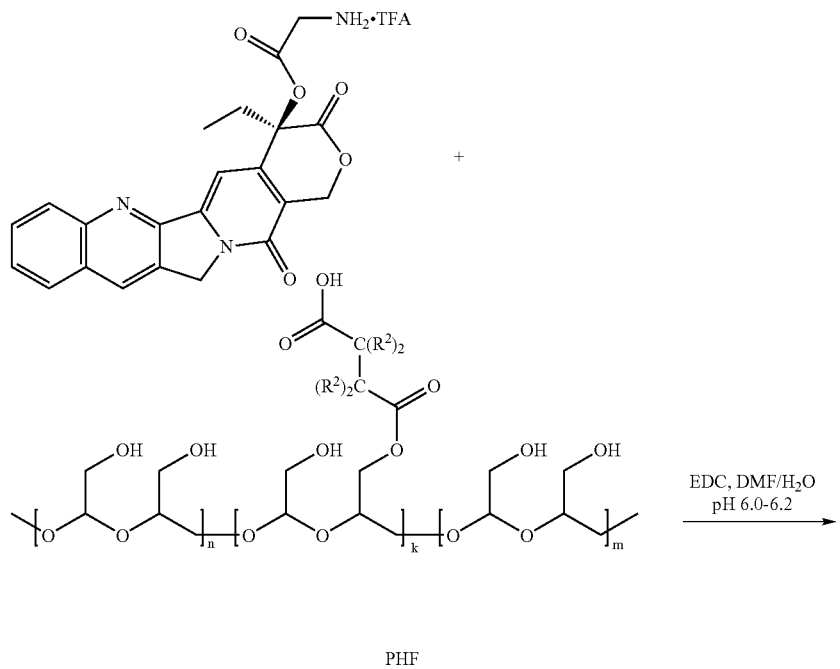

PHF

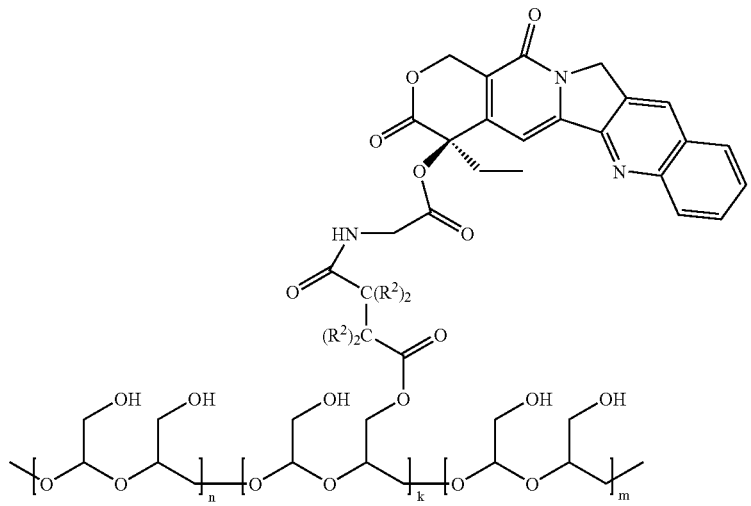
where m + n + k = 1, and k = 0.11-0.12 and each occurrence of $R^2$ may be the same or different and is as defined herein
In certain embodiments, a PHF-Taxol conjugate according to the present invention can be prepared as follows:
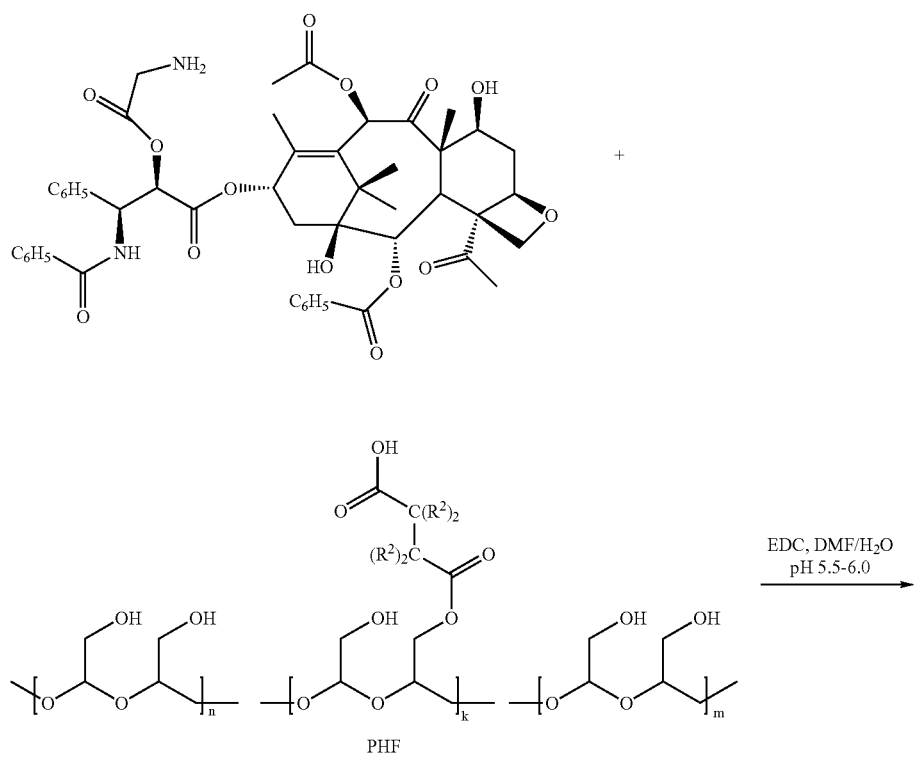

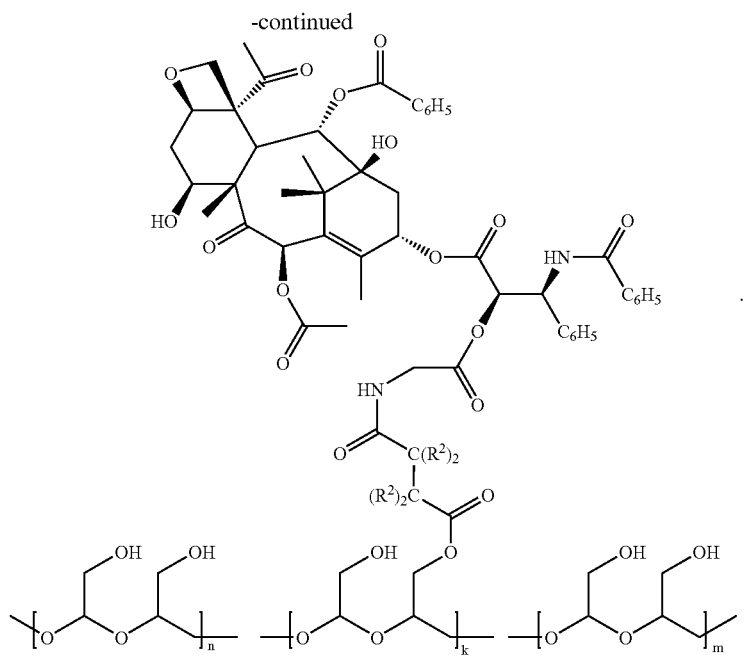

where m + n + k = 1, and k = 0.11-0.12 and each occurrence of R² may be the same or different and is as defined herein In certain embodiments, a PHF-Illudin conjugate according to the present invention can be prepared as follows:

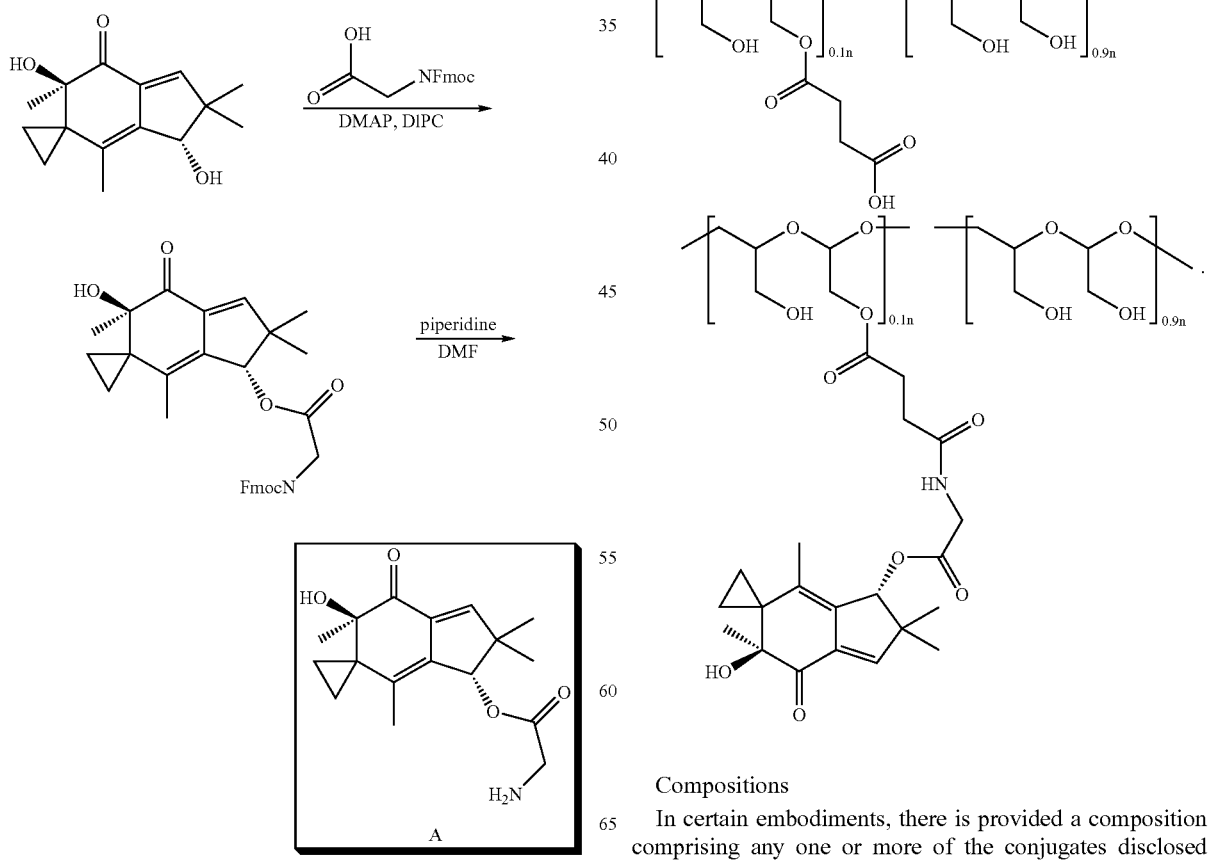

Compositions

In certain embodiments, there is provided a composition comprising any one or more of the conjugates disclosed herein and a pharmaceutically suitable carrier or diluent. In certain embodiments, the composition comprises a CPT-carrier conjugate. In certain embodiments, CPT is indirectly attached to the succinamide moiety via an amino acyl moiety. In certain embodiments, CPT is indirectly attached to the succinamide moiety via a glycine moiety. In certain embodiments, the carrier is a polyal, such as those described herein. In certain exemplary embodiments, the polyal is PHF. In certain embodiments, the composition comprises a PHF-CPT conjugate having formula (I) or (Ia).

In certain embodiments, the composition comprises a Taxol-carrier conjugate. In certain embodiments, Taxol is indirectly attached to the succinamide moiety via an amino acyl moiety. In certain embodiments, Taxol is indirectly attached to the succinamide moiety via a glycine moiety. In certain embodiments, the carrier is a polyal, such as those described herein. In certain exemplary embodiments, the polyal is PHF. In certain embodiments, the composition comprises a PHF-Taxol conjugate having formula (II) or (IIa).

In certain embodiments, the composition comprises a Illudin-carrier conjugate. In certain embodiments, Illudin is indirectly attached to the succinamide moiety via an amino acyl moiety. In certain embodiments, Illudin is indirectly attached to the succinamide moiety via a glycine moiety. In certain embodiments, the carrier is a polyal, such as those described herein. In certain exemplary embodiments, the polyal is PHF. In certain embodiments, the composition comprises a PHF-Illudin conjugate having formula (III) or (IIIa).

In certain embodiments, the invention provides a composition in the form of a gel of the inventive biodegradable biocompatible conjugate and a biologically active compound disposed within the gel. Alternatively or additionally, a diagnostic label can be disposed within the gel or bound to the gel matrix.

In another embodiment, the invention provides a composition in the form of a solution of the biodegradable biocompatible polyal conjugate and a pharmaceutically useful entity, a drug or a macromolecule dissolved within the solution. Alternatively or additionally, a diagnostic label can be dissolved within the solution.

In certain embodiments, there is provided a composition comprising a biodegradable biocompatible conjugate of the invention associated with an efficient amount of a therapeutic agent; wherein the therapeutic agent is incorporated into and released from said biodegradable biocompatible conjugate matrix by degradation of the polymer matrix or diffusion of the agent out of the matrix over a period of time. In certain embodiments, the conjugate is non-covalently associated with an efficient amount of a therapeutic agent. In certain embodiments, the therapeutic agent is selected from the group consisting of vitamins, anti-AIDS substances, anti-cancer substances, radionuclides, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, imaging agents, and combination thereof.

In variations of these embodiments, it may be desirable to include other pharmaceutically active compounds, such as antiinflammatories or steroids which are used to reduce swelling, antibiotics, antivirals, or antibodies. Other compounds which can be included are preservatives, antioxidants, and fillers, coatings or bulking agents which may also be utilized to alter polymer matrix stability and/or drug release rates.

Additives Used to Alter Properties of Conjugate Compositions:

In a preferred embodiment, only conjugate is incorporated into the delivery device or construct, although other biocompatible, preferably biodegradable or metabolizable, materials can be included for processing, preservation and other purposes, such as buffers and fillers.

Buffers, acids and bases are used to adjust the pH of the composition. Agents to increase the diffusion distance of agents released from the implanted polymer can also be included.

Fillers are water soluble or insoluble materials incorporated into the formulation to add bulk. Types of fillers include, but are not limited to, NaCl, mannitol, sugars, synthetic polymers, modified starches and celluloses. The amount of filler in the formulation will typically be in the range of between about 1 and about 90% by weight.

Methods of Use

The present invention encompasses polymer conjugates for use in biomedical applications, primarily (but not exclusively) in the fields of pharmacology, bioengineering, wound healing, and dermatology/cosmetics. In certain embodiments, the polymer conjugates are biodegradable polyal conjugates. In particular, medical applications for the conjugates of the invention include injectable therapeutic pharmaceuticals, injectable diagnostic pharmaceuticals, gels, surgical implants, systems for controlled drug release, wound closure applications (sutures, staples), orthopedic fixation devices (pins, rods, screws, tacks, ligaments), cardiovascular applications (stents, grafts), and as long circulating and targeted drugs. Conjugates of the present invention can be employed as components of biomaterials, drugs, drug carriers, pharmaceutical formulations, medical devices, implants, and can be associated with small molecules, pharmaceutically useful entities, drugs, macromolecules and diagnostic labels.

Methods of Treating

In certain preferred embodiments of the invention, the conjugates of the invention are used in methods of treating animals (preferably mammals, most preferably humans). In one embodiment, the conjugates of the present invention may be used in a method of treating animals which comprises administering to the animal a biodegradable biocompatible conjugate of the invention. For example, conjugates in accordance with the invention can be administered in the form of soluble linear polymers, copolymers, conjugates, colloids, particles, gels, solid items, fibers, films, etc. Biodegradable biocompatible conjugates of this invention can be used as drug carriers and drug carrier components, in systems of controlled drug release, preparations for low-invasive surgical procedures, etc. Pharmaceutical formulations can be injectable, implantable, etc.

In yet another aspect, the invention provides a method of treating a disease or disorder in a subject in need thereof, comprising administering to the subject an efficient amount of at least one conjugate of the invention; wherein said conjugate releases one or more modifiers in a dual phase process; wherein said modifier(s) is(are) suitable therapeutic agent(s) for the treatment of the disease or disorder.

In yet another aspect, the invention provides a method of treating a disease or disorder in a subject in need thereof, comprising administering to the subject an efficient amount of at least one conjugate of the invention; wherein said conjugate is associated with a therapeutic agent; whereby:

the conjugate releases one or more modifiers in a dual phase process; wherein said modifier(s) is(are) suitable therapeutic agent(s) for the treatment of the disease or disorder; and wherein the therapeutic agent is incorporated into and released from biodegradable biocompatible polyketal matrix by degradation of the polymer matrix or diffusion of the agent out of the matrix over a period of time.

In certain embodiments, the modifier is locally delivered by implantation of said conjugate matrix at the desired site of delivery.

In certain other exemplary embodiments, any or more of the methods described above further comprises administering at least one additional biologically active compound.

In certain embodiments, the modifier, biologically active compound and therapeutic agent are independently selected from the group consisting of vitamins, anti-AIDS substances, anti-cancer substances, radionuclides, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, imaging agents, and combination thereof.

In certain embodiments, in practicing the method of the invention, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

In another aspect, the invention provides a method of treating a disease or disorder in a subject, comprising preparing an aqueous formulation of at least one conjugate of the invention and parenterally injecting said formulation in the subject. In certain exemplary embodiments, the conjugate comprises a biologically active modifier. In certain exemplary embodiments, the conjugate comprises a detectable modifier.

In another aspect, the invention provides a method of treating a disease or disorder in a subject, comprising preparating an implant comprising at least one conjugate of the invention, and implanting said implant into the subject. In certain exemplary embodiments, the implant is a biodegradable gel matrix.

In another aspect, the invention provides a method for treating of an animal in need thereof, comprising administering a conjugate according to the methods described above, wherein said conjugate comprises a biologically active modifier. In certain exemplary embodiments, the biologically active component is a gene vector.

In another aspect, the invention provides a method for eliciting an immune response in an animal, comprising administering a conjugate as in the methods described above, wherein said conjugate comprises an antigen modifier.

In another aspect, the invention provides a method of diagnosing a disease in an animal, comprising steps of:

administering a conjugate as in the methods described above, wherein said conjugate comprises a detectable modifier; and detecting the detectable modifier.

In certain exemplary embodiments, the step of detecting the detectable modifier is performed non-invasively. In certain exemplary embodiments, the step of detecting the detectable modifier is performed using suitable imaging equipment.

In one embodiment, a method for treating an animal comprises administering to the animal the biodegradable biocompatible conjugates of the invention as a packing for a surgical wound from which a tumor or growth has been removed. The biodegradable biocompatible conjugate packing will replace the tumor site during recovery and degrade and dissipate as the wound heals.

In certain embodiments, the conjugate is associated with a diagnostic label for in vivo monitoring.

The conjugates described above can be used for therapeutic, preventative, and analytical (diagnostic) treatment of animals. The conjugates are intended, generally, for parenteral administration, but in some cases may be administered by other routes.

In one embodiment, soluble or colloidal conjugates are administered intravenously. In another embodiment, soluble or colloidal conjugates are administered via local (e.g., subcutaneous, intramuscular) injection. In another embodiment, solid conjugates (e.g., particles, implants, drug delivery systems) are administered via implantation or injection.

In one embodiment, conjugates comprising a biologically active substance (e.g., a drug or a gene vector) are administered to treat disease responsive to said substance.

In another embodiment, conjugates comprising a detectable label are administered to study the patterns and dynamics of label distribution in animal body.

In another embodiment, conjugates comprising an antigen or an antigen-generating component (e.g., a plasmid) are administered to develop immunity to said antigen.

In certain embodiments, any one or more of the conjugates disclosed herein may be used in practicing any of the methods described above. In certain exemplary embodiments, the conjugate is a CPT-, Taxol- or Illudin-PHF conjugate.

Applications to Drug Delivery Methods

Examples of applications to drug delivery methods applicable to the present invention can be found inter alia in U.S. Provisional Patent Application 60/348,333; U.S. Utility patent application Ser. No. 10/501,565; European Patent No.: 03707375.6; and International Patent Applications PCT/US03/01017. These include Polyal-small-molecule-drug conjugates, protein-modified carriers, Cationized polyal, Polyal-modified liposomes, Polyal-modified nano- and microparticles.

In another embodiment, the biodegradable biocompatible conjugates of the present invention can be monitored in vivo by suitable diagnostic procedures. Such diagnostic procedures include nuclear magnetic resonance imaging (NMR), magnetic resonance imaging (MRI), ultrasound, X-ray, scintigraphy, positron emission tomography (PET), etc. The diagnostic procedure can detect, for example, conjugate disposition (e.g., distribution, localization, density, etc.) or the release of drugs, prodrugs, biologically active compounds or diagnostic labels from the biodegradable biocompatible conjugate over a period of time. Suitability of the method largely depends on the form of the administered conjugate and the presence of detectable labels. For example, the size and shape of conjugate implants can be determined non-invasively by NMR imaging, ultrasound tomography, or X-ray ("computed") tomography. Distribution of soluble conjugate preparation comprising a gamma emitting or positron emitting radiotracer can be performed using gamma scintigraphy or PET, respectively. Microdistribution of conjugate preparation comprising a fluorescent label can be investigated using photoimaging.

It is understood, for the purpose of this invention, that transfer and disposition of conjugates in vivo can be regulated by modifying groups incorporated into the conjugate structure, such as hydrophobic and hydrophilic modifiers, charge modifiers, receptor ligands, antibodies, etc. Such modification, in combination with incorporation of diagnostic labels, can be used for development of new useful diagnostic agents. The latter can be designed on a rational basis (e.g., conjugates of large or small molecules binding known tissue components, such as cell receptors, surface antigens, etc.), as well as through screening of libraries of conjugate molecules modified with a variety of moieties with unknown or poorly known binding activities, such as synthetic peptides and oligonucleotides, small organic and metalloorganic molecules, etc.

Interface Component

In one embodiment of the present invention, the biodegradable biocompatible conjugate can be used as an interface component. The term "interface component" as used herein, means a component, such as a coating or a layer on an object, that alters the character of the object's interaction with the biological milieu, for example, to suppress foreign body reactions, decrease inflammatory response, suppress clot formation, etc. It should be understood that the object can be microscopic or macroscopic. Examples of microscopic objects include macromolecules, colloids, vesicles, liposomes, emulsions, gas bubbles, nanocrystals, etc. Examples of macroscopic objects include surfaces, such as surfaces of surgical equipment, test tubes, perfusion tubes, items contacting biological tissues, etc. It is believed that interface components can, for example, provide the object protection from direct interactions with cells and opsonins and, thus, to decrease the interactions of the object with the biological system.

Surfaces can be modified by the biodegradable biocompatible conjugate of the present invention by, for example, conjugating functional groups of the conjugate polymer backbone with functional groups present on the surface to be modified. For example, aldehyde groups of biodegradable biocompatible polyal precursors can be reacted with amino groups present on the surface in the presence of cyanoborohydride to form amine linkages. In another embodiment, a biodegradable biocompatible polyal conjugate of the invention which includes a suitable terminal group can be synthesized, such as a polyal having a terminal aldehyde group. A polymer can be connected to a surface by reaction of the terminal group.

In still another embodiment, a suitable polysaccharide can be linked with a surface by reaction of a reducing or non-reducing end of the polysaccharide or otherwise, by subsequent oxidation/reduction sequence and further conversion of the remainder of the polysaccharide to produce a polyal conjugate.

It is to be understood that the biodegradable biocompatible conjugates of this invention can be conjugated with macromolecules, such as enzymes, polypeptides, proteins, etc., by the methods described above for conjugating the biodegradable biocompatible conjugates with functional groups present on a surface.

The biodegradable biocompatible conjugates of the invention can also be conjugated with a compound that can physically attach to a surface via, for example, hydrophobic, van der Waals, and electrostatic interactions. For example, the biodegradable biocompatible polyal precursors can be conjugated with lipids, polyelectrolytes, proteins, antibodies, lectins, etc.

In other embodiments of the present invention, biomedical preparations of the biodegradable biocompatible polyal conjugates of the invention can be made in various forms. It is believed that interface components can prolong circulation of macromolecular and colloidal drug carriers. Therefore, small molecules, biologically active compounds, diagnostic labels, etc., being incorporated in such carriers, can circulate throughout the body without stimulating an immunogenic response and without significant interactions with cell receptors and recognition proteins (opsonins). Accordingly, a conjugate of this invention can be further modified with an interface component (e.g., a polymer, such as polyethyleneglycol or a hydrophilic polyal) such that the drug carrying backbone of the conjugate is surrounded by a "brush" formed by the chains of said interface component. The latter can be additionally modified to enable conjugate targeting to a certain molecular marker, cell or tissue in vivo.

Throughout this document, various publications are referred to, each of which is hereby incorporated by reference in its entirety in an effort to more fully describe the state of the art to which the invention pertains.

The invention will now be further and specifically described by the following examples. All parts and percentages are by weight unless otherwise stated.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The practitioner has a well-established literature of polymer chemistry to draw upon, in combination with the information contained herein, for guidance on synthetic strategies, protecting groups, and other materials and methods useful for the synthesis of the conjugates of this invention.

The various references cited herein provide helpful background information on preparing polymers similar to the inventive compounds described herein or relevant intermediates, as well as information on formulation, uses, and administration of the conjugates of the invention, which may be of interest. Additional guidance may be found inter alia in (i) Papisov M I. Acyclic polyacetals from polysaccharides. ACS Symposium Series 786 (2001), 301-314; (ii) Cabodi S., Nenci A., Ong L, Papisov M, Dotto G-P. Targeted drug delivery to breast cancer cells. Proceedings, Dept of Defense Breast Cancer Research Program Meeting, Atlanta, Ga., 2000; v. 1 p. 307; (iii) M. I. Papisov, M. Yin, A. Yurkovetskiy, A. Hiller, S. Choi, A. J. Fischman. Fully biodegradable hydrophilic polyals (polyacetals and polyketals). 29th Int. Symp. on Controlled Release of Bioactive Materials, 2002, Seoul, Korea. Controlled Release Society, Deerfield, Ill., 2002; paper # 465; (iv) A. Yurkovetskiy, S. Choi, A. Hiller, M. Yin, A. J. Fischman, M. I. Papisov. Biodegradable polyal carriers for protein modification. 29th Int. Symp. on Controlled Release of Bioactive Materials, 2002, Seoul, Korea. Controlled Release Society, Deerfield, Ill., 2002; paper # 357; (v) M. Papisov, A. Yurkovetskiy, M. Yin, A. Hiller, A. J. Fischman. Fully biodegradable hydrophilic polyacetals for macromolecular radiopharmaceuticals. 49-th Annual Meeting of The Society of Nuclear Medicine, Los Angeles, Calif., 2002. J. Nuc. Med. 2002, 43:5 (Supplement) p. 377P; (vi) A. V. Yurkovetskiy, A. Hiller, M. Yin, S. Sayed, A. J. Fischman, M. I. Papisov. Biodegradable polyals for protein modification. Controlled Release Society's Winter Symposium, Salt Lake City, Utah, 2003; (vii) Papisov, A Yurkovetskiy, M Yin, P Leone, Alan J. Fischman, Alexander Hiller, and Sakina Sayed. Hydrophilic Polyals: Biomimetic Biodegradable Stealth Materials for Pharmacology and Bioengineering. Proceedings of 226th Natl. Meeting of American Chemical Society, New York, N.Y., 2003; (viii) A. V. Yurkovetskiy, A. Hiller, S. Sayed, M. Yin, X. M. Lu, A. J. Fischman, and M. I. Papisov. Synthesis of a macromolecular camptothecin conjugate with dual phase drug release. Molecular Pharmacology, 2004, in print.

Moreover, the practitioner is directed to the specific guidance and examples provided in this document relating to various exemplary conjugates and intermediates thereof.

The conjugates of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive conjugates or compositions including them. For example, a variety of solution phase synthetic methods such as those discussed in detail below may be used. Alternatively or additionally, the inventive conjugates may be prepared using any of a variety combinatorial techniques, parallel synthesis and/or solid phase synthetic methods known in the art.

It will be appreciated as described below, that a variety of inventive conjugates can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 140, John Wiley and Sons, New York, N.Y., 1991; March 2001, "Advanced Organic Chemistry", 5th ed. John Wiley and Sons, New York, N.Y.; Larock 1990, "Comprehensive Organic Transformations: A Guide to Functional Group Preparations", $2^{nd}$ ed. VCH Publishers; and other references more specifically drawn to polymer chemistry. The methods described below are merely illustrative of some methods by which the conjugates of this invention can be synthesized, and various modifications to these methods can be made and will be suggested to a person of ordinary skill in the art having regard to this disclosure.

The starting materials, intermediates, and conjugates of this invention may be isolated and purified using conventional techniques, including filtration, distillation, crystallization, chromatography, and the like. They may be characterized using conventional methods, including physical constants and spectral data Materials Sodium borohydride, sodium cyanoborohydride, sodium metaperiodate, 1-[3-(dimethylamino)propyl-3-ethylcarbodiimide hydrochloride (EDC), diethylenetriaminepentacetic acid (DTPA), 4-dimethylaminopyridine (DMAP) and succinic anhydride were from Aldrich, St Louis, Mo. $InCl_3$ [In-111] was from Perkin Elmer Life Sciences (Boston, Mass.). Anhydrous pyridine, ethyl alcohol, and other solvents were obtained from Sigma-Aldrich and used without further purification.

Camptothecin was obtained from Hande Tech development Co. (Houston, Tex.). Dextran B-512 (Mn 73,000 Da, 188,000 Da) and N-BOC-glycine were obtained from Sigma Chemical Company (St Louis, Mo.). Succinic anhydride (SA), sodium borohydride, sodium metaperiodate, 1-[3-(dimethylamino)propyl-3-ethylcarbodiimide hydrochloride (EDC), diisopropylcarbodiimide (DIPC), 4-dimethylaminopyridine (DMAP), trifluoroacetic acid, hydrochloric acid and sodium hydroxide were purchased from Aldrich (St Louis, Mo.). Other chemicals, of reagent or higher grade, were obtained from Acros Organics or Fisher Scientific and used as received. Anhydrous pyridine, methyl alcohol, ethyl alcohol, dimethylformamide, dimethylsulfoxide, methylene chloride, diethyl ether and other solvents were obtained from Sigma-Aldrich and used without further purification. Deionized water (resistivity>18 MΩ) was used for all synthetic and analytical procedures.

Equipment and Methods

Size exclusion chromatography (SEC) in aqueous media and reversed phase (RP) chromatography were carried out using a Varian-Prostar HPLC system equipped with a BIO-RAD model 1755 Refractive Index detector and LDC/Milton Roy SpectoMonitor 3000 UV detector. HPSEC Biosil SEC-125 and Biosil SEC400 (BIO-RAD), and low-pressure Superose-6 (Pharmacia) columns were used for size exclusion chromatography. SEC column calibration was performed based on broad molecular weight dextran and protein standards. Unless otherwise stated, elution was performed isocratically with 50 mM phosphate buffered 0.9% NaCl, pH=7.0.

An Altima C18 column (Alltech, 250 mm×4.6 mm, 5 μm bead) was used for RP chromatographic determination of low molecular weight CPT derivatives and degradation products of polymer-CPT conjugates.

Preparative isolation and purification of polymers and polymer conjugates was carried on a G-25 gel SpectraChrom (60 cm×ID 10 cm) column equipped with a Milton-Roy liquid delivery system, MasterFlex CL peristaltic pump, Knauer-2401 RI detector, Foxy JR fraction collector and Varian-Prostar data acquisition system. Alternatively, a QuixStend flow dialysis system (A/G Technology, Needham, Mass.)

equipped with a UFP-10-C-4MA hollow fiber cartridge (cutoff 10 kDa) was used in high volume procedures. Photon correlation light scattering was carried out using a Brookhaven ZetaPlus analyzer.

Proton and $^{13}$C NMR were carried out on Varian Mercury-300, Bruker DPX-300, and Bruker Aspect 3000 NMR spectrometers using solvent peak as reference standard.

A Cary 300Bio UV-visible spectrophotometer equipped with thermostated multi-cell Peltier block, and Molecular Devices Co. 96-well Plate Reader was used for spectroscopic measurements and enzyme kinetics studies.

An Agilent 1100 series LC/MSD system was used for MS characterization of PHF-CPT hydrolysis products.

Male nu/nu mice, 18-24 g (8-10 week of age) were obtained from Charles River Laboratories, MA.

Human colorectal adenocarcinoma HT-29 cell culture was from ATCC (ATCC HTB-38).

Photoimaging was carried out using Nikon Eclipse TE300 microscope with long working distance phase contrast optics, epifluorescence imaging setup, CCD camera, and MacOS based imaging workstation.

Radioactivity measurements were carried out using Wallac Wizard 1480 gamma counter (Perkin Elmer). Gamma scintigraphy was performed using Ohio Nuclear gamma camera with medium energy collimator.

PHF-CPT Conjugates

As discussed above, biodegradation of macromolecular therapeutics is an important but incompletely studied issue, even for most widely used polymers. For example, there is a potential risk that extended clinical use of conjugates containing non- or slow-biodegradable polymer fragments can lead to long-term cell vacuolization (see, for example, Bendele A. Seely J. Richey C. Sennello G. Shopp G. (1998) Short communication: renal tubular vacuolation in animals treated with polyethylene-glycol-conjugated proteins. *Toxicological Sciences*. 42, 152-7) and overload, development of lysosomal disease syndrome (see, for example, Christensen, M., Johansen, P., Hau C., (1978) Storage of polyvinylpirrollidone (PVP) in tissue following long-term treatment with a PVP-containing Vasopressin preparation. *Acta Med. Scand.*, 204, 295-298), and, at higher doses, to other pathological metabolic alterations (see, for example, Miyasaki K. (1975) Experimental Polymer Storage Disease in Rabbits. *Virchows Arch. A. Path. Anat. And Histol.*, 365, 351-365). Development of essentially completely biodegradable polymers, preferably degrading with formation of low-toxicity, readily clearable or metabolizable products, appear to be the predominant possible radical solution of the problem of long-term intracellular deposition. A combination of a macromolecular material and a cross-linking reagent enabling sufficient conjugate stability in the normal extracellular environment and, on the other hand, acceptable rate of conjugate disintegration upon endocytosis, would be most beneficial.

Hydrophilic essentially fully degradable polyals, e.g., poly[1-hydroxymethylethylene hydroxymethyl-formal] (PHF), have been developed and reported as acyclic mimetics of polysaccharides (see, for example, (1) Papisov M I, Garrido L, Poss K, Wright. C, Weissleder R, Brady T J. (1996) A long-circulating polymer with hydrolizable main chain. 23-*rd International Symposium on Controlled Release of Bioactive Materials, Kyoto, Japan, 1996; Controlled Release Society, Deerfield, Ill.*,; 107-108; and (2) Papisov M. I. (1998) Theoretical considerations of RES-avoiding liposomes. *Adv. Drug Delivery Rev.*, 32, 119-138). These materials, which can be prepared synthetically and by lateral cleavage of some polysaccharides, were shown to be essentially (i) non-bioreactive, (ii) non-toxic and (iii) fully degradable, and, thus, proved to have potential in various pharmaceutical applications (see, for example, (1) Papisov M I, Babich J W, Dotto P, Barzana M, Hillier S, Graham-Coco W, Fischman A J. (1998) Model cooperative (multivalent) vectors for drug targeting. 25*th Int. Symp. on Controlled Release of Bioactive Materials, 1998, Las Vegas, Nev., USA; Controlled Release Society, Deerfield, Ill.*, 170-171; and (2) Papisov M I. (2001) Acyclic polyacetals from polysaccharides. (Biopolymers from polysaccharides and agroproteins), *ACS Symposium Series* 786, pp. 301-314). Polyals contain pH-sensitive acetal or ketal groups within the main chain, which provides the desired combination of polymer stability in neutral and alkaline media and destabilization in acidic environment.

In certain embodiments, the present invention further expands the scope of potential applications for hydrophilic polyals, and demonstrates suitability of these materials for preparation of essentially fully degradable carrier-drug conjugates in dual phase drug release systems. In certain exemplary embodiments, a hydrophilic polyal (PHF) is used to obtain and characterize PHF-CPT conjugates.

Camptothecin[1] (CPT) is a potent antineoplastic agent with topoisomerase I inhibiting activity. Therapeutic application of unmodified CPT is hindered by very low solubility in aqueous media, high toxicity, and rapid inactivation through lactone ring hydrolysis in vivo. Lactone hydrolysis, which is reversible in acidic media, leads to a water soluble carboxylate.[2] The latter is cleared by the kidneys and causes hemorrhagic cystitis, a severe adverse reaction to CPT administration. Acylation of the (O20) lactone ring hydroxyl significantly increases the stability.[3,4]

Hydrophilization of the CPT molecule results in water soluble forms, e.g. Irinotecan (CPT-11). The latter is the most widely used soluble prodrug, which (as well as other CPT prodrugs) require endoplasmic activation, mainly in the liver, for conversion into the active form (SN38[5]). Such prodrugs, activated outside cancer tissue, are not feasible for tumor as well as cancer cell targeting.

Macromolecular and liposomal forms of CPT have shown improved efficacy, as compared to low molecular weight analogs.[6,7] However, bladder toxicity was still reported.[8] The dual phase drug release system described in this paper was intended to engineer soluble, potentially targetable macromolecular preparations with novel pharmacokinetics and reduced toxicity.

The dual phase strategy involves assembling of a hydrophilic conjugate that releases a lipophilic stabilized CPT prodrug, which, in turn, releases the active drug substance locally (intra- and extracellularly), without the need for prior metabolization by the hepatic microsomal P450 complex.

The model release system developed in this work is based on a known reaction, hydrolytic cyclization of succinamidoesters. The reaction results in ester bond cleavage and simultaneous succinimide formation at the amide side. Attempts have been made to employ succinamidoester linkers with the amide group at the carrier side,[9] which does not result in dual phase drug release. In our system, the succinamidoester is oriented such that the ester is formed at the polymer side, while the opposite carboxyl forms an amide bond with an amine-containing drug or drug derivative (in this paper, CPT-(O20)-glycinate).

Hydrolysis of the succinamidoester linker leads to drug cleavage from the polymer in the form of a cyclic succinimidoglycyl-CPT (Scheme 2). The reaction is base catalyzed, and in aqueous medium goes to completion under mild conditions. The second stage is in vivo glycyl ester bond hydrolysis, which results in active drug release.

Potential advantages of this dual phase drug release system, as applied to CPT, include: (1) The conjugate is water soluble, and can be administered intravenously. (2) Unlike other CPT prodrugs, e.g. Irinotecan, the intermediate prodrug is activated "on site" rather than in the liver, so that local administration and targeting are possible. (3) CPT is released in a lipophilic, lactone-stabilized form, which ensures prodrug deposition in tissues and low rates of redistribution and carboxylate transfer to urine.

In this paper, a model fully biodegradable macromolecular CPT conjugate with dual phase release from an unsubstituted succinamidoester linker was synthesized and characterized in vitro. Initial results of ongoing in vivo characterization studies are also presented.

The conjugate was assembled using poly(1-hydroxymethylethylene hydroxy-methyl formal) (PHF) as a backbone. PHF is a highly hydrophilic, biodegradable "stealth" polymer developed in our laboratory.[10,11] Biodegradability of PHF reduces the potential risks associated with administration of large doses of non-degradable polymers, making the model PHF conjugate feasible for clinical development.

EXAMPLE 1

PHF

PHF is a semi-synthetic acyclic polyacetal prepared by exhaustive lateral cleavage of Dextran B-512. Complete periodate cleavage of the (1->6)-polyglycoside sequence of Dextan B-512 results in poly(1-carbonylethylene carbonyl formal) (PCF). Borohydride reduction of the pendant aldehyde groups of PCF gives poly(1-hydroxymethylethylene hydroxy-methyl formal) (PHF), a copolymer (copolyacetal) of glycerol and glycol aldehyde (See structure below). Incomplete cleavage at the oxidation stage results in the presence of vicinal glycol groups in place of some of the methylol groups, which is in some instances desirable. An even lower degree of cleavage results in the presence of both glycol groups and some intact carbohydrate rings in the polymer chain.

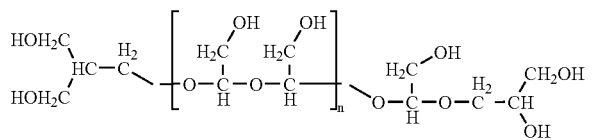

Properties of PHF include the following:

PHF is a highly hydrophilic, water soluble polymer, stable in physiological conditions, but undergoing proton-catalyzed hydrolysis at lysosomal pH.

The polymer showed no toxicity in mice at doses up to 4 g/kg IV and IP (higher doses not studied). Upon IV administration, low molecular weight PHF (<50 kDa) is almost completely cleared by kidneys with no significant accumulation in any tissues.

High molecular weight PHF and derivatives (PHF modified macromolecules and model drug carriers) that are not cleared by kidneys circulate with half-lives up to 10-25 hours (rodents), with a nearly uniform final distribution (accumulation per g tissue in RES only twice higher than in other organs). The latter suggests lack of recognition by phagocytes, other cells and recognition proteins ("stealth" properties[27])

PHF was prepared, at multi-gram scale, in a variety of molecular weights. The chemical structure of PHF enables a wide variety of modifications and derivatizations, via pendant OH groups as well as via at least one terminal vicinal glycol group.[28] Several PHF derivatives were synthesized and characterized as model biomedical preparations (protein and small molecule conjugates, gels, long-circulating drug carriers, etc.).[28,29,30,31,32,33,34]

Due to the "stealth" properties, biodegradability profile, and technological flexibility, PHF is a highly promising material for several pharmaceutical and bioengineering applications. In particular, the biodegradability and multifunctionality of PHF eliminate several limitations on the size and structure of small molecule conjugates, enabling, for example, high dose administration of high molecular weight conjugates (>50 kDa) without the risk of long term polymer depositions in cells.

Several clinically relevant model preparations of PHF developed in our laboratory at MGH were evaluated in collaborative studies with the pharmaceutical industry. Various aspects of polyacetal technology were co-developed with, or licensed by MGH to Novartis, Amgen, and Nanopharma.

Additional guidance for the preparation of PHF polymeric material can be found, inter alia, in PCT/US03/22584.

The polymer was prepared using an accelerated modification of a previously described technique[12] allowing the formation of PHF with 5% 2,3-dihydroxyethylformal units originating from the C2-C3 of dextran. Dextran B-512, 73 kDa preparation (15.15 g, 93.4 mmol by glycopyranoside), was dissolved in 300 ml of deionized water at 0-5° C. and treated with 47.95 g (224.2 mmol) of sodium metaperiodate in a light protected reactor for 3 hours. The crystalline sodium iodate was removed from the reaction mixture by filtration (1μ glass filter). The pH of the filtrate was adjusted to 8.0 with 5N NaOH and the resultant solution was immediately treated with sodium borohydride (7.07 g, 187 mmol, dissolved in 70 ml of deionized water) for 2 hours. The pH was then adjusted to 6.5 with 1 N HCl. The product was desalted on Sephadex G25 and lyophilized; yield: 80%. The results of SEC analysis were Mn=60 kDa and polydispersity index (Mw/Mn) of 2.0. Proton NMR spectrum in DMF-$d_6$:$D_2O$ (95:5 v/v) was found to be in agreement with the expected PHF structure (C1-H at δ 4.62 t, J=5.2 Hz) with ca 5% vicinal diol pendant groups originating from C2-C3(δ 4.49 d, J=5.2 Hz).

EXAMPLE 2

CPT-20-(O)-glycinate trifluoroacetate salt (CPT-Gly.TFA)

CPT-Gly.TFA, was prepared in two steps according to the procedure reported by Greenwald[12,14] and modified by Minko[1e]. Briefly, CPT was treated with BOC-glycine and DIPC in methylenechloride in the presence of DMAP. The N-BOC group was removed with trifluoroacetic acid, and the resultant CPT-Gly.TFA was crystallized from diethyl ether. Purity: >97% (HPLC, NMR).

EXAMPLE 3

PHF-Succinate (PHF-SA)

PHF (10.00 g, 75.6 mmol), succinic anhydride (0.76 g, 7.6 mmol) and DMAP (1.2 mg, 0.01 mmol) were dissolved in 5 ml of anhydrous pyridine. After 18 hours of agitation at 40° C., pyridine was removed in vacuum, the residue was suspended in deionized water, and the pH was adjusted to 7.0 with 1 N NaOH. The succinylated PHF was desalted on Sephadex G-25 and lyophilized with 86% yield. The succinic acid content, as determined by potentiometric titration, was 10.3% (mol/monomer). The $^1$H NMR spectrum of the polymer (D$_2$O) contained signals characteristic for methylene protons of succinic acid ester at δ 2.66 and δ 2.57 (broad triplets) in addition to methylene and methine (δ 3.3-3.8), and acetal (δ4.4-4.7) protons of the PHF backbone.

EXAMPLE 4

Camptothecin-PHF Conjugate (PHF-CPT)

Conjugation of CPT-Gly.TFA with PHF-SA was conducted via (i) EDC mediated amidation of polymer-succinate with CPT-20-O-glycinate trifluoroacetate salt in aqueous medium, or (ii) DIPC mediated coupling in non-aqueous conditions (DMF). The first approach (described below) was found to be more efficient, based on higher reaction rate, cleaner product and simplicity of purification.

Prior to the preparative synthesis, conjugates with various CPT contents (ca. 5% to 15% w/w) were prepared on a lower scale to test solubility in aqueous media, which showed that conjugates with CPT content up to 10% w/w were readily soluble.

Preparative synthesis. PHF-SA (15.0 g, 10.7 mmol SA) was dissolved in 150 ml of deionized water and mixed with 30 ml of DMF, cooled to −2° C., and combined with CPT-Gly.TFA solution (2.0 g/3.85 mmol in 20 ml of 3:1 acetonitrile/water mixture). Under intense agitation, EDC (2.0 g) was added to the reaction mixture. The pH was adjusted to 5.9-6.0. After 30 minutes of agitation, the temperature of the reaction mixture was brought to ambient, and agitation was continued for another 3 hours. The CPT conversion at this point was 93%, based on RP HPLC (UV at 360 nm). The pH was adjusted to 5.5 to prevent CPT release from the conjugate, and the reaction mixture was stored overnight at 8° C. The mixture was then diluted with DMF and water to 600 ml (DMF content 10% v/v), and the conjugate was desalted on Sephadex G-25, lyophilized, and stored at −20 C.°. The product was obtained as an off-white to pale-yellow solid with CPT content of 7.48% w/w (as determined spectrophotometrically at 360 nm). Yield based on CPT: 80%.

Proton NMR spectrum of PHF-CPT (DMSO-d$_6$/D$_2$O) contained the signals characteristic for the succinic acid modified PHF backbone: δ 3.3-3.8 (methylene and methine), δ4.4-4.7 (acetal), δ 2.4-2.6 (—CH$_2$—, succinate); and signals corresponding to the pendant CPT structures: δ 0.95 (t), δ 2.21 (d), δ 5.26(m), δ 5.46(s), δ 7.20(s), δ 7.70(t), δ 7.88(t), δ 8.09(d), δ 8.18(d), δ 8.45(s).

The reaction mixture and lyophilized product compositions are shown in Table 1.

TABLE 1

PHF-CPT conjugate composition (by CPT, mol %).

| # | CPT derivatives | Reaction mixture | Isolated product |
|---|---|---|---|
| 1 | PHF-CPT | 92.8 | 96.15 |
| 2 | CPT-Glycinate | 1.9 | 0.32 |
| 3 | CPT | 2.3 | 0.34 |
| 4 | CPT-CA (carboxylate) | 0.3 | 0.44 |
| 5 | CPT-Gly-SA | <0.05 | 0.53 |
| 6 | CPT-Gly-SI | <0.05 | 0.66 |
| 7 | Other low MW | 2.7 | 1.59 |

The synthesized PHF-CPT was soluble in aqueous media. HPSEC showed Mn of ~65 kDa with essentially no aggregation (photon correlation light scattering). The viscosities of up to 20% solutions were feasible for injection through a high gauge needle used in the rodent studies; most injections were performed at 6% w/w (η=4.05 cps).

EXAMPLE 5

Camptothecin-20-(N-succinimidoglycinate) (CPT-SI)

CPT-SI is the lipophilic prodrug isolated from the products of PHF-CPT hydrolysis (see below). CPT-SI was synthesized as a control compound.

PHF-CPT (500 mg) was dissolved in 10 ml of 0.1M phosphate pH 7.6 and incubated for 24 hours at 37° C. The resultant suspension was diluted to 150 ml and extracted with methylene chloride (3×150 ml). Methylene chloride layers were combined, washed with 0.01 N HCl, and dried over magnesium sulfate. Solvent was removed in vacuum. The light yellow residue was redissolved in methylene chloride, filtered and dried in vacuum to yield 38 mg of a product containing, according to RP HPLC, >93% CPT-SI. Solubility of CPT-SI in water was found to be lower than that of unmodified CPT, <1.0 µg/ml, vs. 2.5 µg/ml respectively.

$^1$H NMR (300 MHz, CDCl$_3$): δ 1.01(τ, 3H, J=7.4 Hz, C19), δ 2.05-2.32 (m, 2H, C18), δ 2.66 (s, 4H, succinimide), δ 4.32-4.51(AB, 2H, 17.2 Hz, C-α Gly), δ 5.32 (s, 2H, C-5), δ 5.29-5.65 (AB, 2H, 17.3 Hz, C-17), δ 7.20 (s, 1H, C-14), δ 7.60 (t, 1H, J=7.5 Hz, C-11), δ 7.76 (t,1H, J=7.7 Hz), δ 7.86 (d, 1H, J=8.3, C-12), δ 8.20 (d, 1H, J=8.3, C-9), δ 8.32(s, 1H, C-7)

$^{13}$C NMR: 7.23, 28.36, 29.89, 32.04, 39.53, 50.17, 67.31, 77.45, 96.29, 120.54, 128.23, 128.33, 128.64, 130.00, 130.80, 131.35, 145.14, 146.70, 149.08, 152.46, 157.48, 166.27, 166.78, 175.95.

MS: m/z 488.2 (M+H)

EXAMPLE 6

Camptothecin-20-(N-succinamidoglycinate) (CPT-SA, control)

CPT-Gly.TFA (50 mg, 0.096 mmol) and succinic anhydride (18 mg, 0.190 mmol) were dissolved in 2 ml of anhydrous pyridine. After an 18 hour agitation at ambient temperature, pyridine was removed in vacuum. The solid residue was suspended in deionized water and extracted with methylene chloride, washed with 0.01N HCl and dried over magnesium sulfate. Solvent removal in vacuum resulted in a light-yellow solid (41.4 mg, 85% yield) containing >90% CPT-SA (HPLC with 360 nm detection). LC-MS: m/z 506.2 (M+H). The product was used as HPLC standard for determination of PHF-CPT hydrolysis product composition.

EXAMPLE 7

Preparation of Succinylated Polyacetal Carriers

Polyacetal carriers modified with a substituted succinyl group were prepared according to a procedure analogous to that described above for PHF-SA. Briefly, treatment of anhydrous PHF Mn 60 kDa (10.0 g) in 100 ml of dry pyridine with calculated amount of succinic anhydride derivative (see Table 2) and DMAP (anhydride:DMAP=1:0.1 mol ratio) for 18 hours at 40° C. afforded quantitative conversion of succinic acid derivative into corresponding PHF-succinate with degree of PHF structural unit substitution of approximately 10% (mol). After pyridine evacuation in vacuum PHF-succinates were dissolved in DI water and purified of low molecular weight impurities by gel filtration on Sephadex G-25 column equilibrated with DI water. Final product was recovered from aqueous solution by lyophilization as foam with average 85-90% yield. The obtained PHF-succinates are hydrophilic polymers readily soluble in water and polar organic solvents (pyridine, DMF, DMSO). Polymer yield, composition, and succinate content are reported in Table 2.

TABLE 2

Composition and properties of succinylated PHF carriers

| Modified polyacetal | Succinic acid derivative | Polymer substitution (calculated) % mol | Succinate content* mol/g polymer | Polymer yield, % |
|---|---|---|---|---|
| PHF-SA | Succinic anhydride | 10 | $7.0 \times 10^{-4}$ | 86 |
| PHF-MSA | Methylsuccinic anhydride | 10 | $6.9 \times 10^{-4}$ | 88 |
| PHF-DMSA | 1,1-Dimethylsuccinic anhydride | 10 | $6.8 \times 10^{-4}$ | 85 |
| PHF-NSA | (2-Nonen-1-yl) succinic anhydride | 15 | $8.9 \times 10^{-4}$ | 89 |
| PHF-DSA | (2-Dodecen-1-yl) succinic anhydride | 15 | $8.6 \times 10^{-4}$ | 91 |

*Potentiometric titration

EXAMPLE 8

(2-Nonen-1-yl)-succinic Acid-Linked PHF-CPT (PHF-NSA-CPT)

PHF-(2-nonenylsuccinate) (PHF-NSA) (2.5 g, 2.23 mmol NSA) was dissolved in 50 ml of deionized water and mixed with 20 ml of DMF, cooled down to 0° C., and combined with CPT-Gly.TFA solution (454 mg/0.848 mmol) in 15 ml of 4:1 acetonitrile/water mixture). Under intense agitation, EDC (500 mg) was added to the reaction mixture. The pH was adjusted to 5.9-6.0. After 30 minutes of agitation, the temperature of the reaction mixture was brought to ambient; agitation continued for another 3 hours. The CPT-Gly.TFA conversion after 3 hours monitored by HPLC (UV at 360 mm) was >92%. The reaction mixture was then diluted with 1:9 v/v DMF/water mixture to 150 ml, and the pH of the resulting solution was adjusted to 5.5. The obtained conjugate was desalted on Sephadex G-25 and lyophilized. The product was obtained as off-white to pale-yellow solid soluble in water and polar organic solvents (pyridine, DMF, DMSO). CPT conjugate content determined spectrophotometrically at 360 nm was 13.0% w/w. Yield based on CPT: >95%. Residual carboxyl group content in the conjugate was $4.1 \times 10^{-4}$ mol/g.

Proton NMR spectrum of PHF-NSA-CPT (DMSO-$d_6$/$D_2O$) contained the signals characteristic for noneneylsuccinic acid modified PHF backbone: δ 3.3-3.8 (methylene and methine, PHF), δ4.4-4.7 (acetal), δ 2.6-2.7 (—$CH_2$—, succinate), δ 0.96(t) (—$CH_3$, noneneyl), δ1.25-1.35 (—$CH_2$—, noneneyl), δ 5.65 and δ5.75. (—CH═, noneneyl); and signals corresponding to the pendant CPT structures: δ 0.95 (t), δ 2.22 (d), δ 5.26(m), δ 5.46(s), δ 7.20(s), δ 7.71(t), δ 7.89(t), δ 8.10(d), δ 8.18(d), δ 8.45(s).

EXAMPLE 9

Methylsuccinic acid-linked PHF-CPT (PHF-MSA-CPT)

PHF-(methylsuccinate) (PHF-MSA) (2.5 g, 1.72 mmol MSA) was dissolved in 50 ml of deionized water and mixed with 20 ml of DMF, chilled down to 0° C., and combined with CPT-Gly.TFA solution (450 mg/0.840 mmol) in 15 ml of 4:1 acetonitrile/water mixture). Under intense agitation, EDC (500 mg) was added to the reaction mixture. The pH was adjusted to 5.9-6.0. After 30 minutes of agitation, the temperature of the reaction mixture was brought to ambient; agitation continued for another 3 hours. The CPT-Gly.TFA conversion after 3 hours monitored by HPLC (UV at 360 nm) was >90%. The reaction mixture was then diluted with 1:9 v/v DMF/water mixture to 150 ml, and the pH of the resulting solution was adjusted to 5.5. The obtained conjugate was desalted on Sephadex G-25 and lyophilized. The product was obtained as off-white to pale-yellow solid soluble in water, saline and polar organic solvents (DMF, DMSO), intrinsic pH 5.7. CPT conjugate content determined spectrophotometrically at 360 nm was 7.65% w/w. Yield based on CPT: 71%. Residual carboxyl group content in the conjugate was $3.0 \times 10^{-4}$ mol/g.

Proton NMR spectrum of PHF-NSA-CPT (DMSO-$d_6$/$D_2O$) contained signals characteristic for methylsuccinic acid modified PHF backbone and pendant CPT structures.

EXAMPLE 10

1,1-Dimethylsuccinic acid-linked PHF-CPT (PHF-MSA-CPT)

PHF-(1,1-dimethylsuccinate) (PF-DMSA) (2.5 g, 1.70 mmol DMSA) was dissolved in 50 ml of deionized water and mixed with 20 ml of DMF, chilled to 0° C., and combined with CPT-Gly.TFA solution (450 mg/0.840 mmol) in 15 ml of 4:1 acetonitrile/water mixture). Under intense agitation, EDC (500 mg) was added to the reaction mixture. The pH was adjusted to 5.9-6.0. After 30 minutes of agitation, the temperature of the reaction mixture was brought to ambient; agitation continued for another 3 hours. The CPT-Gly.TFA conversion after 3 hours monitored by HPLC (UV at 360 nm) was >90%. The reaction mixture was then diluted with 1:9 v/v DMF/water mixture to 150 ml, and the pH of the resulting solution was adjusted to 5.5. The obtained conjugate was desalted on Sephadex G-25 and lyophilized. The product was obtained as off-white to pale-yellow solid soluble in water, saline and polar organic solvents (DMF, DMSO), intrinsic pH 5.7. CPT conjugate content determined spectrophotometrically at 360 nm was 6.9% w/w. Yield based on CPT ca. 65%. Residual carboxyl group content in the conjugate was $2.9 \times 10^{-4}$ mol/g.

Proton NMR spectrum of PHF-NSA-CPT (DMSO-$d_6$/$D_2O$) contained the signals characteristic for dimethylsuccinic acid modified PHF backbone and pendant CPT structures.

EXAMPLE 11

PHF-CPT Hydrolysis

The hydrolytic stability of PHF-CPT conjugate was tested in DI water and isotonic saline at ambient temperature and pH=5.7, in 0.05M phosphate buffered 0.9% saline (pH 7.4), and in freshly prepared rat plasma at 37° C. PHF-CPT hydrolysis and accumulation of CPT derivatives was monitored by RP HPLC using a 20-minute 10-70% acetonitrile/ water gradient (both solvents with 0.1% TFA). Results were reproduced in two independent experiments.

The second stage hydrolysis of CPT-SI was investigated analogously.

The reaction of cyclization-elimination (Scheme 2) involves folding of the succinamidoester into a cyclic intermediate structure, with subsequent intramolecular nucleophilic attack on the ester carbon. Thus, the reaction should be sensitive to the presence of (1) bulky substituents and (2) substitutents altering the charge density on either of the carboxylic carbons of the linker. The second phase can also be affected by the substitutents in the succinimide ring of the prodrug. Therefore, substitution in the succinate linker can be a powerful tool for regulation of the drug release profile. Furthermore, substitution in the succinate linker can open the way to regulation of prodrug properties (hydrophobicity, transmembrane transfer, affinity to cell receptors, etc.), which can further enhance pharmacokinetics.

Other substituted analogs of PHF-CPT synthesized using methyl-, 2,2-dimethyl, and 2-nonen-2-yl succinates as described in Examples 7-10. Using procedures analogous to the described above, CPT release from these conjugates was investigated in phosphate buffered saline as described above. The conjugates were also tested for cytotoxicity in HT29 cell culture.

The PHF-CPT solutions (intrinsic pH=5.5-5.7 with physiologically negligible buffer capacity) showed no significant decomposition after a week of storage at 8° C. or 24 hours at ambient temperature. At neutral and slightly basic pH (7.0-7.4) and mild conditions (8-37° C.), the conjugate did undergo slow hydrolysis yielding primarily CPT-20-O-(N-succinimidoglycinate) (CPT-SI). For example, hydrolysis of PHF-CPT conjugate (2 mg/ml in 0.05M phosphate buffered 0.9% saline pH 7.4 for 24 hours) resulted in the quantitative release of CPT from PHF-CPT, with CPT-SI lactone (87%), CPT carboxylate (8%) and CPT-SA lactone (5%) being the only detectable products. Notably, CPT released from the prodrug under these conditions was in the carboxylate but not lactone form, suggesting that the lactone ring, which was stable in CPT-SI and CPT-SA, was hydrolyzed during the second stage of CPT release.

A similar trend but slightly different composition of hydrolytic products was observed in freshly prepared rat plasma, as shown on FIG. 1. This suggests the presence of additional CPT release mechanisms, possibly mediated by interactions with plasma proteins. Cleavage of CPT (all forms) from PHF-CPT was found to be monoexponential, with half-release time of 2.2±0.1 hours.

The half-time of the subsequent hydrolysis of CPT-SI was over 20 hrs, depending on the conditions (the exact pH dependence and enzyme sensitivity, if any, are to be determined in ongoing studies).

The three synthesized substituted analogs of PHF-CPT were also investigated to determine the first phase release rates. As expected, the bulky nonenyl group (which sterically hinders linker folding, which is necessary for hydrolytic cyclization) decreased the release rate, while methyl groups, which stabilize cyclic structures, increased it (Table 3; each result based on two independent experiments, n=4-6 data points each; for all numbers SD<10% of the mean, p<0.05).

TABLE 3

Comparative release rates of modified CPT-PHF conjugates in PBS at pH 7.4/37° C.

| Compound | Linker | CPT half-release time, hours |
| --- | --- | --- |
| PHF-CPT | Gly-succinate | 2.1 |
| PHF-MSA-CPT | Gly-(methyl succinate) | 1.4 |
| PHF-DMSA-CPT | Gly-(2,2-dimethyl succinate) | 0.6 |
| PHF-NSA-CPT | Gly-(2-nonen-2-yl succinate) | 16.0 |

EXAMPLE 12

PHF-SAG-Taxol Conjugate

The water soluble Taxol conjugate with PHF utilizing dual-phase release succinamidoglycine linkage, PHF-succinamidoglycine-Taxol conjugate (PHF-SAG-Taxol), has been prepared from Taxol-2'(O)-glycinate and succinilated PHF.

Taxol-2'(O)-glycine-$NH_2$ was obtained in two steps via acylation of Taxol with HO-Gly-(Z) (DIPC, DMAP, $CH_2Cl_2$) followed by amino group deprotection ($H_2$, Pd/C, MeOH) with overall 60% yield [Z=Cbz]. Taxol-2'(O)-Gly-$NH_2$ was conjugated to PHF-succinate (10% mol. succinic acid, MW 65 kDa) via EDC mediated coupling in 50% aqueous DMF. PHF-SAG-Taxol conjugate synthesis was carried out on a 2-gram scale, at ambient temperature, pH 5.5-6.0. A quantitative (>98%) Taxol-glycinate conversion to PHF-SAG-Taxol was detected within 3 hours. The PHF-SAG-Taxol was purified of low molecular weight impurities by gel filtration on G25 Sefadex column equilibrated with DI water, and recovered by lyophilyzation. Following the above procedure, conjugates with Taxol load ranging from 6% to 13% (wt.) were prepared. All products were readily soluble in deionized water and saline. Stability of PHF-Taxol conjugates in aqueous media was monitored by HPLC. Aqueous solutions of PHF-SAG-Taxol were stable at ambient conditions in pH range from 4.5 to 5.5. At physiological conditions (PBS, pH 7.4, 37° C.) the drug was released from the conjugate with a half-life of 1.5±0.2 hours, resulting in a mixture of Taxol-2'(O)-(succinimidoglycine) and Taxol at a ratio of 1.5:1.0. Under these conditions, Taxol-2'(O)-(succinimidoglycine) ester hydrolyzed to Taxol with half-life of approximately 3 hours. Antitumor activity of PHF-SAG-Taxol preparation with Taxol content of 13% was tested in vitro with HT-29 human colorectal carcinoma cells. Both PHF-Taxol conjugate and unmodified Taxol formulations have shown statistically identical cell growth inhibitory efficacy (ED50 15 nM).

EXAMPLE 13

Glycyl-Illudin

Illudin M, 50 mg (0.2 mmol), was dissolved in 2 mL of anhydrous THF and cooled to 0° C. Then, 65 mg (0.22 mmol) of Fmoc-glycine, 30 mg (0.22 mmol) of diisopropyl carbodiimide, and 1 mg of 4-(dimethylamino)pyridine (DMAP) were added. The reaction mixture was stirred at 0° C. for 2 hours, then overnight at ambient temperature. The resultant Fmoc-glycyl-illudin was purified by column chromatography (silica, chloroform with 1% ethanol) and dried in vacuum. Yield: 73 mg (70%).

Fmoc-glycyl-illudin (30 mg) was dissolved in 5 mL of 20% piperidine in DMF. The solution was stirred at ambient temperature for 3 hours. The solvent was removed under vacuum, and the resultant glycyl-illudin was purified by column chromatography (silica, chloroform with 3% ethanol and 1% triethylamine). Yield: 10 mg (57%).

EXAMPLE 14

PHF-Illudin M

Anhydrous PHF, Mn 73 kDa (2.0 g), prepared as described in Example 1, was dissolved in 50 ml of dry pyridine. Then, 0.15 g of succinic anhydride and 18 mg DMAP were added. The reaction mixture was incubated for 18 hours at 40° C. The reaction resulted in quantitative acylation of PHF with formation of PHF-succinate that had 10% of its monomer units succinylated. After pyridine removal in vacuum, the PHF-succinate was dissolved in deionized water and purified by gel filtration on a Sephadex G-25 column equilibrated with deionized water. The final product was recovered from aqueous solution by lyophilization. Yield: nearly 100%.

PHF-succinate (100 mg) was dissolved in 2 ml of deionized water and mixed with 0.5 ml of DMF. Glycyl-Illudin, 10 mg, was dissolved in 0.5 mL of acetonitrile. The solutions were cooled down to 0° C. and mixed. Under intense agitation, EDC (1-ethyl-3-(3-diethylaminopropyl)carbodiimide; 20 mg) was added to the reaction mixture. The pH was adjusted to 5.9-6.0. After 30 minutes, the temperature of the reaction mixture was brought to ambient; agitation continued for another 3 hours. Glycyl-illudin association with PHF-succinate was monitored by size exclusion HPLC (detection: UV at 318 nm). Upon completion of the reaction, 15 ml of deionized water were added. The pH was adjusted to 5.5, and the reaction mixture was immediately desalted on Sephadex G-25. The product, PHF-Illudin, was lyophilized. Yield: nearly 100%. Polymer properties are reported in Table 4.

TABLE 4

Properties of PHF-Illudin M conjugates

| Sample number | % drug load[1] By weight | Molecular weight | Reasonable solubility[2] |
|---|---|---|---|
| 1 | 1.5% | 78,000 | 4 mg/mL |
| 2 | 3% | 78,000 | 7.5 mg/mL |
| 3 | 4% | 78,000 | 10 mg/mL |

[1]Drug load was determined by UV spectrometer at 318 nm.
[2]The reasonable solubility was determined by dissolved 250 mg conjugates in 1 mL of water. The viscosity of resulting solution was not too high to do IV injection.

EXAMPLE 15

Labeling

A dual labeled conjugate ($^3$H labeled CPT and $^{111}$In labeled backbone) was used for parallel independent monitoring of the conjugate components.

A [$^3$H] labeled PHF-CPT conjugate with 0.210 mCi/g activity and 7.0% w/w CPT content was prepared using [5-$^3$H (N)]-camptothecin (Moravek Biochemicals, Inc.) as described for PHF-CPT. The polymer backbone of the conjugate was modified with DTPA and labeled with $^{111}$In by transchelation from indium citrate at pH 5.5. Modification of PHF-CPT with DTPA was carried out in two steps. (1) Vicinal diols present in PHF structure (see Example 1) were oxidized with sodium metaperiodate at diol:periodate ratio 1:1, pH 5.7, for 2 hours at ambient temperature. The resultant pendant aldehyde groups were nonreductively aminated with DTPA amide of 1-amino-2-hydroxy-3-(aminooxy)-propan. The latter "aminooxy-DTPA", which forms oxime bonds with aldehydes under mild conditions, was prepared in our laboratory (synthesis to be described elsewhere). In our opinion oximes, being significantly more stable under physiological conditions than hydrazides[15] and generally less toxic, are more suitable for carbonyl modification in modular conjugates.

Radiochemical purities of all labeled derivatives were >98% (HPLC).

EXAMPLE 16

Biokinetics

Biokinetics and biodistributions of PHF-CPT conjugates were studied in normal rats and in nude mice with HT29 and A2780 xenografts using conjugates containing double-labeled labeled CPT conjugates. All animal studies were conducted in accordance with institutionally approved protocols.

Male nude/nu mice, average weight 28-32 g (Charles River Labs, Boston, Mass.), bearing 150-200 µl tumor xenografts (n=6 per group) were injected iv with the dual-labeled labeled PHF-CPT in 0.9% saline at 20 mg/kg based on CPT. The injected activities were 1.25 µCi/animal for $^3$H and 5 µCi/animal for $^{111}$In.

Adult outbred 240 g male rats (Charles River Laboratories, Boston, Mass.), n=6 per group, were injected iv with 800 µl of labeled PHF-CPT in 0.9% saline at 20 mg/kg by CPT. The injected activity per animal was 1.25 µCi and 24 µCi for $^3$H and $^{111}$In respectively.

Blood samples were taken at 5, 15, 30 minutes and 1, 2, 4, 8 and 24 hours time points. At 24 hours, the animals were euthanized; tumors and samples of major organs were harvested for counting. The total $^3$H and $^{111}$In activities in tissues were measured by scintillation (beta) and gamma counting respectively, and expressed as % injected dose/g tissue to characterize the distributions of $^3$H-CPT (total of all forms) and $^{111}$In-PHF.

Figure 5:
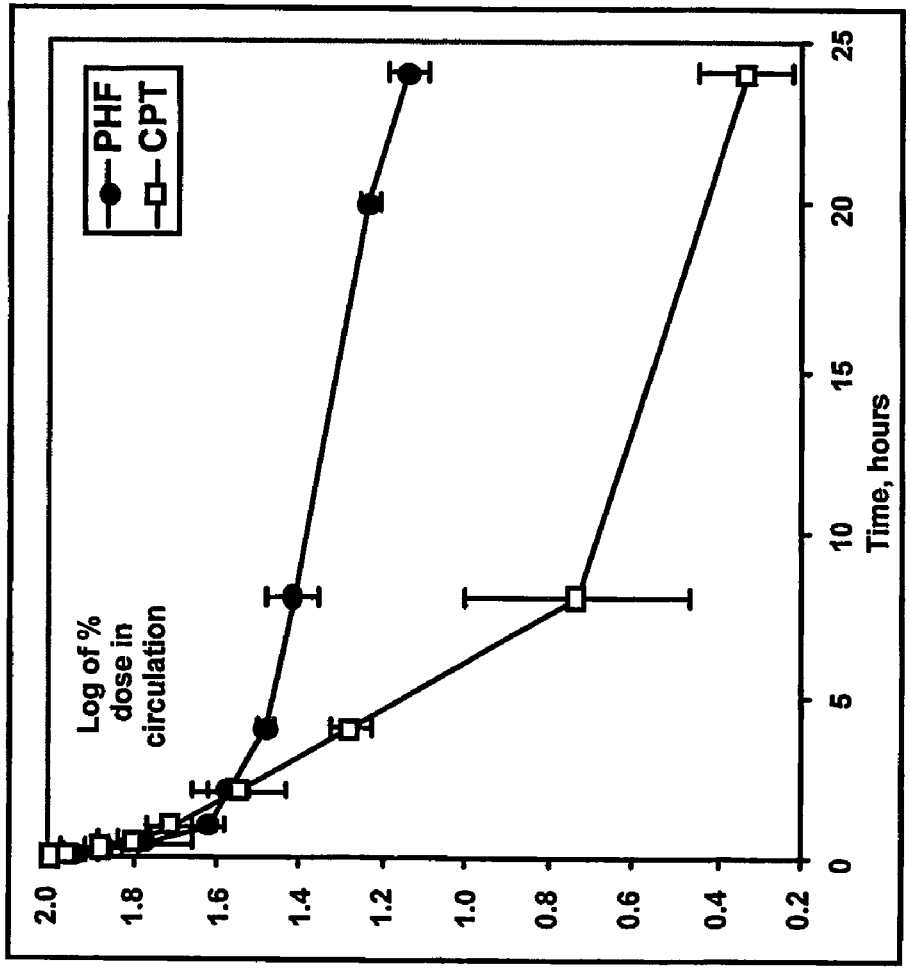
FIG. 5 depicts an exemplary biokinetics experiment of PHF-CPT conjugate (¹¹¹In-DTPA labeled PHF backbone and ³H labeled CPT).

The carrier polymer half-life in rat was found to be 14.2±1.7 hours, while the drug substance half-life was 2.1±0.2 hours, which corresponds well to the determined in vitro first phase release rate (FIG. 5).

Both $^3$H-CPT and $^{111}$In-PHF showed substantial accumulation in the tumor tissue. At 24 hours, CPT uptake in the tumor was 2.22% and 2.52% dose/g for A2780 and HT29, respectively, which is ca. 75-fold higher than for CPT (p<0.05) and very similar to PEG-CPT.[14] Mean tumor to muscle ratios were 2.4 and 1.5, respectively (p<0.2 for the difference between two different xenografts).

Figure 6:
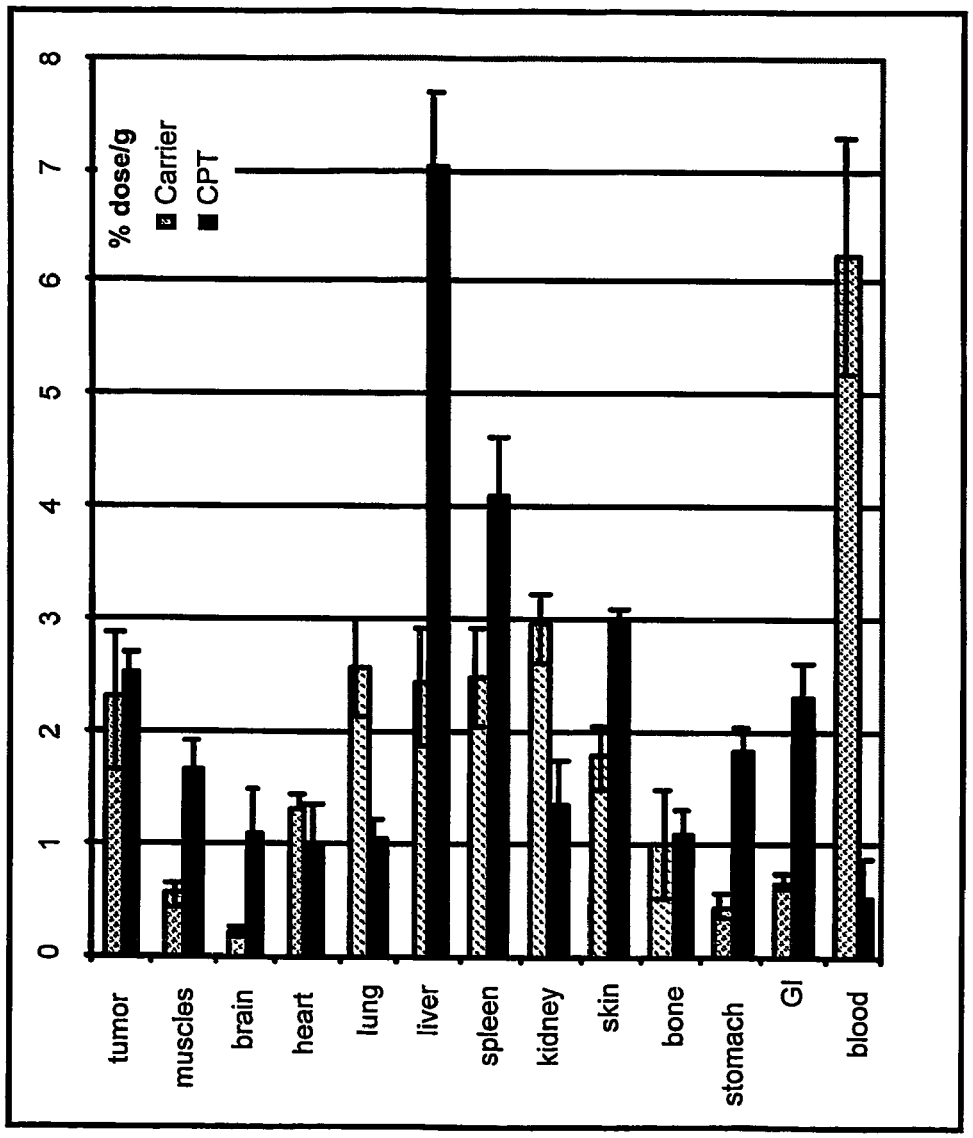
FIG. 6 depicts an exemplary biodistribution experiment of the carrier polymer (¹¹¹In) and CPT (³H) 24 hours post IV administration of double-labeled PHF-CPT. Xenograft: HT29, 0.1-0.15 ml tumors; n=6 per group.

Accumulation in other tissues (FIG. 6) was also similar to that of PEG-CPT. However, 2-3-fold higher drug levels were detected in the reticuloendothelial system (RES) tissues. Although it is not bound by theory, the latter could be either due to higher RES uptake of the CPT-SI then PEG-CPT, or due to a blood volume dependent pharmacokinetics.

Figure 7:
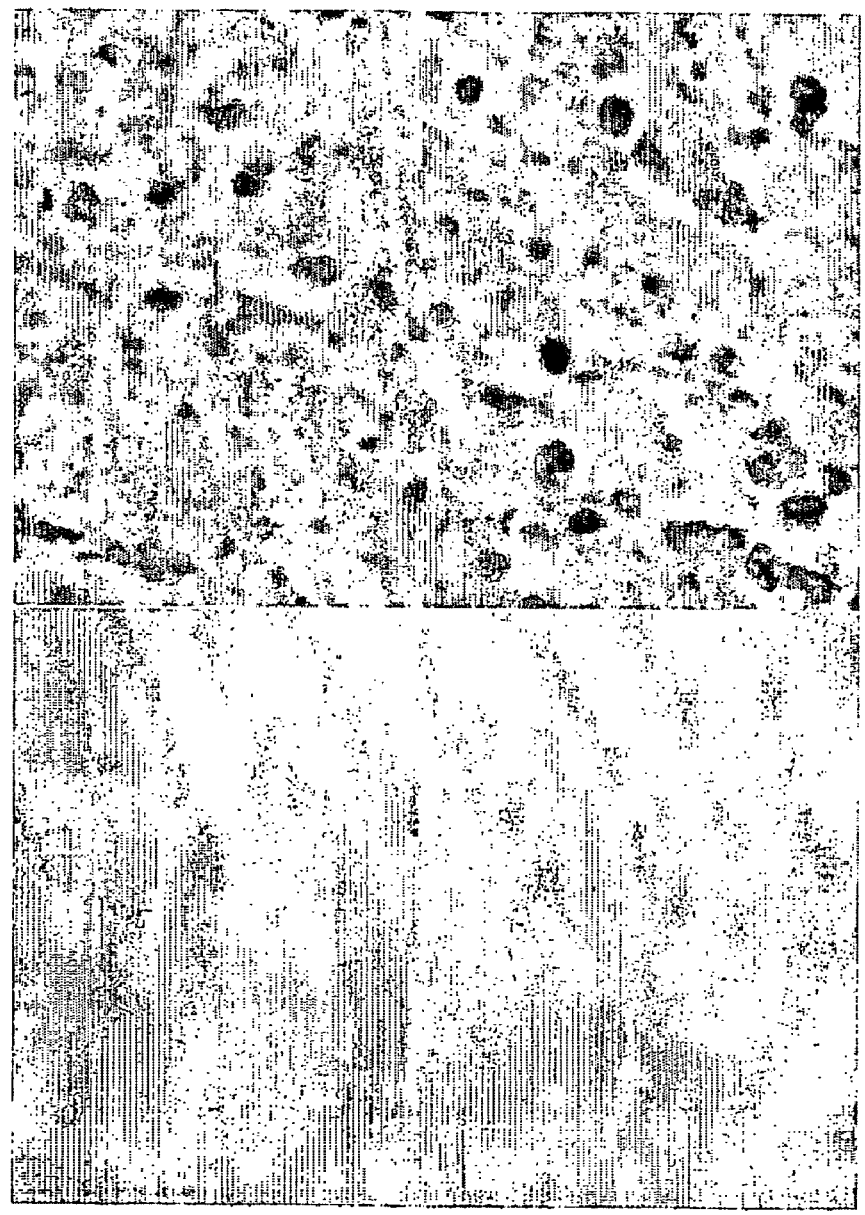
FIG. 7 depicts an exemplary microdistribution experiment of CPT in tumor tissue 24 hours post administration of PHF-CPT. CPT fluorescence (left) and phase contrast (right) images of the same region. Unstained unfixed 15 μm slice. Field: 80×130 μm.
Figure 8:
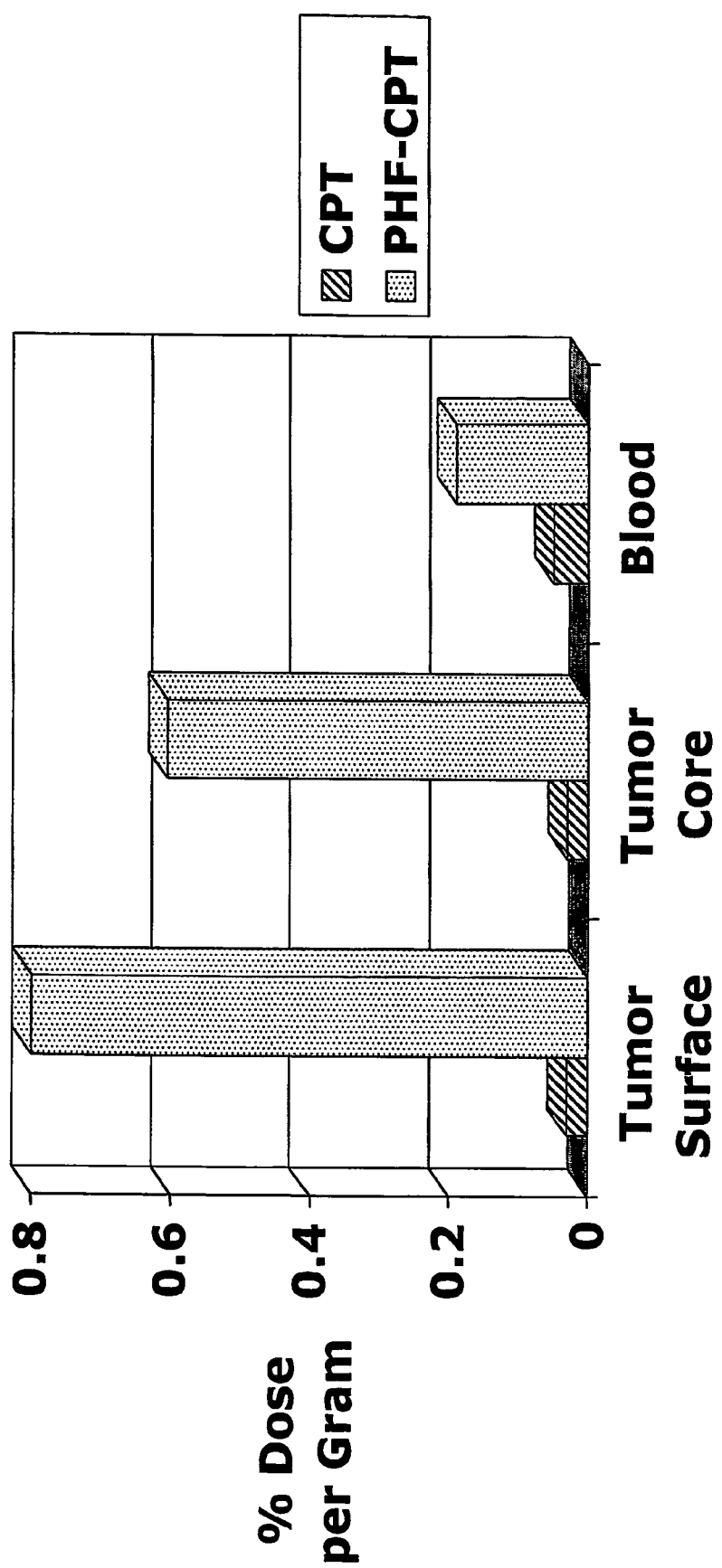
FIG. 8 depicts an exemplary comparative % dose per gram tissue distribution between CPT and PHF=CPT. HT29 xenograft in nude mice (n=6), administered IV at 20 mg of CPT per kg, 48 hours after injection, % dose per gram tissue. 26× Level Of CPT In Tumor with Fleximer 5× Dose in Circulation with Fleximer-CPT

Photoimaging (fluorescence microscopy) of CPT fluorescence in unstained unfixed tumor tissue 24 hours post administration showed relatively homogenous CPT distribution with elevated drug accumulation in some areas adjacent to vascular beds (FIG. 7). Diffuse intracellular distribution of CPT fluorescence indicated predominantly cytoplasmic (non-vesicular) drug localization.

EXAMPLE 17

Antiproliferative Activity

Cytotoxicity of CPT derivatives was investigated in HT29 cell culture. Cells were grown in McCoy's 5a medium with 1.5 mM L-glutamine supplemented with 10% FBS. The (exponentially growing) cells were seeded in 24-well culture plates (~10000 cells/well), cultured for 24 hours, and then treated with test compounds at various dilutions. Growth inhibition was assessed 72 hours post treatment (MTT assay). The ID50 of PHF-CPT in HT-29 cell culture was found to be 172 nM, which is 10-fold higher than CPT ID50 (17 nM), and 5-fold higher than CPT-SI ID50 (34 nM).

EXAMPLE 18

In Vivo Antineoplastic Activity and Toxicity

The toxicity of CPT was evaluated in normal outbred mice, as well as in xenograft bearing nude athymic animals in the course of antineoplastic activity studies.

The antineoplastic activity of PHF-CPT was evaluated with a HT-29 xenograft model in athymic mice in accordance with institutionally approved protocols. Camptothecin and CPT-SI (the first phase release product) were used as controls.

The study was carried out using approximately equitoxic doses of CPT and PHF-CPT. Cells were injected subcutaneously into the left flank, $10^6$ cells per animal in 50 µl. When tumor volume reached 100-150 $mm^3$, mice were randomly divided into four experimental groups: PHF-CPT, camptothecin, CPT-SI, and untreated control (n=3 each). Animals of the first three groups received the respective experimental substance via the tail vein in five doses every three days (5×q3D). Each injection contained 22.5 mg CPT eqv/kg of CPT and CPT-SI, and 45 mg CPT eqv/kg for PHF-CPT. All formulations were prepared immediately prior to administration. PHF-CPT was administered as a solution in 0.9% saline. CPT and CPT-SI were administered as dispersions in Tween 80/water (9/1 v/v). Animal weight, tumor size, animal appearance, behavior, and survival rate were monitored for four weeks after administration. Weight loss over 20% and tumor growth over 1500 $mm^3$ were counted as lethalities (animals were euthanized).

EXAMPLE 19

In Vivo Activity of PHF-CPT in LS174t Xenograft Model

Figure 3:
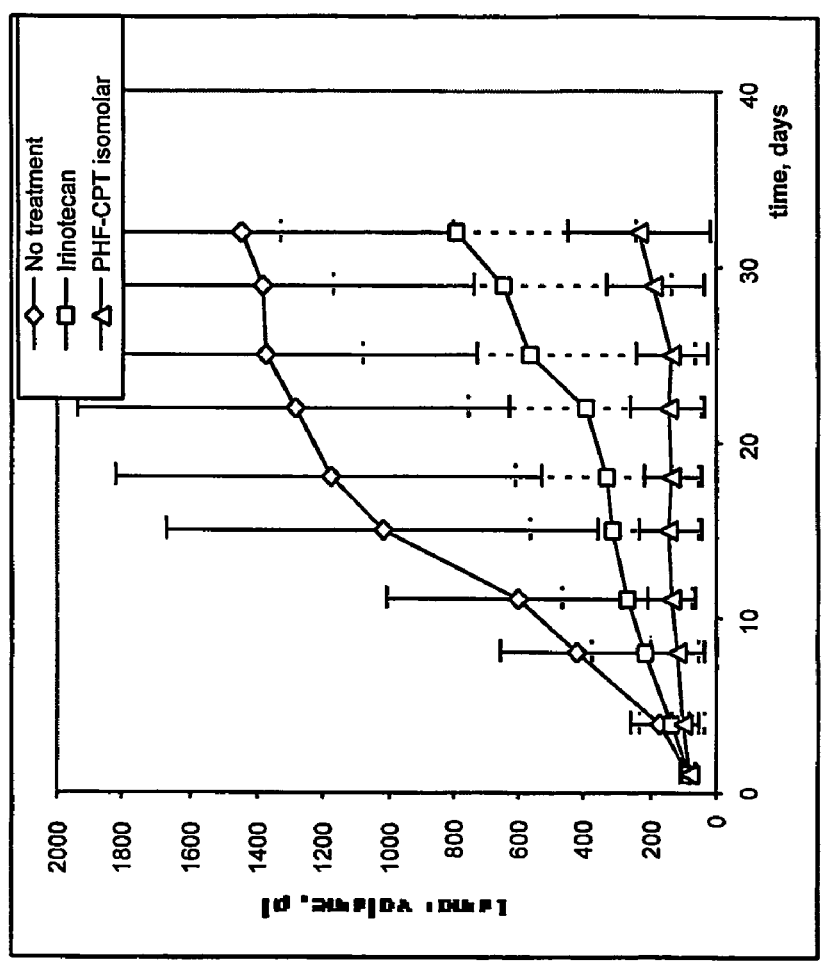
FIG. 3 depicts tumor volume dynamics in surviving animals with LS174t xenografts, n=10 per group, equal (160 nm/kg by CPT) doses of Irinotecan and PHF-CPT.
Figure 4:
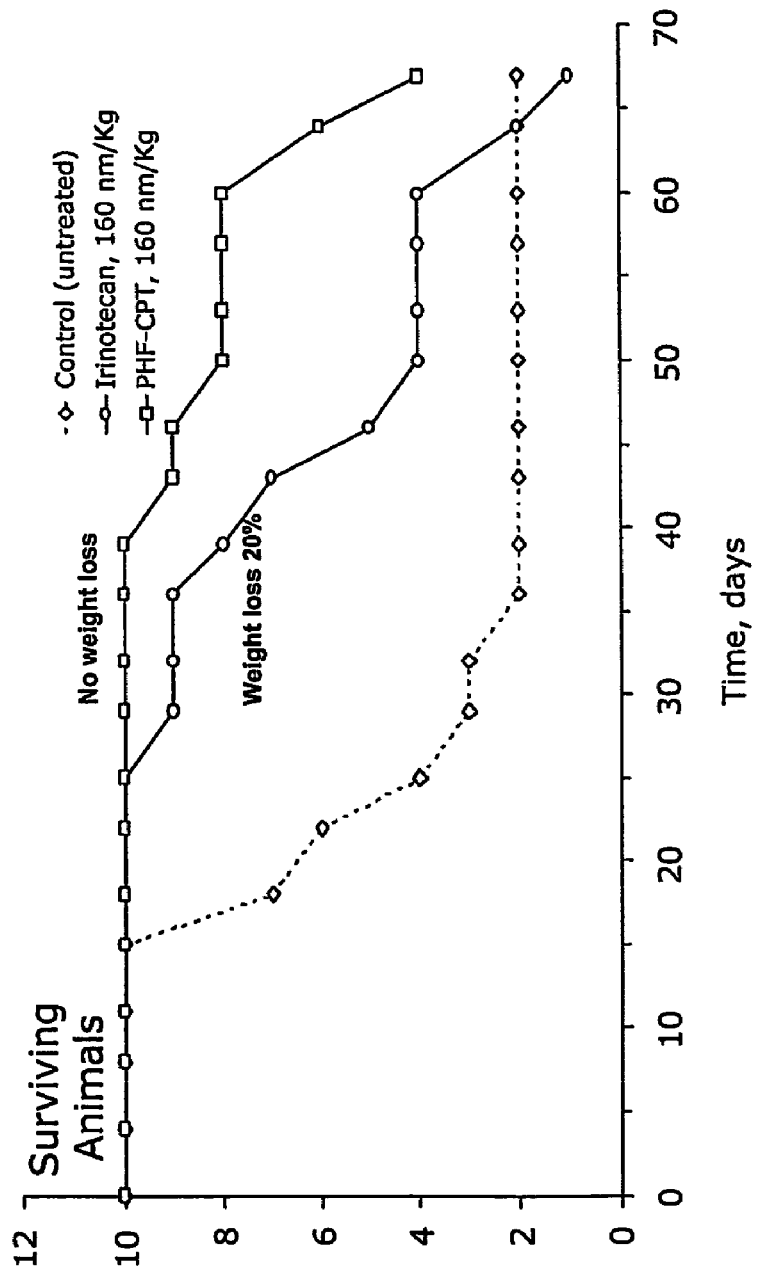
FIG. 4 depicts an exemplary animal survival study corresponding to the tumor size dynamics study of FIG. 3.

PHF-CPT was administered IV, 160 nm/kg by CPT, q7dx3 to nude mice with growing LS174t tumor xenografts. Irinotecan (a soluble low molecular weight CPT derivative, used as control) was administered IP, also at 160 nm/kg, following the same schedule. The results (FIGS. 3 and 4) demonstrated that, at the same doses (by drug substance), PHF-CPT suppressed tumor growth more potently than Irinotecan (FIG. 3). The group of animals treated with PHF-CPT had better survival rate than the group treated with Irinotecan (FIG. 4).

The maximum tolerated dose (MTD) of PHF-CPT was found to be >24 mg/kg, which is at least two-fold higher than for the low molecular weight CPT and Irinotecan (9-10 mg/kg for analogous schedules).

EXAMPLE 20

PHF-CPT Antineoplastic Toxicity

Antineoplastic toxicity of PHF-CPT was tested in the HT29 model (tumor size 100-150 µL), using CPT and CPT-SI as controls. The latter were administered as Cremofor® emulsions. PHF-CPT administered at 45 mg/kg by CPT (5×q3d.) was found to be both more effective and less toxic than unmodified CPT at 22.5 mg/kg (same schedule). The intermediate release product, CPT-SI, was found to have no significant effect on tumor dynamics, as determined by the time of tumor growth from 0.10-0.15 $cm^3$ to 1.5 $cm^3$ (27 days vs. 24 for untreated control and 40 days for CPT at 22.5 mg/kg 5×q4d).

REFERENCES

1. Wall M E, Wani M C, Cook C E, Palmer K H, McPhail A T, Sim G A. Plant antitumor agents. I. The isolation and structure of Camptothecin, a novel alkaloidal leukemia and tumor inhibitor from Camptothecia acuminata. J, Am. Chem. Soc. 1966, 88, 3888-3890
2. Fassberg J, Stella V J. A kinetic and mechanistic study of the hydrolysis of camptothecin and some analogues. J Pharm Sci 1992, 81:676-684
3. Cao Z. Harris N. Kozielski A. Vardeman D. Stehlin J S. Giovanella B. Alkyl esters of camptothecin and 9-nitro-camptothecin: synthesis, in vitro pharmacokinetics, toxicity, and antitumor activity. Journal of Medicinal Chemistry 1998, 41:31-37
4. Zhao H. Lee C. Sai P. Choe Y H. Boro M. Pendri A. Guan S. Greenwald R B. 20-O-acylcamptothecin derivatives: evidence for lactone stabilization. Journal of Organic Chemistry 2000, 65:4601-4606
5. Kaneda N. Nagata H. Furuta T. Yokokura T. Metabolism and pharmacokinetics of the camptothecin analogue CPT-11 in the mouse. Cancer Research 1990, 50:1715-1720
6. Duncan P Gac-Breton S. Keane R. Musila R. Sat Y N. Satchi R. Searle F. Polymer-drug conjugates, PDEPT and PELT: basic principles for design and transfer from the laboratory to clinic. Journal of Controlled Release 2001, 74:135-146
7. Burke T G. Bom D. Camptothecin design and delivery approaches for elevating anti-topoisomerase I activities in vivo. Annals of the New York Academy of Sciences 2000, 922:36-45
8. Schoemaker N E. van Kesteren C. Rosing H. Jansen S. Swart M. Lieverst J. Fraier D. Breda M. Pellizzoni C. Spinelli R. Grazia Porro M. Beijnen J H. Schellens J H. ten Bokkel Huinink W W. A phase I and pharmacokinetic study of MAG-CPT, a water-soluble polymer conjugate of camptothecin. British Journal of Cancer 2002, 87:608-614
9. Tadayoni B M. Friden P M. Walus L R. Musso G F. Synthesis, in vitro kinetics, and in vivo studies on protein conjugates of AZT: evaluation as a transport system to increase brain delivery. Bioconjugate Chemistry 1993, 4:139-145
10. Papisov M I. Acyclic polyacetals from polysaccharides. ACS Symp. Series 2001, 786:301-314,
11. Papisov M I. Biodegradable polyacetal polymers and methods of their formation and use. U.S. Pat. No. 5,811, 510, 09/22/1998
12. Greenwald R B, Pendri A, Conover C D, Lee C, Choe Y H, Gilbert C, Martinez A, Xia J, Wu D, Hsue M. Camptothecin-20-PEG ester transport forms: the effect of spacer groups on antineoplastic activity. Bioorg Med Chem 1998, 6:551-562
13. Minko T, Paranjpe P V, Qui B, Lalloo A, Won R, Stein S, Sinko P J. Enhancing the anticancer efficacy of camptothecin using biotinylated poly(ethyleneglycol) conjugates in sensitive and multidrug-resistant human ovarian carcinoma cells. Cancer Chemother Pharmacol 2002, 50:143-150.
14. C. Conover, R. Greenwald, A. Pendri, C. Gilbert, K. Shum. Camptothecin delivery systems: enhanced efficacy and tumor accumulation of camptothecin following its conjugation to polyethylene glycol via a glycine linker. Cancer Chemother Pharmacol. 1998, 42: 407-414
15. Webb, R. R., II, and Kancko, E. Synthesis of 1-(aminooxy)-4-[(3-nitro-2-pyridyl)dithio]butane hydrochloride and of 1-(aminooxy)$_4$-[(3-nitro-2-pyridyl)dithio]but-2-ene. Novel heterofunctional cross-linking reagents, Bioconjugate Chem. 1990, 1: 96-99.
16. Maeda H, Seymur L W, Miyamoto Y. Conjugates of anticancer agents and polymers: advantages of macromolecular therapeutics in vivo. Bioconj. Chem. 1992, 3:351-362
17. Papisov M I. Modeling in vivo transfer of long-circulating polymers (two classes of long circulating polymers and factors affecting their transfer in vivo). Adv. Drug Delivery Rev., Special issue on long circulating drugs and drug carriers, 1995, 16:127-137.
18. Maeda H, Seymur L W, Miyamoto Y. Conjugates of anticancer agents and polymers: advantages of macromolecular therapeutics in vivo. Bioconj. Chem. 1992, 3:351-362.
19. Greenwald R B. PEG drugs: an overview. Journal of Controlled Release 2001, 74:159-71.
20. Conover C D, Greenwald R B, Pendri A, Gilbert C W, Shum K L. Camptothecin delivery systems: enhanced efficacy and tumor accumulation of camptothecin following its conjugation to polyethylene glycol via a glycine linker. Cancer Chemother Pharmacol. 1998, 42:407-14.
21. Li C, Price J E, Milas L, Hunter N R, Ke S, Yu D F, Charnsangavej C, Wallace S. Antitumor activity of poly(L-glutamic acid)-paclitaxel on syngeneic and xenografted tumors. Clin Cancer Res. 1999, 5:891-7.
22. Matsumura Y, Maeda H. A new concept for macromolecular therapeutics in cancer chemotherapy: mechanism of tumoritropic accumulation of proteins and the antitumor agent SMANCS. Cancer Res. 1986 46:6387-92.
23. Rihova B, Kopeckova P, Strohalm J, Rossmann P, Vetvicka V, Kopecek J. Antibody-directed affinity therapy applied to the immune system: in vivo effectiveness and limited toxicity of daunomycin conjugated to HPMA copolymers and targeting antibody. Clin Immunol Immunopathol. 1988, 46:100-14
24. Ulbrich K, Etrych T, Chytil P, Jelinkova M, Rihova B. HPMA copolymers with pH-controlled release of doxorubicin. In vitro cytotoxicity and in vivo antitumor activity. J Control Release. 2003, 87:33-47
25. Duncan R, Gac-Breton S, Keane R, Musila R, Sat Y N, Satchi R, Searle F. Polymer-drug conjugates, PDEPT and PELT: basic principles for design and transfer from the laboratory to clinic. J Control Release. 2001, 74:135-46
26. Papisov M I, Garrido L, Poss K, Wright. C, Weissleder R, Brady T J. A long-circulating polymer with hydrolizable main chain. 23-rd International Symposium on Controlled Release of Bioactive Materials, Kyoto, Japan, 1996; Controlled Release Society, Deerfield, Ill., 1996; 107-108
27. Papisov M I. Theoretical considerations of RES-avoiding liposomes: molecular mechanics and chemistry of liposome interactions. Adv. Drug Delivery Rev. 1998, 32:119-138.
28. Papisov M I. Modeling in vivo transfer of long-circulating polymers (two classes of long circulating polymers and factors affecting their transfer in vivo). Adv. Drug Delivery Rev., Special issue on long circulating drugs and drug carriers, 1995, 16:127-137
29. Papisov M I. Acyclic polyacetals from polysaccharides. ACS Symposium Series 786 (2001), 301-314
30. A. Yurkovetskiy, S. Choi, A. Hiller, M. Yin, A. J. Fischman, M. I. Papisov. Biodegradable polyal carriers for protein modification. 29th Int. Symp. on Controlled Release of Bioactive Materials, 2002, Seoul, Korea. Controlled Release Society, Deerfield, Ill., 2002; paper # 357.
31. Papisov M I, Babich J W, Dotto P, Barzana M, Hillier S, Graham-Coco W, Fischman A J. (1998) Model cooperative (multivalent) vectors for drug targeting. 25th Int. Symp. on Controlled Release of Bioactive Materials, 1998, Las Vegas, Nev., USA; Controlled Release Society, Deerfield, Ill., 170-171
32. A. Yurkovetskiy, S. Choi, A. Hiller, M. Yin, C. McCusker, S. Syed, A. J. Fischman, M. I. Papisov. Biodegradable polyals for protein modification. Bioconj. Chem. 2003 (under review).
33. A. V. Yurkovetskiy, A. Hiller, M. Yin, S. Sayed, A. J. Fischman, M. I. Papisov. Biodegradable polyals for protein modification. Controlled Release Society's Winter Symposium, Salt Lake City, Utah, 2003.
34. Papisov M I. Biodegradable polyacetal polymers and methods of their formation and use. U.S. Pat. No. 5,811,510, Sep. 22, 1998; Papisov M I. Biodegradable polyketals. U.S. patent application 60/348,33; 2002; Papisov M., Kinstler O, Ladd D. Protein conjugates with a water-soluble biocompatible polymer. U.S. Patent Application 60/397,509; 2002; Papisov M., Yurkovetsky A. Oxime Conjugates and Methods of Preparation Thereof", U.S. Patent Application 60/397,283; 2002; Elmaleh D., Robson S., Papisov M. Conjugates comprising a biodegradable polymer and uses thereof. US patent application, Feb. 20, 2002.

What is claimed is:

1. A conjugate comprising a carrier substituted with one or more occurrences of a moiety having the structure:

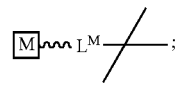

wherein:
each occurrence of M is independently a modifier having a molecular weight $\leq$10 kDa;
the modifier M is directly or indirectly attached to a linker $L^M$ through an amide bond;
the carrier is a polyacetal or polyketal and is linked directly or indirectly to each occurrence of a linker $L^M$ through an ester bond;
∿∿∿denotes direct or indirect attachment of M to linker $L^M$; and
each occurrence of a linker $L^M$ independently comprises a moiety having the structure:

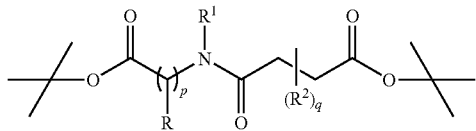

wherein:

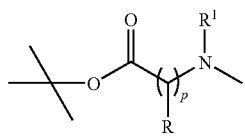

denotes the site of attachment to the modifier M; p is an integer from 1-12; q is an integer from 0-4; $R^1$ is hydrogen, —C(=O)$R^{1A}$, —C(=O)O$R^{1A}$, —S$R^{1A}$, SO$_2$$R^{1A}$ or an aliphatic, alicyclic, heteroaliphatic, heterocyclic, aryl, heteroaryl, aromatic, heteroaromatic moiety, wherein each occurrence of $R^{1A}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aromatic, heteroaromatic, aryl or heteroaryl; and each occurrence of R and $R^2$ is independently hydrogen, halogen, —CN, NO$_2$, an aliphatic, alicyclic, heteroaliphatic, heterocyclic, aryl, heteroaryl, aromatic, heteroaromatic moiety, or -G$R^{G1}$ wherein G is —O—, —S—, —N$R^{G2}$—, —C(=O)—, —S(=O)—, —SO$_2$—, —C(=O)O—, —C(=O)N$R^{G2}$—, —OC(=O)—, —N$R^{G2}$C(=O)—, —OC(=O)O—, —OC(=O)N$R^{G2}$—, —N$R^{G2}$C(=O)O—, —N$R^{G2}$C(=O)N$R^{G2}$—, —C(=S)—, —C(=S)S—, —SC(=S)—, —SC(=S)S—, —C(=N$R^{G2}$)—, —C(=N$R^{G2}$)O—, —C(=N$R^{G2}$)N$R^{G3}$—, —OC(=N$R^{G2}$)—, —N$R^{G2}$C(=N$R^{G3}$)—, —N$R^{G2}$SO$_2$—, —N$R^{G2}$SO$_2$N$R^{G3}$—, or —SO$_2$N$R^{G2}$—, wherein each occurrence of $R^{G1}$, $R^{G2}$ and $R^{G3}$ is independently hydrogen, halogen, or an optionally substituted aliphatic, heteroaliphatic, alicyclic, heteroalicyclic, aromatic, heteroaromatic, aryl or heteroaryl moiety.

2. The conjugate of claim 1, wherein p is 1.

3. The conjugate of claim 1, wherein p is 1 and R is hydrogen.

4. The conjugate of claim 1, wherein each occurrence of M is CPT or Taxol.

5. The conjugate of claim 1, wherein q is 0, p is 1, R and $R^1$ are each hydrogen, and each occurrence of M is CPT or Taxol.

6. A conjugate comprising a carrier substituted with one or more occurrences of a moiety having the structure:

wherein each occurrence of M is independently a modifier having a molecular weight <10 kDa;
∼∼∼denotes direct or indirect attachment of M to linker $L^M$; and
each occurrence of a linker $L^M$ independently comprises a moiety having the structure:

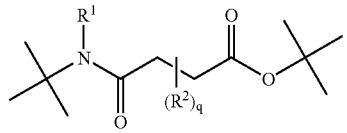

wherein

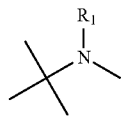

denotes the site of attachment to the modifier M;

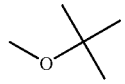

denotes the site of attachment to the carrier; q is an integer from 0-4; $R^1$ is hydrogen, —C(=O)$R^{1A}$, —C(=O)O$R^{1A}$, —S$R^{1A}$, SO$_2$$R^{1A}$ or an aliphatic, alicyclic, heteroaliphatic, heterocyclic, aryl, heteroaryl, aromatic, heteroaromatic moiety, wherein each occurrence of $R^{1A}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aromatic, heteroaromatic, aryl or heteroaryl; and each occurrence of $R^2$ is independently hydrogen, halogen, —CN, NO$_2$, an aliphatic, alicyclic, heteroaliphatic, heterocyclic, aryl, heteroaryl, aromatic, heteroaromatic moiety, or -G$R^{G1}$ wherein G is —O—, —S—, —N$R^{G2}$—, —C(=O)—, —S(=O)—, —SO$_2$—, —C(=O)O—, —C(=O)N$R^{G2}$—, —OC(=O)—, —N$R^{G2}$C(=O)—, —OC(=O)O—, —OC(=O)N$R^{G2}$—, —N$R^{G2}$C(=O)O—, —N$R^{G2}$C(=O)N$R^{G2}$—, —C(=S)—, —C(=S)S—, —SC(=S)—, —SC(=S)S—, —C(=N$R^{G2}$)—, —C(=N$R^{G2}$)O—, —C(=N$R^{G2}$)N$R^{G3}$—, —OC(=N$R^{G2}$)—, —N$R^{G2}$C(=N$R^{G3}$)—, —N$R^{G2}$SO$_2$—, —N$R^{G2}$SO$_2$N$R^{G3}$—, or —SO$_2$N$R^{G2}$—, wherein each occurrence of $R^{G1}$, $R^{G2}$ and $R^{G3}$ is independently hydrogen, halogen, or an optionally substituted aliphatic, heteroaliphatic, alicyclic, heteroalicyclic, aromatic, heteroaromatic, aryl or heteroaryl moiety;

whereby the modifier M is directly or indirectly attached to a linker $L^M$ through an amide bond, the carrier is linked directly or indirectly to each occurrence of a linker $L^M$ through an ester bond, and wherein the carrier is a polyacetal, wherein at least one occurrence of M comprises CPT or Taxol, and wherein CPT or Taxol is indirectly attached to linker $L^M$ via a glycine moiety.

7. A conjugate comprising a carrier substituted with one or more occurrences of a moiety having the structure:

wherein each occurrence of M is independently a modifier having a molecular weight ≦10 kDa;

∿∿∿ denotes direct or indirect attachment of M to linker $L^M$; and each occurrence of a linker $L^M$ independently comprises a moiety having the structure:

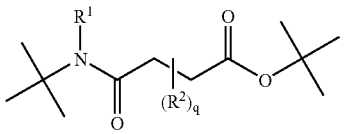

wherein

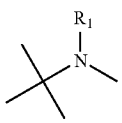

denotes the site of attachment to the modifier M;

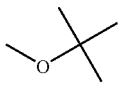

denotes the site of attachment to the carrier; q is an integer from 0-4; $R^1$ is hydrogen, —C(=O)$R^{1A}$, —C(=O)O$R^{1A}$, —S$R^{1A}$, SO$_2$$R^{1A}$ or an aliphatic, alicyclic, heteroaliphatic, heterocyclic, aryl, heteroaryl, aromatic, heteroaromatic moiety, wherein each occurrence of $R^{1A}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aromatic, heteroaromatic, aryl or heteroaryl; and each occurrence of $R^2$ is independently hydrogen, halogen, —CN, NO$_2$, an aliphatic, alicyclic, heteroaliphatic, heterocyclic, aryl, heteroaryl, aromatic, heteroaromatic moiety, or -G$R^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of $R^{G1}$, $R^{G2}$ and $R^{G3}$ is independently hydrogen, halogen, or an optionally substituted aliphatic, heteroaliphatic, alicyclic, heteroalicyclic, aromatic, heteroaromatic, aryl or heteroaryl moiety;

whereby the modifier M is directly or indirectly attached to a linker $L^M$ through an amide bond, the carrier is linked directly or indirectly to each occurrence of a linker $L^M$ through an ester bond, and wherein the carrier is a polyacetal, wherein each occurrence of M comprises CPT or Taxol, and wherein CPT or Taxol is indirectly attached to linker $L^M$ via a glycine moiety.

8. The conjugate of claim 6 or 7, comprising a PHF-CPT conjugate having n occurrences of the bracketed structure n, k occurrences of the bracketed structure k, and m occurrences of the bracketed structure m:

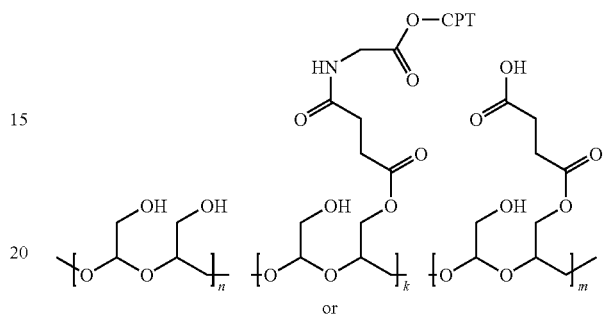

or

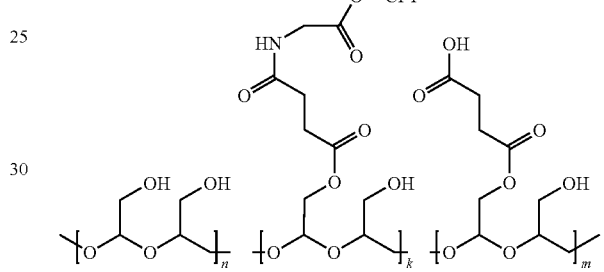

wherein n, k and m are integers between 10-300, 1-20, and 0-300 respectively.

9. The conjugate of claim 6 or 7, comprising a PHF-Taxol conjugate having n occurrences of the bracketed structure n, k occurrences of the bracketed structure k, and m occurrences of the bracketed structure m:

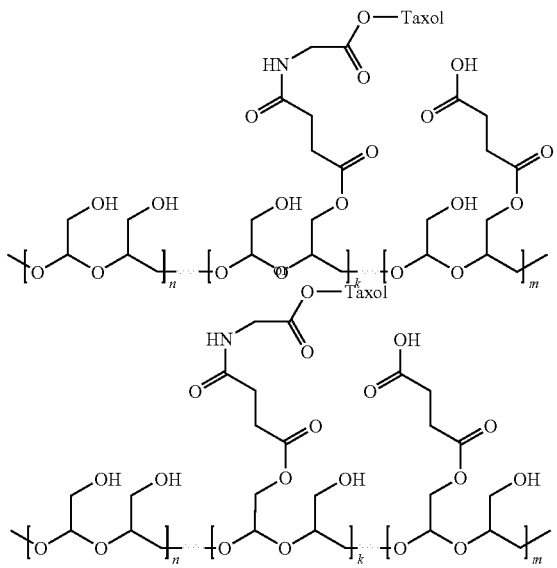

wherein n, k and m are integers between 10-300, 1-20, and 0-300 respectively.

10. The PHF-CPT conjugate of claim 8, wherein the

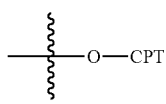

moiety has the structure:

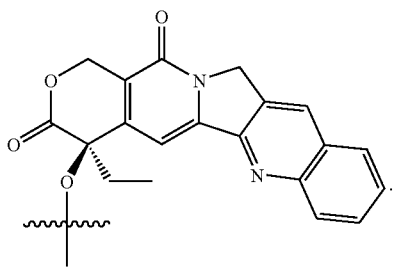

11. The PHF-Taxol conjugate of claim 9, wherein the

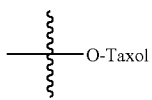

moiety has the structure:

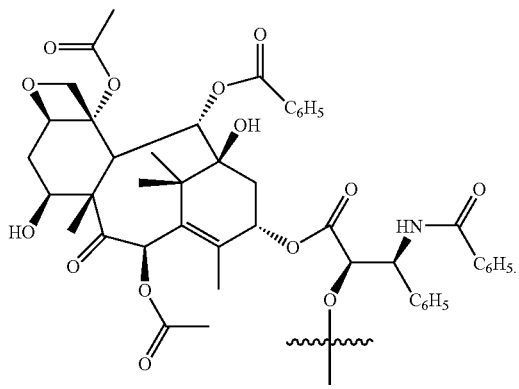

12. The conjugate of claim 1, wherein each occurrence of M is CPT.

13. The conjugate of claim 1, wherein each occurrence of M is taxol.

14. The conjugate of claim 5, wherein each occurrence of M is CPT.

15. The conjugate of claim 5, wherein each occurrence of M is taxol.

16. The conjugate of claim 7, wherein each occurrence of M is CPT.

17. The conjugate of claim 7, wherein each occurrence of M is taxol.

18. The conjugate of claim 6, wherein at least one occurrence of M comprises CPT.

19. The conjugate of claim 6, wherein at least one occurrence of M comprises taxol.

20. A composition comprising the conjugate of claim 1 and a pharmaceutically suitable carrier or diluent.

21. A composition comprising the conjugate of claim 6 and a pharmaceutically suitable carrier or diluent.

22. A composition comprising the conjugate of claim 7 and a pharmaceutically suitable carrier or diluent.

23. The conjugate of claim 1, wherein the carrier is PHF (poly(1-hydroxymethylethylene hydroxymethyl-formal)).

24. The conjugate of claim 5, wherein the carrier is PHF (poly(1-hydroxymethylethylene hydroxymethyl-formal)).

25. The conjugate of claim 6, wherein the carrier is PHF (poly(1-hydroxymethylethylene hydroxymethyl-formal)).

26. The conjugate of claim 7, wherein the carrier is PHF (poly(1-hydroxymethylethylene hydroxymethyl-formal)).

27. The conjugate of claim 14, wherein the carrier is PHF (poly(1-hydroxymethylethylene hydroxymethyl-formal)).

28. The composition of claim 20, wherein the carrier is PHF (poly(1-hydroxymethylethylene hydroxymethyl-formal)).

29. The composition of claim 21, wherein the carrier is PHF (poly(1-hydroxymethylethylene hydroxymethyl-formal)).

30. The composition of claim 22, wherein the carrier is PHF (poly(1-hydroxymethylethylene hydroxymethyl-formal)).

* * * * *

UNITED STATES PATENT AND TRADEMARK OFFICE
CERTIFICATE OF CORRECTION

PATENT NO. : 7,790,150 B2
APPLICATION NO. : 10/570466
DATED : September 7, 2010
INVENTOR(S) : Mikhail I. Papisov and Alexander Yurkovetskiy It is certified that error appears in the above-identified patent and that said Letters Patent is hereby corrected as shown below:

In claim 1, column 74, lines 56-57, please delete:

"each occurrence of M is independently a modifier having a molecular weight $\leqq$ 10 kDa;", and insert:

-- each occurrence of M is independently a modifier having a molecular weight $\leq$ 10 kDa;--.

In claim 1, column 75, line 40, please delete:

"(=$NR^{G2}$)--$NR^{G2}C$(=$NR^{G3}$)-, -$NR^{G2}SO_2$-,", and insert:

--(=$NR^{G2}$)-, -$NR^{G2}C$(=$NR^{G3}$)-, -$NR^{G2}SO_2$-,--.

In claim 6, column 75, lines 62-63, please delete:

"wherein each occurrence of M is independently a modifier having a molecular weight < 10 kDa;", and insert:

--wherein each occurrence of M is independently a modifier having a molecular weight $\leq$ 10 kDa;--.

In claim 7, column 77, lines 7-8, please delete:

"wherein each occurrence of M is independently a modifier having a molecular weight $\leqq$ 10 kDa;", and insert:

--wherein each occurrence of M is independently a modifier having a molecular weight $\leq$ 10 kDa;--.

Signed and Sealed this
Tenth Day of January, 2012

David J. Kappos
*Director of the United States Patent and Trademark Office*

CERTIFICATE OF CORRECTION (continued)
U.S. Pat. No. 7,790,150 B2

In claim 9, column 78, lines 43-65, please delete:

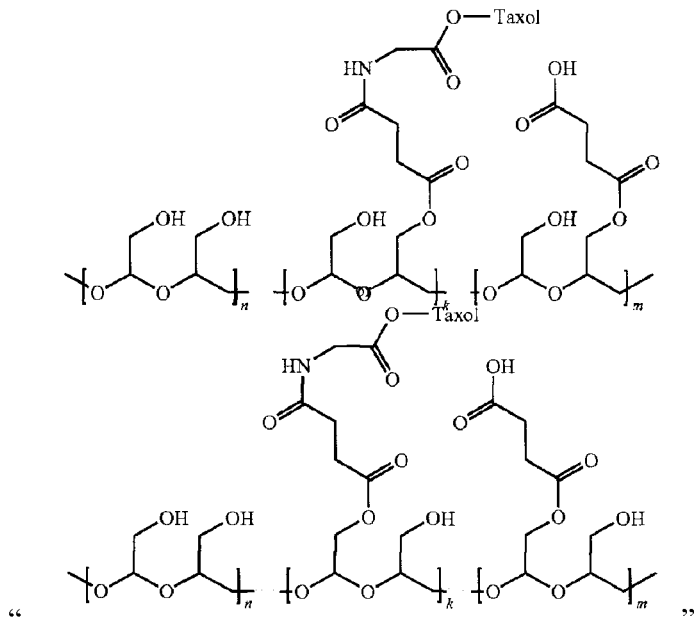

"

"

and insert:

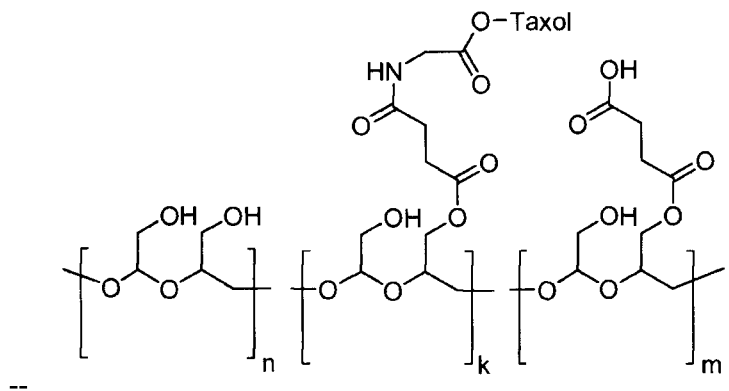

-- or

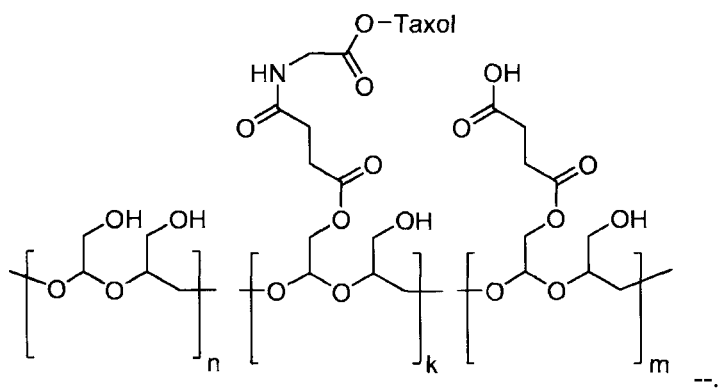

--.